United States Patent
de Sauvage et al.

(10) Patent No.: US 7,625,759 B2
(45) Date of Patent: Dec. 1, 2009

(54) METHOD FOR USING BOC/CDO TO MODULATE HEDGEHOG SIGNALING

(75) Inventors: Frederic J. de Sauvage, Foster City, CA (US); Hua Tian, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/625,717

(22) Filed: Jan. 22, 2007

(65) Prior Publication Data

US 2007/0237774 A1    Oct. 11, 2007

Related U.S. Application Data

(63) Continuation-in-part of application No. 11/609,472, filed on Dec. 12, 2006, now abandoned.

(60) Provisional application No. 60/789,645, filed on Apr. 5, 2006, provisional application No. 60/752,220, filed on Dec. 19, 2005.

(51) Int. Cl.
    H01L 21/20      (2006.01)
    A61K 38/00      (2006.01)
(52) U.S. Cl. .......................... 436/86; 514/12
(58) Field of Classification Search .................. 514/12; 436/86
    See application file for complete search history.

(56) References Cited

U.S. PATENT DOCUMENTS

| | | | |
|---|---|---|---|
| 4,816,567 | A | 3/1989 | Cabilly et al. |
| 5,229,275 | A | 7/1993 | Goroff |
| 5,428,130 | A | 6/1995 | Capon et al. |
| 5,545,806 | A | 8/1996 | Lonberg et al. |
| 5,545,807 | A | 8/1996 | Surani et al. |
| 5,565,332 | A | 10/1996 | Hoogenboom et al. |
| 5,567,610 | A | 10/1996 | Borrebaeck et al. |
| 5,569,825 | A | 10/1996 | Lonberg et al. |
| 5,571,894 | A | 11/1996 | Wels et al. |
| 5,573,905 | A | 11/1996 | Lerner et al. |
| 5,587,458 | A | 12/1996 | King et al. |
| 5,591,669 | A | 1/1997 | Krimpenfort et al. |
| 5,641,870 | A | 6/1997 | Rinderknecht et al. |
| 2003/0064443 | A1 | 4/2003 | Baker et al. |
| 2005/0085519 | A1 | 4/2005 | Rubin et al. |

FOREIGN PATENT DOCUMENTS

| | | |
|---|---|---|
| WO | 93/16185 | 8/1993 |
| WO | 95/18856 | 7/1995 |
| WO | 96/17924 | 6/1996 |
| WO | 02/30462 | 4/2002 |
| WO | 2006/132788 A2 | 12/2006 |

OTHER PUBLICATIONS

Apelqvist et al., "Sonic Hedgehog Directs Specialised Mesoderm Differentiation in the Intestine and Pancreas" *Current Biology* 7(10):801-804 (Oct. 1, 1997).
Beck and D'Amore, "Vascular development: cellular and molecular regulation" *FASEB J.* 11(5):365-373 (Apr. 1997).
Bellusci et al., "Involvement of Sonic Hedgehog (Shh) in Mouse Embryonic Lung Growth and Morphogenesis" *Development* 124(1):53-63 (Jan. 1997).
Bitgood et al., "Sertoli Cell Signaling by Desert Hedgehog Regulates the Male Germline" *Current Biology* 6(3):298-304 (Mar. 1, 1996).
Boring et al., "Cancer Statistics, 1993" *CA Cancer J. Clin.* 43(1):7-26 (Jan.-Feb. 1993).
Brennan et al., "Preparation of bispecific antibodies by chemical recombination of monoclonal immunoglobulin $G_1$ fragments" *Science* 229(4708):81-83 (Jul. 5, 1985).
Bruggemann et al., "Designer Mice: The Production of Human Antibody Repertoires in Transgenic Animals" *Year Immunol.* 7:33-40 (1993).
Buschmann and Scaper, "The pathophysiology of the collateral circulation (arteriogenesis)" *Journal of Pathology* 190(3):338-342 (Feb. 2000).
Carpenter et al., "Characterization of Two Patched Receptors for the Vertebrate Hedgehog Protein Family." *Proc. Natl. Acad. Sci. USA* 95(23):13630-13634 (Nov. 1998).
Carter et al., "High Level *Escherichia coli* Expression and Production of a Bivalent Humanized Antibody Fragment" *Bio/Technology* 10(2):163-167 (Feb. 1992).
Carter et al., "Humanization of an Anti-p185$^{HER2}$ Antibody For Human Cancer Therapy"*Proc. Natl. Acad. Sci. USA* 89(10):4285-4289 (May 1992).
Cherrington et al., "New paradigms for the treatment of cancer: the role of anti-angiogenesis agents" *Adv. Cancer Res.* 79:1-38 (2000).
Chothia and Lesk, "Canonical Structures for the Hypervariable Regions of Immunoglobulins" *J Mol Biol.* 196(4):901-917 (Aug. 20, 1987).
Clackson et al., "Making Antibody Fragments Using Phage Display Libraries" *Nature* 352 (6336):624-628 (Aug. 15, 1991).
Cole et al., "Microform holoprosencephaly in mice that lack the Ig superfamily member Cdon" *Curr Biol.* 13(5):411-415 (Mar. 4, 2003).
Echelard et al., "Sonic hedgehog, a member of a family of putative signaling molecules, is implicated in the regulation of CNS polarity" *Cell* 75(7):1417-1430 (Dec.31, 1993).
Ericson et al., "Sonic hedgehog induces the differentiation signal for ventral forebrain neurons: a common signal for ventral patterning within the neural tube" *Cell* 81(5):747-756 (Jun. 2, 1995).

(Continued)

*Primary Examiner*—Maryam Monshipouri
(74) *Attorney, Agent, or Firm*—Patrick J. Farley; Craig Svoboda

(57) ABSTRACT

The present invention provides for a method of using BOC/CDO hedgehog antagonists to inhibit hedgehog signaling, as well as treating and diagnosing disorders relating to hedgehog signaling or overexpression of hedgehog, including cancer, cell proliferative disorders, and angiogenesis, neurological disorders, as well as other conditions affected by hedgehog signaling such as hair growth, neural stem cell differentiation, chondrogenesis and osteogenesis, lung surfactant production, formation of lamellated bodies in lung cells.

8 Claims, 12 Drawing Sheets

OTHER PUBLICATIONS

Evan et al., "Isolation of Monoclonal Antibodies Specific for Human c-myc Proto-Oncogene Product" *Molecular & Cellular Biology* 5(12):3610-3616 (Dec. 1985).

Fan and Tessier-Levigne, "Patterning of mammalian somites by surface ectoderm and notochord: evidence for sclerotome induction by a hedgehog homolog" *Cell* 79(7):1175-1186 (Dec. 30, 1994).

Field et al., "Purification of a RAS-Responsive Adenylyl Cyclase Complex from *Saccharomyces cerevisiae* by Use of an Epitope Addition Method" *Molecular & Cellular Biology* 8(5):2159-2165 (May 1988).

Folkman and Shing, "Angiogenesis" *Biol Chem.* 267(16):10931-10934 (Jun. 5, 1992).

Folkman, "Tumor angiogenesis" *Adv Cancer Res.* 43:175-203 (1985).

Griffiths et al., "Human anti-self antibodies with high specificity from phage display libraries" *EMBO Journal* 12(2):725-734 (Feb 1993).

Hannon and Rossi, "Unlocking the potential of the human genome with RNA interference" *Nature* 431(7006):371-378 (Sep. 16, 2004).

Ho et al., "Sonic hedgehog in the nervous system: functions, modifications and mechanisms" *Curr. Opin. Neurobiol.* 12(1):57-63 (Feb. 2002).

Hopp et al., "A Short Polypeptide Marker Sequence Useful for Recombinant Protein Identification and Purification" *Bio/Technology* 6:1204-1210 (1988).

Hynes et al., "Control of Cell Pattern in the Neural Tube by the Zinc Finger Transcription Factor and Oncogene Gli-1" *Neuron.* 19(1):15-26 (Jul. 1997).

Jakobovits at al., "Analysis of Homozygous Mutant Chimeric Mice: Deletion of the Immunoglobulin Heavy-Chain Joining Region Blocks B-cell Development and Antibody Production" *Proc. Natl. Acad. Sci. USA* 90(6):2551-2555 (Mar. 15, 1993).

Jakobovits et al., "Germ-line Transmission and Expression of a Human-Derived Yeast Artificial Chromosome" *Nature* 362(6417):255-258 (Mar. 18, 1993).

Jarov et al., "A dual role for Sonic hedgehog in regulating adhesion and differentiation of neuroepithelial cells" *Dev. Biol.* 261(2):520-536 (Sep. 15, 2003).

Johnson & Chiswell, "Human antibody engineering" *Current Opinion in Structural Biology* 3:564-571 (1993).

Johnson et al., "Ectopic Expression of Sonic Hedgehog Alters Dorsal-Ventral Patterning or Somites" *Cell* 79(7):1165-1173 (Dec. 30, 1994).

Jones et al., "Replacing the Complementarity-Determining Regions in a Human Antibody with Those From a Mouse" *Nature* 321(6069):522-525 (May 29, 1986).

Kang et al., "BOC, an Ig superfamily member, associates with CDO to positively regulate myogenic differentiation" *EMBO Journal* 21(1-2):114-124 (Jan. 15, 2002).

Kang et al., "CDO, a robo-related cell surface protein that mediates myogenic differentiation" *J Cell Biol.* 143(2):403-413 (Oct 19, 1998).

Kang et al., "Promyogenic members of the Ig and cadherin families associate to positively regulate differentiation" *Proc Natl Acad Sci U S A* 100(7):3989-3994 (Apr. 1, 2003).

Klagsbrun and D'Amore, "Regulators of angiogenesis" *Ann. Rev. Physiol.* 53:217-239 (1991).

Kohler and Milstein, "Continuous.Cultures of Fused Cells Secreting Antibody of Predefined Specificity" *Nature* 256(5517):495-497 (Aug. 7, 1975).

Krauss et al., "A Functionally Conserved Homolog of the *Drosophila* Segment Polarity Gene hh is Expressed in Tissues with Polarizing Activity in Zebrafish Embryos" *Cell* 75(7):1431-1444 (Dec. 31, 1993).

Lum et al., "Identification of Hedgehog pathway components by RNAi in *Drosophila* cultured cells" *Science* 299(5616):2039-2045 (Mar. 28, 2003).

Lutz-Freyermuth et al., "Quantitative Determination That One of Two Potential RNA-binding Domains of the A Protein Component of the U1 Small Nuclear Ribonucleoprotein Complex Binds with High Affinity to Stem-loop II of U1 RNA" *Proc. Natl. Acad. Sci. USA* 87:6393-6397 (Aug. 1990).

Marks et al., "By-Passing Immunization: Human Antibodies From V-gene Libraries Displayed On Phage" *J. Mol. Biol.* 222(3):581-597 (Dec. 5, 1991).

Marti et al., "Requirement of 19K Form of Sonic Hedgehog for Induction of Distinct Ventral Cell Types in CNS Explants" *Nature* 375(6529):322-325 (May 25, 1995).

Martin et al., "GAP Domains Responsible for Ras p21-Dependent Inhibition of Muscarinic Atrial $K^{+\ Channel\ Currents}$" *Science* 255:192-194 (Jan. 10, 1992).

McCafferty et al., "Phage antibodies: filamentous phage displaying antibody variable domains" *Nature* 348:552-554 (Dec. 6, 1990).

Morimoto et al., "Single-step purification of $F(ab')_2$ fragments of mouse monoclonal antibodies (immunoglobulins G1) by hydrophobic interaction high performance liquid chromatography using TSKgel Phenyl-5PW" *J Biochem Biophys Methods* 24(1-2):107-117 (Mar. 1992).

Morrison et al., "Chimeric Human Antibody Molecules: Mouse Antigen-Binding Domains with Human Constant Region Domains" *Proc. Natl. Acad. Sci. USA* 81(21):6851-6855 (Nov. 1984).

Motoyama et al., "Ptch2, a second mouse Patched gene is co-expressed with Sonic hedgehog" *Nature Genetics* 18(2):104-106 (Feb. 1998).

Nybakken et al., "Hedgehog signal transduction: recent findings" *Curr. Opin. Genet. Dev.* 12(5):503-511 (Oct. 2002).

Oro et al., "Basal Cell Carcinomas in Mice Overexpressing Sonic Hedgehog" *Science* 276 (5313:817-821 (May 2, 1997).

Paborsky et al., "Mammalian Cell Transient Expression of Tissue Factor for the Production of Antigen" *Protein Eng.* 3(6):547-553 (May 1990).

Paddison et al., "Stable suppression of gene expression by RNAi in mammalian cells" *Proc. Natl Acad Sci* 99(3):1443-1448 (Feb. 5, 2002).

Pluckthun, "Antibodies From *Escherichia coli*" *The Pharmacology of Monoclonal Antibodies: Handbook of Pharmacology*, Rosenberg and Moore, eds., Berlin:Springer-Verlag, Chapter 11, vol. 113:269-315 (1994).

Presta et al., "Humanization of an Antibody Directed Against IgE" *J. Immunol.* 151(5):2623-2632 (Sep. 1, 1993).

Presta, L., "Antibody Engineering" *Current Opinion in Structural Biology* 2:593-596 (1992).

Reichmann, L. et al., "Reshaping human antibodies for therapy" *Nature* 332:323-337 (1988).

Roberts et al., "Sonic Hedgehog is An Endodermal Signal Inducing Bmp-4 and Hox Genes During Induction and Regionalization of the Chick Hindgut" *Development* 121(10):3163-3174 (Oct. 1995).

Ruiz i Altaba A., "Hedgehog-Gli signalling and the growth of the brain" *Nat. Rev. Neursci.* 3(1):24-33 (Jan. 2002).

Sandy et al., "Mammalian RNAi: a practical guide" *Biotechniques* 39(2):215-224 (Aug. 2005).

Sims et al., "A Humanized CD18 Antibody Can Block Function Without Immunology Cell Destruction" *The Journal of Immunology* 151(4):2296-2308 (Aug. 15, 1993).

Skinner et al., "Use of the Glu-Glu-Phe C-Terminal Epitope for Rapid Purification of the Catalytic Domain of Normal and Mutant ras GTPase-activating Proteins." *J. Bio. Chem.* 266:14163-14166 (1991).

Stecca et al., "The Therapeutic Potential of Modulators of the Hedgehog-Gli Signaling Pathway" *Journal of Biology* 1(2):9 (Nov. 6, 2002).

Verhoeyen et al., "Reshaping Human Antibodies: Grafting an Antilysozyme Activity" *Science* 239:1534-1536 (Mar. 25, 1988).

Vortkamp et al., "Regulation of rate of cartilage differentiation by Indian hedgehog and PTH-related protein" *Science* 273(5275):613-622 (Aug. 2, 1996).

Wegorzewska et al., "Overexpression of the immunoglobulin superfamily members CDO and BOC enhances differentiation of the human rhabdomyosarcoma cell line RD" *Mol Carcinog.* 37(1):1-4 (May 2003).

Yancopoulos et al., "Vasculogenesis, angiogenesis, and growth factors: ephrins enter the fray at the border" *Cell* 93(5):661-664 (May 29, 1998).

Zapata et al., "Engineering Linear F(ab')$_2$ Fragments For Efficient Production in *Escherichia coli* and Enhanced Antiproliferative Activity" *Protein Engineering* 8(10):1057-1062 (Oct. 8, 1995).

FIGURE 1A

GTTTCTCATAGTTGGCGTCTTCTAAAGGAAAAACACTAAAATGAGGAACTCAGCGGACCG
GGAGCGACGCAGCTTGAGGGAAGCATCCCTAGCTGTTGGCGCAGAGGGGCGAGGCTGAAG
CCGAGTGGCCCGAGGTGTCTGAGGGGCTGGGGCAAAGGTGAAAGAGTTTCAGAACAAGCT
TCCTGGAACCCATGACCCATGAAGTCTTGTCGACATTTATACCGTCTGAGGGTAGCAGCT
CGAAACTAGAAGAAGTGGAGTGTTGCCAGGGACGGCAGTATCTCTTTGTGTGACCCTGGC
GGCCTATGGGACGTTGGCTTCAGACCTTTGTGATACACCATGCTGCGTGGGACGATGACG
GCGTGGAGAGGAATGAGGCCTGAGGTCACACTGGCTTGCCTCCTCCTAGCCACAGCAGGC
TGCTTTGCTGACTTGAACGAGGTCCCTCAGGTCACCGTCCAGCCTGCGTCCACCGTCCAG
AAGCCCGGAGGCACTGTGATCTTGGGCTGCGTGGTGGAACCTCCAAGGATGAATGTAACC
TGGCGCCTGAATGGAAAGGAGCTGAATGGCTCGGATGATGCTCTGGGTGTCCTCATCACC
CACGGGACCCTCGTCATCACTGCCCTTAACAACCACACTGTGGGACGGTACCAGTGTGTG
GCCCGGATGCCTGCGGGGCTGTGGCCAGCGTGCCAGCCACTGTGACACTAGCCAATCTC
CAGGACTTCAAGTTAGATGTGCAGCACGTGATTGAAGTGGATGAGGGAAACACAGCAGTC
ATTGCCTGCCACCTGCCTGAGAGCCACCCCAAAGCCCAGGTCCGGTACAGCGTCAAACAA
GAGTGGCTGGAGGCCTCCAGAGGTAACTACCTGATCATGCCCTCAGGGAACCTCCAGATT
GTGAATGCCAGCCAGGAGGACGAGGGCATGTACAAGTGTGCAGCCTACAACCCAGTGACC
CAGGAAGTGAAAACCTCCGGCTCCAGCGACAGGCTACGTGTGCGCCGCTCCACCGCTGAG
GCTGCCCGCATCATCTACCCCCCAGAGGCCCAAACCATCATCGTCACCAAAGGCCAGAGT
CTCATTCTGGAGTGTGTGGCCAGTGGAATCCCACCCCCACGGGTCACCTGGGCCAAGGAT
GGGTCCAGTGTCACCGGCTACAACAAGACGCGCTTCCTGCTGAGCAACCTCCTCATCGAC
ACCACCAGCGAGGAGGACTCAGGCACCTACCGCTGCATGGCCGACAATGGGGTTGGGCAG
CCCGGGGCAGCGGTCATCCTCTACAATGTCCAGGTGTTTGAACCCCCTGAGGTCACCATG
GAGCTATCCCAGCTGGTCATCCCCTGGGGCCAGAGTGCCAAGCTTACCTGTGAGGTGCGT
GGGAACCCCCCGCCCTCCGTGCTGTGGCTGAGGAATGCTGTGCCCCTCATCTCCAGCCAG
CGCCTCCGGCTCTCCCGCAGGGCCCTGCGCGTGCTCAGCATGGGCCTGAGGACGAAGGC
GTCTACCAGTGCATGGCCGAGAACGAGGTTGGGAGCGCCCATGCCGTAGTCCAGCTGCGG
ACCTCCAGGCCAAGCATAACCCCAAGGCTATGGCAGGATGCTGAGCTGGCTACTGGCACA
CCTCCTGTATCACCCTCCAAACTCGGCAACCCTGAGCAGATGCTGAGGGGGCAACCGGCG
CTCCCCAGACCCCCAACGTCAGTGGGGCCTGCTTCCCCGAAGTGTCCAGGAGAGAAGGGG
CAGGGGGCTCCCGCCGAGGCTCCCATCATCCTCAGCTCGCCCCGCACCTCCAAGACAGAC
TCATATGAACTGGTGTGGCGGCCTCGGCATGAGGGCAGTGGCCGGGCGCCAATCCTCTAC
TATGTGGTGAAACACCGCAAGCAGGTCACAAATTCCTCTGACGATTGGACCATCTCTGGC
ATTCCAGCCAACCAGCACCGCCTGACCCTCACCAGACTTGACCCCGGGAGCTTGTATGAA
GTGGAGATGGCAGCTTACAACTGTGCGGGAGAGGGCCAGACAGCCATGGTCACCTTCCGA
ACTGGACGGCGGCCCAAACCCGAGATCATGGCCAGCAAAGAGCAGCAGATCCAGAGAGAC
GACCCTGGAGCCAGTCCCCAGAGCAGCAGCCAGCCAGACCACGGCCGCCTCTCCCCCCCA
GAAGCTCCCGACAGGCCCACCATCTCCACGGCCTCCGAGACCTCAGTGTACGTGACCTGG
ATTCCCCGTGGGAATGGTGGGTTCCCAATCCAGTCCTTCCGTGTGGAGTACAAGAAGCTA
AAGAAAGTGGGAGACTGGATTCTGGCCACCAGCGCCATCCCCCCATCGCGGCTGTCCGTG
GAGATCACGGGCCTAGAGAAAGGCACCTCCTACAAGTTTCGAGTCCGGGCTCTGAACATG
CTGGGGGAGAGCGAGCCCAGCGCCCCTCTCGGCCCTACGTGGTGTCGGGCTACAGCGGT
CGCGTGTACGAGAGGCCCGTGGCAGGTCCTTATATCACCTTCACGGATGCGGTCAATGAG
ACCACCATCATGCTCAAGTGGATGTACATCCCAGCAAGTAACAACAACACCCCAATCCAT
GGCTTTTATATCTATTATCGACCCACAGACAGTGACAATGATAGTGACTACAAGAAGGAT
ATGGTGGAAGGGGACAAGTACTGGCACTCCATCAGCCACCTGCAGCCAGAGACCTCCTAC
GACATTAAGATGCAGTGCTTCAATGAAGGAGGGGAGAGCGAGTTCAGCAACGTGATGATC
TGTGAGACCAAAGCTCGGAAGTCTTCTGGCCAGCCTGGTCGACTGCCACCCCCAACTCTG
GCCCCACCACAGCCGCCCCTTCCTGAAACCATAGAGCGGCCGGTGGGCACTGGGGCCATG
GTGGCTCGCTCCAGCGACCTGCCCTATCTGATTGTCGGGGTCGTCCTGGGCTCCATCGTT
CTCATCATCGTCACCTTCATCCCCTTCTGCTTGTGGAGGGCCTGGTCTAAGCAAAAACAT
ACAACAGACCTGGGTTTTCCTCGAAGTGCCCTTCCACCCTCCTGCCCGTATACTATGGTG
CCATTGGGAGGACTCCCAGGCCACCAGGCCAGTGGACAGCCCTACCTCAGTGGCATCAGT
GGACGGGCCTGTGCTAATGGGATCCACATGAATAGGGGCTGCCCCTCGGCTGCAGTGGGC
TACCCGGGCATGAAGCCCCAGCAGCACTGCCCAGGCGAGCTTCAGCAGCAGAGTGACACC
AGCAGCCTGCTGAGGCAGACCCATCTTGGCAATGGATATGACCCCCAAAGTCACCAGATC
ACGAGGGGTCCCAAGTCTAGCCCGGACGAGGGCTCTTTCTTATACACACTGCCCGACGAC

```
TCCACTCACCAGCTGCTGCAGCCCCATCACGACTGCTGCCAACGCCAGGAGCAGCCTGCT
GCTGTGGGCCAGTCAGGGGTGAGGAGAGCCCCCGACAGTCCTGTCCTGGAAGCAGTGTGG
GACCCTCCATTTCACTCAGGGCCCCATGCTGCTTGGGCCTTGTGCCAGTTGAAGAGGTG
GACAGTCCTGACTCCTGCCAAGTGAGTGGAGGAGACTGGTGTCCCCAGCACCCCGTAGGG
GCCTACGTAGGACAGGAACCTGGAATGCAGCTCTCCCCGGGGCCACTGGTGCGTGTGTCT
TTTGAAACACCACCTCTCACAATTTAGGCAGAAGCTGATATCCCAGAAAGACTATATATT
GTTTTTTTTTAAAAAAAAAAGAAGAAAAAAGAGACAGAGAAAATTGGTATTTATTTTTC
TATTATAGCCATATTTATATATTTATGCACTTGTAAATAAATGTATATGTTTTATAATTC
TGGAGAGACATAAGGAGTCCTACCCGTTGAGGTTGGAGAGGGAAAATAAAGAAGCTGCCA
CCTAACAGGAGTCACCCAGGAAAGCACCGCACAGGCTGGCGCGGGACAGACTCCTAACCT
GGGGCCTCTGCAGTGGCAGGCGAGGCTGCAGGAGGCCCACAGATAAGCTGGCAAGAGGAA
GGATCCCAGGCACATGGTTCATCACGAGCATGAGGGAACAGCAAGGGGCACGGTATCACA
GCCTGGAGACACCCACACAGATGGCTGGATCCGGTGCTACGGGAAACATTTTCCTAAGAT
GCCCATGAGAACAGACCAAGATGTGTACAGCACTATGAGCATTAAAAAACCTTCCAGAAT
CAATAATCCGTGGCAACATATCTCTGTAAAAACAAACACTGTAACTTCTAAATAAATGTT
TAGTCTTCCCTGTAAAA
```

```
ATGGACTTGGCACCTTATTTTACTTCTGAGCCGCTCTCTGCTGTCCAGAAACTTGGTGGACCTGTAGTACTG
CATTGTTCTGCTCAACCTGTGACCACTCGTATCTCATGGCTGCATAACGGAAAAACATTGGATGGAAACCTG
GAACATATTAAGATTCATCAGGGGACTCTGACAATTCTTTCTCTCAACTCCTCTCTTTTGGGTTACTACCAG
TGCCTTGCCAACAATAGCATCGGTGCCATTGTGAGTGGCCCTGCGACAGTATCTGTGGCAGTTCTTGGTGAT
TTTGGTTCATCCACAAAGCATGTTATTACAGCAGAAGAAAAAAGTGCTGGTTTCATTGGCTGCAGGGTACCG
GAGAGTAACCCCAAAGCTGAGGTGCGCTATAAAATCCGGGGAAAATGGCTGGAACATTCCACAGAGAATTAC
TTAATCCTTCCATCAGGAAATCTTCAGATTTTGAATGTATCCTTAGAGGACAAGGGATCATACAAATGTGCA
GCTTATAATCCTGTCACACATCAATTAAAAGTTGAACCTATTGGCCGAAAGCTCCTTGTGAGTCGTCCTTCT
TCAGATGATGTTCACATTCTTCACCCCACCCATTCACAGGCATTAGCTGTTCTTTCTCGTAGCCCTGTAACC
TTGGAGTGTGTGGTGAGTGGGGTCCCGGCTCCTCAAGTGTATTGGCTAAAGGACGGGCAGGACATTGCACCA
GGAAGCAACTGGAGAAGGTTGTATTCTCATCTTGCCACTGATAGCGTTGACCCGGCGGACTCCGGAAACTAT
TCCTGCATGGCGGGAAACAAGTCTGGAGATGTAGAATATGTGACTTACATGGTTAATGTACTTGAACATGCT
TCCATTTCTAAAGGACTACAGGATCAGATAGTGTCTCTGGGTGCCACAGTACACTTTACCTGCGACGTTCAT
GGGAACCCAGCCCCCAACTGTACCTGGTTTCACAATGCACAGCCTATTCATCCTTCTGCACGACATCTAACT
GCAGGAAACGGACTGAAAATCAGTGGGGTTACTGTGGAAGATGTTGGGATGTATCAGTGTGTAGCAGATAAT
GGGATTGGATTTATGCACTCTACTGGAAGACTTGAAATTGAAATGACGGTGGATTCAAGCCAGTTATAATT
ACGGCACCAGTAAGTGCAAAGGTTGCAGACGGAGACTTTGTTACTCTGTCCTGCAATGCCAGTGGGCTGCCG
GTTCCGGTCATTCGTTGGTATGACAGCCATGGATTGATAACCAGCCATCCATCTCAAGTCCTGAGATCGAAA
TCCCGAAAATCACAGTTATCAAGACCTGAGGGCTTGAACCTGGAGCCTGTGTACTTCGTCCTGTCCCAAGCT
GGTGCAAGCTCTCTCCATATTCAGGCTGTGACTCAGGAACATGCGGGGAAATACATCTGCGAAGCTGCAAAT
GAACATGGTACCACACAGGCAGAAGCATCTCTCATGGTTGTTCCTTTTGAAACAAATACAAAAGCAGAGACA
GTCACACTTCCTGATGCTGCTCAGAATGATGACAGAAGTAAGAGAGATGGTTCAGAAACTGGGTTACTGAGC
TCATTTCCGGTGAAGGTCCATCCCAGTGCAGTGGAATCAGCACCAGAGAAAAACGCCAGCGGCATCTCTGTT
CCTGATGCCCCCATCATACTGAGCCCCCACAGACCCACACACCAGACACGTACAACCTGGTGTGGAGGGCA
GGCAAGGATGGTGGGCTGCCCATCAATGCTTACTTTGTGAAGTATCGAAAGCTGGATGATGGGGTTGGCATG
CTGGGAAGCTGGCACACGGTTCGAGTCCCAGGAAGTGAAAATGAGCTCCATTTAGCTGAGCTGGAGCCATCT
AGTCTTTATGAAGTCTTGATGGTAGCAAGAAGCGCAGCAGGTGAAGGCCAACCTGCCATGATTACCTTCCGA
ACCAGCAAAGAAAAAACAGCGTCATCAAAAAACACCCAGGCATCCTCTCCACCCGTGGGCATCCCTAAGTAT
CCCGTTGTTTCAGAGGCTGCAAACAACAATTTTGGAGTGGTACTTACAGATTCCTCTAGGCACAGTGGAGTT
CCAGAGGCACCAGATCGGCCTACCATCTCCACTGCATCAGAGACATCAGTCTATGTCACTTGGATTCCTCGG
GCAAACGGGGGTTCTCCAATCACTGCCTTCAAAGTCGAATATAAACGGATGAGGACCAGCAATTGGCTGGTG
GCAGCTGAAGACATCCCTCCTTCCAAACTTTCAGTGGAAGTTCGTAGTTTAGAACCAGGTTCAACATACAAA
TTTAGGGTCATTGCCATCAACCATTATGGTGAGAGTTTTCGGAGTTCAGCATCTCGTCCTTATCAAGTGGTT
GGGTTCCCCAATCGCTTTTCCAGCCGTCCAATAACTGGACCTCACATTGCATACACAGAGGCTGTCAGCGAT
ACTCAGATCATGCTAAAGTGGACGTACATTCCATCAAGATACAATAACACTCCCATTCAAGGATTTTATATC
TATTACCGACCAACAGATAGTGACAATGACAGTGATTACAAGAGGGATGTTGTAGAAGGTTCAAAGCAGTGG
CACATGATTGGCCACCTGCAGCCAGAAACCTCCTATGACATTAAAATGCAATGCTTCAATGAAGGAGGAGAA
AGTGAATTTAGCAATGTGATGATCTGCGAGACTAAAGTGAAACGTGTTCCTGGAGCTTCTGAATATCCTGTC
AAAGACTTGAGTACCCCTCCAAATTCTTTGGGAAGTGGAGGAAATGTGGGGCCTGCAACCAGCCCTGCCAGA
AGCAGTGACATGTTATATCTGATCGTTGGCTGTGTGCTGGGCGTCATGGTCCTCATTCTGATGGTTTTCATT
GCAATGTGCCTGTGGAAGAATCGCCAGCAGAATACCATACAAAAATATGACCCACCAGGATATCTCTACCAA
GGATCAGATATGAACGGGCAGATGGTGGACTACACCACTCTCTCAGGAGCAAGTCAGATAAATGGAAATGTT
CACGGAGGCTTCCTAACCAATGGCGGTCTCAGCAGTGGCTATTCCCACCTTCACCATAAGGTCCCCAATGCA
GTCAATGGAATTGTGAATGGGAGCCTAAATGGAGGGCTTTACTCCGGGCACAGCAACTCTCTAACCAGGACA
CACGTGGATTTTGAACATCCTCATCATCTAGTGAATGGTGGTGGAATGTACACGGCCGTGCCTCAGATTGAC
CCTCTGGAGTGTGTTAACTGCCGAAATTGTCGAAACAACAATAGGTGTTTCACCAAAACCAACAGCACTTTC
AGCAGCAGCCCTCCTCCTGTGGTCCCTGTGGTAGCACCTTATCCTCAGGATGGTTTGGAAATGAAGCCCCTC
AGTCACGTGAAGGTGCCTGTATGCCTGACTTCCGCAGTCCCTGATTGTGGCCAGTTGCCGGAGGAGAGCGTC
AAGGACAATGTGGAACCAGTCCCTACTCAGCGTACCTGCTGTCAGGACATTGTAAATGACGTCAGCTCTGAT
GGCTCAGAAGATCCAGCAGAGTTCAGCAGAGGAGACAGCTGTGCCCATTCAGAAACAGAGATCAACATTGTA
AGTTGGAATGCTCTTATTTTGCCACCTGTCCCCGAGGGCTGTGCTGAGAAGACAATGTGGTCTCCACCTGGC
ATTCCTTTAGACAGCCCGACAGAGGTCCTTCAGCAGCCCGGGAAACCTGAGGACATGCAAACAACCAGTCA
TGTTCCAACTTCAAGCCGGTAACTGCACACAACAGGCTCGGGAGCGAACTGTGTGAAGGACCTTAATTCAAA
TCAGAGAAAATCATTATTTATTTTTTTGTAGTAGTAATGTCATATGAATGTATCTTAAAACGTGTGCCCTTT
TATATTATTTATGCCTTAAATGTTTTCTTCCCCATTCCTTCCTCCCCCTCGGTAGGAAACAACCTTGTTTTG
CATAGTATTCAGTCACCTGGAGGGCA
```

FIGURE 2A

```
MLRGTMTAWRGMRPEVTLACLLLATAGCFADLNEVPQVTVQPASTVQKPGGTVILGCVVEPPRMNVTWRLNG
KELNGSDDALGVLITHGTLVITALNNHTVGRYQCVARMPAGAVASVPATVTLANLQDFKLDVQHVIEVDEGN
TAVIACHLPESHPKAQVRYSVKQEWLEASRGNYLIMPSGNLQIVNASQEDEGMYKCAAYNPVTQEVKTSGSS
DRLRVRRSTAEAARIIYPPEAQTIIVTKGQSLILECVASGIPPPRVTWAKDGSSVTGYNKTRFLLSNLLIDT
TSEEDSGTYRCMADNGVGQPGAAVILYNVQVFEPPEVTMELSQLVIPWGQSAKLTCEVRGNPPPSVLWLRNA
VPLISSQRLRLSRRALRVLSMGPEDEGVYQCMAENEVGSAHAVVQLRTSRPSITPRLWQDAELATGTPPVSP
SKLGNPEQMLRGQPALPRPPTSVGPASPKCPGEKGQGAPAEAPIILSSPRTSKTDSYELVVWRPRHEGSGRAP
ILYYVVKHRKQVTNSSDDWTISGIPANQHRLTLTRLDPGSLYEVEMAAYNCAGEGQTAMVTFRTGRRPKPEI
MASKEQQIQRDDPGASPQSSSQPDHGRLSPPEAPDRPTISTASETSVYVTWIPRGNGGFPIQSFRVEYKKLK
KVGDWILATSAIPPSRLSVEITGLEKGTSYKFRVRALNMLGESEPSAPSRPYVVSGYSGRVYERPVAGPYIT
FTDAVNETTIMLKWMYIPASNNNTPIHGFYIYYRPTDSDNDSDYKKDMVEGDKYWHSISHLQPETSYDIKMQ
CFNEGGESEFSNVMICETKARKSSGQPGRLPPPTLAPPQPPLPETIERPVGTGAMVARSSDLPYLIVGVVLG
SIVLIIVTFIPFCLWRAWSKQKHTTDLGFPRSALPPSCPYTMVPLGGLPGHQASGQPYLSGISGRACANGIH
MNRGCPSAAVGYPGMKPQQHCPGELQQQSDTSSLLRQTHLGNGYDPQSHQITRGPKSSPDEGSFLYTLPDDS
THQLLQPHHDCCQRQEQPAAVGQSGVRRAPDSPVLEAVWDPPFHSGPPCCLGLVPVEEVDSPDSCQVSGGDW
CPQHPVGAYVGQEPGMQLSPGPLVRVSFETPPLTI
```

Signal peptide:
amino acids 1-30

Transmembrane domain:
amino acids 16-30 (type II), 854-879.

Transmembrane domain:
842-862

Signal sequence
1 30

Immunoglobulin domain
50 108
143-202
245-301
337-393

Immunoglobulin I-set domain
36-125
229-318
323-409

Fibronectin type III domain
471-562
607-694
713-803

Immunoglobulin V-set domain
129-222
228-315
324-407

Cytochrome P450 cysteine heme-iron ligand signature
1051-1061

N-6 Adenine-specific DNA methylases signature
1045-1052

Figure 2B

```
MDLAPYFTSEPLSAVQKLGGPVVLHCSAQPVTTRISWLHNGKTLDGNLEHIKIHQGTLTILSLNSSLL
GYYQCLANNSIGAIVSGPATVSVAVLGDFGSSTKHVITAEEKSAGFIGCRVPESNPKAEVRYKIRGKW
LEHSTENYLILPSGNLQILNVSLEDKGSYKCAAYNPVTHQLKVEPIGRKLLVSRPSSDDVHILHPTHS
QALAVLSRSPVLECVVSGVPAPQVYWLKDGQDIAPGSNWRRLYSHLATDSVDPADSGNYSCMAGNKSG
DVEYVTYMVNVLEHASISKGLQDQIVSLGATVHFTCDVHGNPAPNCTWFHNAQPIHPSARHLTAGNGL
KISGVTVEDVGMYQCVADNGIGFMHSTGRLEIENDGGFKPVIITAPVSAKVADGDFVTLSCNASGLPV
PVIRWYDSHGLITSHPSQVLRSKSRKSQLSRPEGLNLEPVYFVLSQAGASSLHIQAVTQEHAGKYICE
AANEHGTTQAEASLMVVPFETNTKAETVTLPDAAQNDDRSKRDGSETGLLSSFPVKVHPSAVESAPEK
NASGISVPDAPIILSPPQTHTPDTYNLVWRAGKDGGLPINAYFVKYRKLDDGVGMLGSWHTVRVPGSE
NELHLAELEPSSLYEVLMVARSAAGEGQPAMITFRTSKEKTASSKNTQASSPPVGIPKYPVVSEAANN
NFGVVLTDSSRHSGVPEAPDRPTISTASETSVYVTWIPRANGGSPITAFKVEYKRMRTSNWLVAAEDI
PPSKLSVEVRSLEPGSTYKFRVIAINHYGESFRSSASRPYQVVGFPNRFSSRPITGPHIAYTEAVSDT
QIMLKWTYIPSSNNNTPIQGFYIYYRPTDSDNDSDYKRDVVEGSKQWHMIGHLQPETSYDIKMQCFNE
GGESEFSNVMICETKVKRVPGASEYPVKDLSTPPNSLGSGGNVGPATSPARSSDMLYLIVGCVLGVMV
LILMVFIAMCLWKNRQQNTIQKYDPPGYLYQGSDMNGQMVDYTTLSGASQINGNVHGGFLTNGGLSSG
YSHLHHKVPNAVNGIVNGSLNGGLYSGHSNSLTRTHVDFEHPHHLVNGGGMYTAVPQIDPLECVNCRN
CRNNNRCFTKTNSTFSSSPPPVVPVVAPYPQDGLEMKPLSHVKVPVCLTSAVPDCGQLPEESVKDNVE
PVPTQRTCCQDIVNDVSSDGSEDPAEFSRGDSCAHSETEINIVSWNALILPPVPEGCAEKTMWSPPGI
PLDSPTEVLQQPRET
```

Immunoglobulin domain
19-75
110-169
212-268
302-358
395-478

Fibronectin type III domain
553-643
697-783
799-892

Immunoglobulin I-set domain
5-94
196-285
288-374
381-494

Immunoglobulin V-set domain
96-189
281-374
381-494

Immunoglobulin C1-set domain
204-279

PAAR Motif
941-961

Immuno Tyrosine Inhibition Motif (ITIM)
972-992

Cell attachment sequence (RGD)
1186-1189

Transmembrane domain
841-861

SEQUENCE LISTING

<160> NUMBER OF SEQ ID NOS: 4

<210> SEQ ID NO 1
<211> LENGTH: 4277
<212> TYPE: DNA
<213> ORGANISM: Homo sapiens

<400> SEQUENCE: 1

```
gtttctcata gttggcgtct tctaaaggaa aaacactaaa atgaggaact           50
cagcggaccg ggagcgacgc agcttgaggg aagcatccct agctgttggc          100
gcagaggggc gaggctgaag ccgagtggcc cgaggtgtct gaggggctgg          150
```

| | |
|---|---|
| ggcaaaggtg aaagagtttc agaacaagct tcctggaacc catgacccat | 200 |
| gaagtcttgt cgacatttat accgtctgag ggtagcagct cgaaactaga | 250 |
| agaagtggag tgttgccagg gacggcagta tctctttgtg tgaccctggc | 300 |
| ggcctatggg acgttggctt cagacctttg tgatacacca tgctgcgtgg | 350 |
| gacgatgacg gcgtggagag gaatgaggcc tgaggtcaca ctggcttgcc | 400 |
| tcctcctagc cacagcaggc tgctttgctg acttgaacga ggtccctcag | 450 |
| gtcaccgtcc agcctgcgtc caccgtccag aagcccggag gcactgtgat | 500 |
| cttgggctgc gtggtggaac ctccaaggat gaatgtaacc tggcgcctga | 550 |
| atggaaagga gctgaatggc tcggatgatg ctctgggtgt cctcatcacc | 600 |
| cacgggaccc tcgtcatcac tgcccttaac aaccacactg tgggacggta | 650 |
| ccagtgtgtg gcccggatgc ctgcgggggc tgtggccagc gtgccagcca | 700 |
| ctgtgacact agccaatctc caggacttca agttagatgt gcagcacgtg | 750 |
| attgaagtgg atgagggaaa cacagcagtc attgcctgcc acctgcctga | 800 |
| gagccacccc aaagcccagg tccggtacag cgtcaaacaa gagtggctgg | 850 |
| aggcctccag aggtaactac ctgatcatgc cctcagggaa cctccagatt | 900 |
| gtgaatgcca gccaggagga cgagggcatg tacaagtgtg cagcctacaa | 950 |
| cccagtgacc caggaagtga aaacctccgg ctccagcgac aggctacgtg | 1000 |
| tgcgccgctc caccgctgag gctgcccgca tcatctaccc cccagaggcc | 1050 |
| caaaccatca tcgtcaccaa aggccagagt ctcattctgg agtgtgtggc | 1100 |
| cagtggaatc ccaccccac gggtcacctg ggccaaggat gggtccagtg | 1150 |
| tcaccggcta caacaagacg cgcttcctgc tgagcaacct cctcatcgac | 1200 |
| accaccagcg aggaggactc aggcacctac cgctgcatgg ccgacaatgg | 1250 |
| ggttgggcag cccgggcag cggtcatcct ctacaatgtc caggtgtttg | 1300 |
| aaccccctga ggtcaccatg gagctatccc agctggtcat cccctggggc | 1350 |
| cagagtgcca agcttacctg tgaggtgcgt gggaaccccc cgccctccgt | 1400 |
| gctgtggctg aggaatgctg tgcccctcat ctccagccag cgcctccggc | 1450 |
| tctcccgcag ggccctgcgc gtgctcagca tggggcctga ggacgaaggc | 1500 |
| gtctaccagt gcatggccga gaacgaggtt gggagcgccc atgccgtagt | 1550 |
| ccagctgcgg acctccaggc caagcataac cccaaggcta tggcaggatg | 1600 |
| ctgagctggc tactggcaca cctcctgtat caccctccaa actcggcaac | 1650 |
| cctgagcaga tgctgagggg gcaaccggcg ctccccagac ccccaacgtc | 1700 |
| agtggggcct gcttccccga agtgtccagg agagaagggg caggggctc | 1750 |
| ccgccgaggc tccatcatc ctcagctcgc cccgcacctc caagacagac | 1800 |
| tcatatgaac tggtgtggcg gcctcggcat gagggcagtg gccggcgcc | 1850 |
| aatcctctac tatgtggtga aacaccgcaa gcaggtcaca aattcctctg | 1900 |
| acgattggac catctctggc attccagcca accagcaccg cctgacccctc | 1950 |
| accagacttg accccgggag cttgtatgaa gtggagatgg cagcttacaa | 2000 |
| ctgtgcggga gagggccaga cagccatggt caccttccga actggacggc | 2050 |
| ggcccaaacc cgagatcatg gccagcaaag agcagcagat ccagagagac | 2100 |
| gaccctggag ccagtcccca gagcagcagc cagccagacc acggccgcct | 2150 |

-continued

| | |
|---|---|
| ctccccccca gaagctcccg acaggcccac catctccacg gcctccgaga | 2200 |
| cctcagtgta cgtgacctgg attccccgtg ggaatggtgg gttcccaatc | 2250 |
| cagtccttcc gtgtggagta caagaagcta aagaaagtgg gagactggat | 2300 |
| tctggccacc agcgccatcc ccccatcgcg gctgtccgtg gagatcacgg | 2350 |
| gcctagagaa aggcacctcc tacaagtttc gagtccgggc tctgaacatg | 2400 |
| ctgggggaga gcgagcccag cgccccctct cggccctacg tggtgtcggg | 2450 |
| ctacagcggt cgcgtgtacg agaggcccgt ggcaggtcct tatatcacct | 2500 |
| tcacggatgc ggtcaatgag accaccatca tgctcaagtg gatgtacatc | 2550 |
| ccagcaagta acaacaacac cccaatccat ggctttata tctattatcg | 2600 |
| acccacagac agtgacaatg atagtgacta caagaaggat atggtggaag | 2650 |
| gggacaagta ctggcactcc atcagccacc tgcagccaga gacctcctac | 2700 |
| gacattaaga tgcagtgctt caatgaagga ggggagagcg agttcagcaa | 2750 |
| cgtgatgatc tgtgagacca aagctcggaa gtcttctggc cagcctggtc | 2800 |
| gactgccacc cccaactctg gccccaccac agccgcccct tcctgaaacc | 2850 |
| atagagcggc cggtgggcac tggggccatg gtggctcgct ccagcgacct | 2900 |
| gccctatctg attgtcgggg tcgtcctggg ctccatcgtt ctcatcatcg | 2950 |
| tcaccttcat ccccttctgc ttgtggaggg cctggtctaa gcaaaaacat | 3000 |
| acaacagacc tgggttttcc tcgaagtgcc cttccaccct cctgcccgta | 3050 |
| tactatggtg ccattgggag gactcccagg ccaccaggcc agtggacagc | 3100 |
| cctacctcag tggcatcagt ggacgggcct gtgctaatgg gatccacatg | 3150 |
| aatagggggct gccccctcggc tgcagtgggc tacccgggca tgaagcccca | 3200 |
| gcagcactgc ccaggcgagc ttcagcagca gagtgacacc agcagcctgc | 3250 |
| tgaggcagac ccatcttggc aatggatatg accccaaaag tcaccagatc | 3300 |
| acgagggtc ccaagtctag cccggacgag ggctctttct tatacacact | 3350 |
| gccccgacgac tccactcacc agctgctgca gcccatcac gactgctgcc | 3400 |
| aacgccagga gcagcctgct gctgtgggcc agtcaggggt gaggagagcc | 3450 |
| cccgacagtc ctgtcctgga agcagtgtgg gaccctccat ttcactcagg | 3500 |
| gcccccatgc tgcttgggcc ttgtgccagt tgaagaggtg gacagtcctg | 3550 |
| actcctgcca agtgagtgga ggagactggt gtccccagca ccccgtaggg | 3600 |
| gcctacgtag gacaggaacc tggaatgcag ctctccccgg ggccactggt | 3650 |
| gcgtgtgtct tttgaaacac cacctctcac aatttaggca gaagctgata | 3700 |
| tcccagaaag actatatatt gttttttttt taaaaaaaaa agaagaaaaa | 3750 |
| agagacagag aaaattggta tttatttttc tattatagcc atatttatat | 3800 |
| atttatgcac ttgtaaataa atgtatatgt tttataattc tggagagaca | 3850 |
| taaggagtcc tacccgttga ggttggagag ggaaaataaa gaagctgcca | 3900 |
| cctaacagga gtcacccagg aaagcaccgc acaggctggc gcgggacaga | 3950 |
| ctcctaacct ggggcctctg cagtggcagg cgaggctgca ggaggcccac | 4000 |
| agataagctg gcaagaggaa ggatcccagg cacatggttc atcacagagca | 4050 |
| tgagggaaca gcaaggggca cggtatcaca gcctggagac acccacacag | 4100 |

```
atggctggat ccggtgctac gggaaacatt ttcctaagat gcccatgaga              4150
acagaccaag atgtgtacag cactatgagc attaaaaaac cttccagaat              4200
caataatccg tggcaacata tctctgtaaa aacaaacact gtaacttcta              4250
aataaatgtt tagtcttccc  tgtaaaa                                      4277

<210> SEQ ID NO 2
<211> LENGTH: 3986
<212> TYPE: DNA
<213> ORGANISM: Homo sapiens

<400> SEQUENCE: 2
atggacttgg caccttattt tacttctgag ccgctctctg ctgtccagaa                50
acttggtgga cctgtagtac tgcattgttc tgctcaacct gtgaccactc               100
gtatctcatg gctgcataac ggaaaaacat tggatggaaa cctggaacat               150
attaagattc atcagggggac tctgacaatt ctttctctca actcctctct              200
tttgggttac taccagtgcc ttgccaacaa tagcatcggt gccattgtga               250
gtggccctgc gacagtatct gtggcagttc ttggtgattt tggttcatcc               300
acaaagcatg ttattacagc agaagaaaaa agtgctggtt tcattggctg               350
cagggtaccg gagagtaacc ccaaagctga ggtgcgctat aaaatccggg               400
gaaaatggct ggaacattcc acagagaatt acttaatcct tccatcagga               450
aatcttcaga ttttgaatgt atccttagag gacaagggga catacaaatg               500
tgcagcttat aatcctgtca cacatcaatt aaaagttgaa cctattggcc               550
gaaagctcct tgtgagtcgt ccttcttcag atgatgttca cattcttcac               600
cccacccatt cacaggcatt agctgttctt tctcgtagcc ctgtaacctt               650
ggagtgtgtg gtgagtgggg tcccggctcc tcaagtgtat tggctaaagg               700
acgggcagga cattgcacca ggaagcaact ggagaaggtt gtattctcat               750
cttgccactg atagcgttga cccggcggac tccggaaact attcctgcat               800
ggcgggaaac aagtctggag atgtagaata tgtgacttac atggttaatg               850
tacttgaaca tgcttccatt tctaaaggac tacaggatca gatagtgtct               900
ctgggtgcca cagtacactt tacctgcgac gttcatggga acccagcccc               950
caactgtacc tggtttcaca atgcacagcc tattcatcct tctgcacgac              1000
atctaactgc aggaaacgga ctgaaaatca gtggggttac tgtggaagat              1050
gttgggatgt atcagtgtgt agcagataat gggattggat ttatgcactc              1100
tactggaaga cttgaaattg aaaatgacgg tggattcaag ccagttataa              1150
ttacggcacc agtaagtgca aaggttgcag acggagactt tgttactctg              1200
tcctgcaatg ccagtgggct gccggttccg gtcattcgtt ggtatgacag              1250
ccatggattg ataaccagcc atccatctca agtcctgaga tcgaaatccc              1300
gaaaatcaca gttatcaaga cctgagggct tgaacctgga gcctgtgtac              1350
ttcgtcctgt cccaagctgg tgcaagctct ctccatattc aggctgtgac              1400
tcaggaacat gcggggaaat acatctgcga agctgcaaat gaacatggta              1450
ccacacaggc agaagcatct ctcatggttg ttcctttga aacaaataca              1500 aaagcagaga cagtcacact tcctgatgct gctcagaatg atgacagaag              1550
taagagagat ggttcagaaa ctgggttact gagctcattt ccggtgaagg              1600
```

| | |
|---|---|
| tccatcccag tgcagtggaa tcagcaccag agaaaaacgc cagcggcatc | 1650 |
| tctgttcctg atgcccccat catactgagc ccccacagaa cccacacacc | 1700 |
| agacacgtac aacctggtgt ggagggcagg caaggatggt gggctgccca | 1750 |
| tcaatgctta ctttgtgaag tatcgaaagc tggatgatgg ggttggcatg | 1800 |
| ctgggaagct ggcacacggt tcgagtccca ggaagtgaaa atgagctcca | 1850 |
| tttagctgag ctggagccat ctagtcttta tgaagtcttg atggtagcaa | 1900 |
| gaagcgcagc aggtgaaggc caacctgcca tgattacctt ccgaaccagc | 1950 |
| aaagaaaaaa cagcgtcatc aaaaaacacc caggcatcct ctccacccgt | 2000 |
| gggcatccct aagtatcccg ttgtttcaga ggctgcaaac aacaattttg | 2050 |
| gagtggtact tacagattcc tctaggcaca gtggagttcc agaggcacca | 2100 |
| gatcggccta ccatctccac tgcatcagag acatcagtct atgtcacttg | 2150 |
| gattcctcgg gcaaacgggg gttctccaat cactgccttc aaagtcgaat | 2200 |
| ataaacggat gaggaccagc aattggctgg tggcagctga agacatccct | 2250 |
| ccttccaaac tttcagtgga agttcgtagt ttagaaccag gttcaacata | 2300 |
| caaatttagg gtcattgcca tcaaccatta tggtgagagt tttcggagtt | 2350 |
| cagcatctcg tccttatcaa gtggttgggt tccccaatcg cttttccagc | 2400 |
| cgtccaataa ctggacctca cattgcatac acagaggctg tcagcgatac | 2450 |
| tcagatcatg ctaaagtgga cgtacattcc atcaagtaac aataacactc | 2500 |
| ccattcaagg attttatatc tattaccgac caacagatag tgacaatgac | 2550 |
| agtgattaca agagggatgt tgtagaaggt tcaaagcagt ggcacatgat | 2600 |
| tggccacctg cagccagaaa cctcctatga cattaaaatg caatgcttca | 2650 |
| atgaaggagg agaaagtgaa tttagcaatg tgatgatctg cgagactaaa | 2700 |
| gtgaaacgtg ttcctggagc ttctgaatat cctgtcaaag acttgagtac | 2750 |
| ccctccaaat tctttgggaa gtggaggaaa tgtggggcct gcaaccagcc | 2800 |
| ctgccagaag cagtgacatg ttatatctga tcgttggctg tgtgctgggc | 2850 |
| gtcatggtcc tcattctgat ggttttcatt gcaatgtgcc tgtggaagaa | 2900 |
| tcgccagcag aataccatac aaaaatatga cccaccagga tatctctacc | 2950 |
| aaggatcaga tatgaacggg cagatggtgg actacaccac tctctcagga | 3000 |
| gcaagtcaga taaatggaaa tgttcacgga ggcttcctaa ccaatggcgg | 3050 |
| tctcagcagt ggctattccc accttcacca taaggtcccc aatgcagtca | 3100 |
| atggaattgt gaatgggagc ctaaatggag ggctttactc cgggcacagc | 3150 |
| aactctctaa ccaggacaca cgtggatttt gaacatcctc atcatctagt | 3200 |
| gaatggtggt ggaatgtaca cggccgtgcc tcagattgac cctctggagt | 3250 |
| gtgttaactg ccgaaattgt cgaaacaaca ataggtgttt caccaaaaacc | 3300 |
| aacagcactt tcagcagcag ccctcctcct gtggtccctg tggtagcacc | 3350 |
| ttatcctcag gatggtttgg aaatgaagcc cctcagtcac gtgaaggtgc | 3400 |
| ctgtatgcct gacttccgca gtccctgatt gtggccagtt gccggaggag | 3450 |
| agcgtcaagg acaatgtgga accagtccct actcagcgta cctgctgtca | 3500 |
| ggacattgta aatgacgtca gctctgatgg ctcagaagat ccagcagagt | 3550 |

-continued

```
tcagcagagg agacagctgt gcccattcag aaacagagat caacattgta    3600
agttggaatg ctcttatttt gccacctgtc cccgagggct gtgctgagaa    3650
gacaatgtgg tctccacctg gcattccttt agacagcccg acagaggtcc    3700
ttcagcagcc ccgggaaacc tgaggacatg caaacaacca gtcatgttcc    3750
aacttcaagc cggtaactgc acacaacagg cctgggagcg aactgtgtga    3800
aggaccttaa ttcaaatcag agaaaatcat tatttatttt tttgtagtag    3850
taatgtcata tgaatgtatc ttaaaacgtg tgcccttttta tattatttat   3900 gccttaaatg ttttcttccc cattccttcc tcccccctcgg taggaaacaa   3950 ccttgttttg catagtattc agtcacctgg   agggca                 3986
```

<210> SEQ ID NO 3
<211> LENGTH: 1115
<212> TYPE: PRT
<213> ORGANISM: Homo sapiens

<400> SEQUENCE: 3

```
Met Leu Arg Gly Thr Met Thr Ala Trp Arg Gly Met Arg Pro Glu
 1               5                  10                  15

Val Thr Leu Ala Cys Leu Leu Leu Ala Thr Gly Cys Phe Ala
                20                  25                  30

Asp Leu Asn Glu Val Pro Gln Val Thr Val Gln Pro Ala Ser Thr
                35                  40                  45

Val Gln Lys Pro Gly Gly Thr Val Ile Leu Gly Cys Val Val Glu
                50                  55                  60

Pro Pro Arg Met Asn Val Thr Trp Arg Leu Asn Gly Lys Glu Leu
                65                  70                  75

Asn Gly Ser Asp Asp Ala Leu Gly Val Leu Ile Thr His Gly Thr
                80                  85                  90

Leu Val Ile Thr Ala Leu Asn Asn His Thr Val Gly Arg Tyr Gln
                95                 100                 105

Cys Val Ala Arg Met Pro Ala Gly Ala Val Ala Ser Val Pro Ala
               110                 115                 120

Thr Val Thr Leu Ala Asn Leu Gln Asp Phe Lys Leu Asp Val Gln
               125                 130                 135

His Val Ile Glu Val Asp Glu Gly Asn Thr Ala Val Ile Ala Cys
               140                 145                 150

His Leu Pro Glu Ser His Pro Lys Ala Gln Val Arg Tyr Ser Val
               155                 160                 165

Lys Gln Glu Trp Leu Glu Ala Ser Arg Gly Asn Tyr Leu Ile Met
               170                 175                 180

Pro Ser Gly Asn Leu Gln Ile Val Asn Ala Ser Gln Glu Asp Glu
               185                 190                 195

Gly Met Tyr Lys Cys Ala Ala Tyr Asn Pro Val Thr Gln Glu Val
               200                 205                 210

Lys Thr Ser Gly Ser Ser Asp Arg Leu Arg Val Arg Arg Ser Thr
               215                 220                 225

Ala Glu Ala Ala Arg Ile Ile Tyr Pro Pro Glu Ala Gln Thr Ile
               230                 235                 240

Ile Val Thr Lys Gly Gln Ser Leu Ile Leu Glu Cys Val Ala Ser
               245                 250                 255

Gly Ile Pro Pro Pro Arg Val Thr Trp Ala Lys Asp Gly Ser Ser
               260                 265                 270
```

```
Val Thr Gly Tyr Asn Lys Thr Arg Phe Leu Leu Ser Asn Leu Leu
                275                 280                 285

Ile Asp Thr Thr Ser Glu Glu Asp Ser Gly Thr Tyr Arg Cys Met
                290                 295                 300

Ala Asp Asn Gly Val Gly Gln Pro Gly Ala Ala Val Ile Leu Tyr
                305                 310                 315

Asn Val Gln Val Phe Glu Pro Pro Glu Val Thr Met Glu Leu Ser
                320                 325                 330

Gln Leu Val Ile Pro Trp Gly Gln Ser Ala Lys Leu Thr Cys Glu
                335                 340                 345

Val Arg Gly Asn Pro Pro Ser Val Leu Trp Leu Arg Asn Ala
                350                 355                 360

Val Pro Leu Ile Ser Ser Gln Arg Leu Arg Leu Ser Arg Arg Ala
                365                 370                 375

Leu Arg Val Leu Ser Met Gly Pro Glu Asp Glu Gly Val Tyr Gln
                380                 385                 390

Cys Met Ala Glu Asn Glu Val Gly Ser Ala His Ala Val Val Gln
                395                 400                 405

Leu Arg Thr Ser Arg Pro Ser Ile Thr Pro Arg Leu Trp Gln Asp
                410                 415                 420

Ala Glu Leu Ala Thr Gly Thr Pro Pro Val Ser Pro Ser Lys Leu
                425                 430                 435

Gly Asn Pro Glu Gln Met Leu Arg Gly Gln Pro Ala Leu Pro Arg
                440                 445                 450

Pro Pro Thr Ser Val Gly Pro Ala Ser Pro Lys Cys Pro Gly Glu
                455                 460                 465

Lys Gly Gln Gly Ala Pro Ala Glu Ala Pro Ile Ile Leu Ser Ser
                470                 475                 480

Pro Arg Thr Ser Lys Thr Asp Ser Tyr Glu Leu Val Trp Arg Pro
                485                 490                 495

Arg His Glu Gly Ser Gly Arg Ala Pro Ile Leu Tyr Tyr Val Val
                500                 505                 510

Lys His Arg Lys Gln Val Thr Asn Ser Ser Asp Trp Thr Ile
                515                 520                 525

Ser Gly Ile Pro Ala Asn Gln His Arg Leu Thr Leu Thr Arg Leu
                530                 535                 540

Asp Pro Gly Ser Leu Tyr Glu Val Glu Met Ala Ala Tyr Asn Cys
                545                 550                 555

Ala Gly Glu Gly Gln Thr Ala Met Val Thr Phe Arg Thr Gly Arg
                560                 565                 570

Arg Pro Lys Pro Glu Ile Met Ala Ser Lys Glu Gln Gln Ile Gln
                575                 580                 585

Arg Asp Asp Pro Gly Ala Ser Pro Gln Ser Ser Ser Gln Pro Asp
                590                 595                 600

His Gly Arg Leu Ser Pro Pro Glu Ala Pro Asp Arg Pro Thr Ile
                605                 610                 615

Ser Thr Ala Ser Glu Thr Ser Val Tyr Val Thr Trp Ile Pro Arg
                620                 625                 630

Gly Asn Gly Gly Phe Pro Ile Gln Ser Phe Arg Val Glu Tyr Lys
                635                 640                 645

Lys Leu Lys Lys Val Gly Asp Trp Ile Leu Ala Thr Ser Ala Ile
                650                 655                 660
```

-continued

```
Pro Pro Ser Arg Leu Ser Val Glu Ile Thr Gly Leu Glu Lys Gly
            665                 670                 675

Thr Ser Tyr Lys Phe Arg Val Arg Ala Leu Asn Met Leu Gly Glu
            680                 685                 690

Ser Glu Pro Ser Ala Pro Ser Arg Pro Tyr Val Val Ser Gly Tyr
            695                 700                 705

Ser Gly Arg Val Tyr Glu Arg Pro Val Ala Gly Pro Tyr Ile Thr
            710                 715                 720

Phe Thr Asp Ala Val Asn Glu Thr Thr Ile Met Leu Lys Trp Met
            725                 730                 735

Tyr Ile Pro Ala Ser Asn Asn Thr Pro Ile His Gly Phe Tyr
            740                 745                 750

Ile Tyr Tyr Arg Pro Thr Asp Ser Asp Asn Asp Ser Asp Tyr Lys
            755                 760                 765

Lys Asp Met Val Glu Gly Asp Lys Tyr Trp His Ser Ile Ser His
            770                 775                 780

Leu Gln Pro Glu Thr Ser Tyr Asp Ile Lys Met Gln Cys Phe Asn
            785                 790                 795

Glu Gly Gly Glu Ser Glu Phe Ser Asn Val Met Ile Cys Glu Thr
            800                 805                 810

Lys Ala Arg Lys Ser Ser Gly Gln Pro Gly Arg Leu Pro Pro Pro
            815                 820                 825

Thr Leu Ala Pro Pro Gln Pro Leu Pro Glu Thr Ile Glu Arg
            830                 835                 840

Pro Val Gly Thr Gly Ala Met Val Ala Arg Ser Ser Asp Leu Pro
            845                 850                 855

Tyr Leu Ile Val Gly Val Val Leu Gly Ser Ile Val Leu Ile Ile
            860                 865                 870

Val Thr Phe Ile Pro Phe Cys Leu Trp Arg Ala Trp Ser Lys Gln
            875                 880                 885

Lys His Thr Thr Asp Leu Gly Phe Pro Arg Ser Ala Leu Pro Pro
            890                 895                 900

Ser Cys Pro Tyr Thr Met Val Pro Leu Gly Gly Leu Pro Gly His
            905                 910                 915

Gln Ala Ser Gly Gln Pro Tyr Leu Ser Gly Ile Ser Gly Arg Ala
            920                 925                 930

Cys Ala Asn Gly Ile His Met Asn Arg Gly Cys Pro Ser Ala Ala
            935                 940                 945

Val Gly Tyr Pro Gly Met Lys Pro Gln Gln His Cys Pro Gly Glu
            950                 955                 960

Leu Gln Gln Gln Ser Asp Thr Ser Ser Leu Leu Arg Gln Thr His
            965                 970                 975

Leu Gly Asn Gly Tyr Asp Pro Gln Ser His Gln Ile Thr Arg Gly
            980                 985                 990

Pro Lys Ser Ser Pro Asp Glu Gly Ser Phe Leu Tyr Thr Leu Pro
            995                 1000                1005

Asp Asp Ser Thr His Gln Leu Leu Gln Pro His His Asp Cys Cys
            1010                1015                1020

Gln Arg Gln Glu Gln Pro Ala Ala Val Gly Gln Ser Gly Val Arg
            1025                1030                1035

Arg Ala Pro Asp Ser Pro Val Leu Glu Ala Val Trp Asp Pro Pro
            1040                1045                1050

Phe His Ser Gly Pro Pro Cys Cys Leu Gly Leu Val Pro Val Glu
```

```
                  1055                1060                1065

Glu Val Asp Ser Pro Asp Ser Cys Gln Val Ser Gly Gly Asp Trp
            1070                1075                1080

Cys Pro Gln His Pro Val Gly Ala Tyr Val Gly Gln Glu Pro Gly
            1085                1090                1095

Met Gln Leu Ser Pro Gly Pro Leu Val Arg Val Ser Phe Glu Thr
            1100                1105                1110

Pro Pro Leu Thr Ile
            1115

<210> SEQ ID NO 4
<211> LENGTH: 1239
<212> TYPE: PRT
<213> ORGANISM: Homo sapiens

<400> SEQUENCE: 4

Met Asp Leu Ala Pro Tyr Phe Thr Ser Glu Pro Leu Ser Ala Val
  1               5                  10                  15

Gln Lys Leu Gly Gly Pro Val Val Leu His Cys Ser Ala Gln Pro
                 20                  25                  30

Val Thr Thr Arg Ile Ser Trp Leu His Asn Gly Lys Thr Leu Asp
                 35                  40                  45

Gly Asn Leu Glu His Ile Lys Ile His Gln Gly Thr Leu Thr Ile
                 50                  55                  60

Leu Ser Leu Asn Ser Ser Leu Leu Gly Tyr Tyr Gln Cys Leu Ala
                 65                  70                  75

Asn Asn Ser Ile Gly Ala Ile Val Ser Gly Pro Ala Thr Val Ser
                 80                  85                  90

Val Ala Val Leu Gly Asp Phe Gly Ser Ser Thr Lys His Val Ile
                 95                 100                 105

Thr Ala Glu Glu Lys Ser Ala Gly Phe Ile Gly Cys Arg Val Pro
                110                 115                 120

Glu Ser Asn Pro Lys Ala Glu Val Arg Tyr Lys Ile Arg Gly Lys
                125                 130                 135

Trp Leu Glu His Ser Thr Glu Asn Tyr Leu Ile Leu Pro Ser Gly
                140                 145                 150

Asn Leu Gln Ile Leu Asn Val Ser Leu Glu Asp Lys Gly Ser Tyr
                155                 160                 165

Lys Cys Ala Ala Tyr Asn Pro Val Thr His Gln Leu Lys Val Glu
                170                 175                 180

Pro Ile Gly Arg Lys Leu Leu Val Ser Arg Pro Ser Ser Asp Asp
                185                 190                 195

Val His Ile Leu His Pro Thr His Ser Gln Ala Leu Ala Val Leu
                200                 205                 210

Ser Arg Ser Pro Val Leu Glu Cys Val Val Ser Gly Val Pro Ala
                215                 220                 225

Pro Gln Val Tyr Trp Leu Lys Asp Gly Gln Asp Ile Ala Pro Gly
                230                 235                 240

Ser Asn Trp Arg Arg Leu Tyr Ser His Leu Ala Thr Asp Ser Val
                245                 250                 255

Asp Pro Ala Asp Ser Gly Asn Tyr Ser Cys Met Ala Gly Asn Lys
                260                 265                 270

Ser Gly Asp Val Glu Tyr Val Thr Tyr Met Val Asn Val Leu Glu
                275                 280                 285
```

-continued

```
His Ala Ser Ile Ser Lys Gly Leu Gln Asp Gln Ile Val Ser Leu
            290                 295                 300
Gly Ala Thr Val His Phe Thr Cys Asp Val His Gly Asn Pro Ala
            305                 310                 315
Pro Asn Cys Thr Trp Phe His Asn Ala Gln Pro Ile His Pro Ser
            320                 325                 330
Ala Arg His Leu Thr Ala Gly Asn Gly Leu Lys Ile Ser Gly Val
            335                 340                 345
Thr Val Glu Asp Val Gly Met Tyr Gln Cys Val Ala Asp Asn Gly
            350                 355                 360
Ile Gly Phe Met His Ser Thr Gly Arg Leu Glu Ile Glu Asn Asp
            365                 370                 375
Gly Gly Phe Lys Pro Val Ile Ile Thr Ala Pro Val Ser Ala Lys
            380                 385                 390
Val Ala Asp Gly Asp Phe Val Thr Leu Ser Cys Asn Ala Ser Gly
            395                 400                 405
Leu Pro Val Pro Val Ile Arg Trp Tyr Asp Ser His Gly Leu Ile
            410                 415                 420
Thr Ser His Pro Ser Gln Val Leu Arg Ser Lys Ser Arg Lys Ser
            425                 430                 435
Gln Leu Ser Arg Pro Glu Gly Leu Asn Leu Glu Pro Val Tyr Phe
            440                 445                 450
Val Leu Ser Gln Ala Gly Ala Ser Ser Leu His Ile Gln Ala Val
            455                 460                 465
Thr Gln Glu His Ala Gly Lys Tyr Ile Cys Glu Ala Ala Asn Glu
            470                 475                 480
His Gly Thr Thr Gln Ala Glu Ala Ser Leu Met Val Val Pro Phe
            485                 490                 495
Glu Thr Asn Thr Lys Ala Glu Thr Val Thr Leu Pro Asp Ala Ala
            500                 505                 510
Gln Asn Asp Asp Arg Ser Lys Arg Asp Gly Ser Glu Thr Gly Leu
            515                 520                 525
Leu Ser Ser Phe Pro Val Lys Val His Pro Ser Ala Val Glu Ser
            530                 535                 540
Ala Pro Glu Lys Asn Ala Ser Gly Ile Ser Val Pro Asp Ala Pro
            545                 550                 555
Ile Ile Leu Ser Pro Pro Gln Thr His Thr Pro Asp Thr Tyr Asn
            560                 565                 570
Leu Val Trp Arg Ala Gly Lys Asp Gly Gly Leu Pro Ile Asn Ala
            575                 580                 585
Tyr Phe Val Lys Tyr Arg Lys Leu Asp Asp Gly Val Gly Met Leu
            590                 595                 600
Gly Ser Trp His Thr Val Arg Val Pro Gly Ser Glu Asn Glu Leu
            605                 610                 615
His Leu Ala Glu Leu Glu Pro Ser Ser Leu Tyr Glu Val Leu Met
            620                 625                 630
Val Ala Arg Ser Ala Ala Gly Glu Gly Gln Pro Ala Met Ile Thr
            635                 640                 645
Phe Arg Thr Ser Lys Glu Lys Thr Ala Ser Ser Lys Asn Thr Gln
            650                 655                 660
Ala Ser Ser Pro Pro Val Gly Ile Pro Lys Tyr Pro Val Val Ser
            665                 670                 675
Glu Ala Ala Asn Asn Asn Phe Gly Val Val Leu Thr Asp Ser Ser
```

-continued

```
                680                 685                 690
Arg His Ser Gly Val Pro Glu Ala Pro Asp Arg Pro Thr Ile Ser
                    695                 700                 705
Thr Ala Ser Glu Thr Ser Val Tyr Val Thr Trp Ile Pro Arg Ala
                    710                 715                 720
Asn Gly Gly Ser Pro Ile Thr Ala Phe Lys Val Glu Tyr Lys Arg
                    725                 730                 735
Met Arg Thr Ser Asn Trp Leu Val Ala Ala Glu Asp Ile Pro Pro
                    740                 745                 750
Ser Lys Leu Ser Val Glu Val Arg Ser Leu Glu Pro Gly Ser Thr
                    755                 760                 765
Tyr Lys Phe Arg Val Ile Ala Ile Asn His Tyr Gly Glu Ser Phe
                    770                 775                 780
Arg Ser Ser Ala Ser Arg Pro Tyr Gln Val Gly Phe Pro Asn
                    785                 790                 795
Arg Phe Ser Ser Arg Pro Ile Thr Gly Pro His Ile Ala Tyr Thr
                    800                 805                 810
Glu Ala Val Ser Asp Thr Gln Ile Met Leu Lys Trp Thr Tyr Ile
                    815                 820                 825
Pro Ser Ser Asn Asn Asn Thr Pro Ile Gln Gly Phe Tyr Ile Tyr
                    830                 835                 840
Tyr Arg Pro Thr Asp Ser Asp Asn Asp Ser Asp Tyr Lys Arg Asp
                    845                 850                 855
Val Val Glu Gly Ser Lys Gln Trp His Met Ile Gly His Leu Gln
                    860                 865                 870
Pro Glu Thr Ser Tyr Asp Ile Lys Met Gln Cys Phe Asn Glu Gly
                    875                 880                 885
Gly Glu Ser Glu Phe Ser Asn Val Met Ile Cys Glu Thr Lys Val
                    890                 895                 900
Lys Arg Val Pro Gly Ala Ser Glu Tyr Pro Val Lys Asp Leu Ser
                    905                 910                 915
Thr Pro Pro Asn Ser Leu Gly Ser Gly Gly Asn Val Gly Pro Ala
                    920                 925                 930
Thr Ser Pro Ala Arg Ser Ser Asp Met Leu Tyr Leu Ile Val Gly
                    935                 940                 945
Cys Val Leu Gly Val Met Val Leu Ile Leu Met Val Phe Ile Ala
                    950                 955                 960
Met Cys Leu Trp Lys Asn Arg Gln Gln Asn Thr Ile Gln Lys Tyr
                    965                 970                 975
Asp Pro Pro Gly Tyr Leu Tyr Gln Gly Ser Asp Met Asn Gly Gln
                    980                 985                 990
Met Val Asp Tyr Thr Thr Leu Ser Gly Ala Ser Gln Ile Asn Gly
                    995                 1000                1005
Asn Val His Gly Gly Phe Leu Thr Asn Gly Gly Leu Ser Ser Gly
                    1010                1015                1020
Tyr Ser His Leu His His Lys Val Pro Asn Ala Val Asn Gly Ile
                    1025                1030                1035
Val Asn Gly Ser Leu Asn Gly Gly Leu Tyr Ser Gly His Ser Asn
                    1040                1045                1050
Ser Leu Thr Arg Thr His Val Asp Phe Glu His Pro His His Leu
                    1055                1060                1065
Val Asn Gly Gly Gly Met Tyr Thr Ala Val Pro Gln Ile Asp Pro
                    1070                1075                1080
```

-continued

```
Leu Glu Cys Val Asn Cys Arg Asn Cys Arg Asn Asn Asn Arg Cys
            1085                1090                1095

Phe Thr Lys Thr Asn Ser Thr Phe Ser Ser Ser Pro Pro Pro Val
            1100                1105                1110

Val Pro Val Val Ala Pro Tyr Pro Gln Asp Gly Leu Glu Met Lys
            1115                1120                1125

Pro Leu Ser His Val Lys Val Pro Val Cys Leu Thr Ser Ala Val
            1130                1135                1140

Pro Asp Cys Gly Gln Leu Pro Glu Glu Ser Val Lys Asp Asn Val
            1145                1150                1155

Glu Pro Val Pro Thr Gln Arg Thr Cys Cys Gln Asp Ile Val Asn
            1160                1165                1170

Asp Val Ser Ser Asp Gly Ser Glu Asp Pro Ala Glu Phe Ser Arg
            1175                1180                1185

Gly Asp Ser Cys Ala His Ser Glu Thr Glu Ile Asn Ile Val Ser
            1190                1195                1200

Trp Asn Ala Leu Ile Leu Pro Pro Val Pro Glu Gly Cys Ala Glu
            1205                1210                1215

Lys Thr Met Trp Ser Pro Pro Gly Ile Pro Leu Asp Ser Pro Thr
            1220                1225                1230

Glu Val Leu Gln Gln Pro Arg Glu Thr
            1235
```

METHOD FOR USING BOC/CDO TO MODULATE HEDGEHOG SIGNALING

RELATED APPLICATIONS

The present application is a continuation-in-part of U.S. Ser. No. 11/609,472, filed Dec. 12, 2006 (abandoned), which claims benefit under 35 USC §119(e) to U.S. Ser. No. 60/752,220, filed Dec. 19, 2005 and U.S. Ser. No. 60/789,645, filed Apr. 5, 2006, the entire contents of which applications are incorporated herein by reference.

FIELD OF THE INVENTION

The present invention relates to the novel use of BOC/CDO receptor proteins to modulate hedgehog signaling and their therapeutic use in various physiological conditions or disorders that are in part mediated by or result therefrom (e.g., cancer).

BACKGROUND OF THE INVENTION

Members of the Hedgehog (Hh) family of signaling molecules mediate many important short- and long-range patterning processes during invertebrate and vertebrate embryonic, fetal, and adult development. In *Drosophila melanogaster*, a single hedgehog gene regulates segmental and imaginal disc patterning. In contrast, in vertebrates, a hedgehog gene family is involved in the control of proliferation, differentiation, migration, and survival of cells and tissues derived from all three germ layers, including, e.g., left-right asymmetry, CNS development, somites and limb patterning, chondrogenesis, skeletogenesis and spermogenesis.

The vertebrate family of hedgehog genes includes at least four members or paralogs of the single *Drosophila* hedgehog gene (WO 95/18856 and WO 96/17924). Three of these members, known as Desert hedgehog (Dhh), Sonic hedgehog (Shh) and Indian hedgehog (Ihh), apparently exist in all vertebrates, including fish, birds and mammals. Dhh is expressed principally in the testes, both in mouse embryonic development and in the adult rodent and human; Ihh is involved in bone development during embryogenesis and in bone formation in the adult; and Shh is involved in multiple embryonic and adult cell types derived from all three lineages. Shh is expressed at high levels in the notochoard and floorplate of developing vertebrate embryos, and directs cell fate in the developing limb, somites and neural tube. In vitro explant assays as well as ectopic expression of Shh in transgenic animals show that Shh plays a key role in neural tube patterning, Echelard et al., (1993), *Cell* 75: 1417-30 (1993); Ericson et al., *Cell* 81: 747-56 (1995); Marti et al, *Nature* 375: 322-25 (1995); Hynes et al., *Neuron* 19: 15-26 (1997). Hedgehog signaling also plays a role in the development of limbs (Krauss et al., *Cell* 75: 1431-44 (1993); Laufer et al., *Cell* 79: 1165-73 (1994); somites (Fan and Tessier-Lavigne, *Cell* 79: 1175-86 (1994); Johnson et al., *Cell* 79: 1165-73 (1994), lungs (Bellusci et al., *Devel.* 124: 53-63 (1997) and skin (Oro et al., *Science* 276: 817-21 (1997). Likewise, Ihh and Dhh are involved in bone, gut and germinal cell development (Apelqvist et al., *Curr. Biol.* 7: 801-804 (1997); Bellusci et al., *Dev. Suppl.* 124: 53-63 (1997); Bitgood et al., *Curr. Biol.* 6: 298-304 (1996); Roberts et al., *Development* 121: 3163-74 (1995). Specifically, Ihh has been implicated in chondrocyte development (Vortkamp et al., *Science* 273: 613-22 (1996)), while Dhh plays a key role in testes development.

Hedgehog signaling occurs through the interaction of hedgehog protein (e.g., in mammals, Shh, Dhh, Ihh, collectively "Hh") with the hedgehog receptor, patched (Ptch), and the co-receptor Smoothened (Smo). There are two mammalian homologs of Ptch, Ptch-1 and Ptch-2 ("collectively "Ptch"), both of which are 12 transmembrane proteins containing a sterol sensing domain (Motoyama et al., *Nature Genetics* 18: 104-106 (1998), Carpenter et al., *P.N.A.S. (U.S.A)* 95(23): 13630-40 (1998). The interaction of Hh with Ptch triggers a signaling cascade that results in the regulation of transcription by zinc-finger transcriptions factors of the Gli family.

The binding of Hh to Ptch releases Smoothened (Smo), a 7 transmembrane G-coupled protein to then activate an intricate intracellular signal-transduction pathway. The activation of Smo then leads to signaling through a multimolecular complex, including Costal2 (Cos2), Fused (Fu) and suppressor of Fused (Su(Fu)), resulting in nuclear transport of the transcription factor Gli. Ho et al., *Curr. Opin. Neurobiol.* 12:57-63 (2002); Nybakken et al., *Curr. Opin. Genet. Dev.* 12: 503-511 (2002); i Altaba et al., *Nat. Rev. Neurosci.* 3: 24-33 (2002). There are three known Gli transcription factors in verebrates: Gli1, Gli2 and Gli3. While Gli1 is a transcriptional activator that is universally induced in Hh-responsive cells, Gli2 and Gli3 can act either as activators or repressors of transcription depending on the cellular context. Absent Hh signaling, Gli3 is processed into a smaller, nuclear transcriptional repressor that lacks the carboxy-terminal domain of full-length Gli3. Upon activation of Smo, Gli3 protein cleavage is prevented, and the full-length form with transcription-activation function is generated. Gli2 also encodes a repressor function in its carboxy-terminally truncated form, but its formation does not appear to be regulated by Hh signaling. Stecca et al, *J. Biol.* 1(2):9 (2002).

Malignant tumors (cancers) are the second leading cause of death in the United States, after heart disease (Boring et al., *CA Cancel J. Clin.* 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

Hedgehog signaling has been implicated in a wide variety of cancers and carcinogenesis. One example of the carcinogenic process is vascularization. Angiogenesis, the process of sprouting new blood vessels from existing vasculature and arteriogenesis, the remodeling of small vessels into larger conduct vessels are both physiologically important aspects of vascular growth in adult tissues (Klagsbrun and D'Amore, *Annu. Rev. Physiol.* 53: 217-39 (1991); Folkman and Shing, *J. Biol. Chem.* 267(16): 10931-4 (1992); Beck and D'Amore, *FASEB J.* 11(5): 365-73 (1997); Yancopoulos et al., *Cell* 93(5): 661-4 (1998); Buschman and Scaper, *J. Pathol.* 190(3): 338-42 (2000). These processes of vascular growth are also required for beneficial processes such as tissue repair, wound healing, recovery from tissue ischemia and menstrual cycling. However, they are also required for the development of pathological conditions such as the growth of neoplasias, diabetic retinopathy, rheumatoid arthritis, psoriasis, certain forms of macular degeneration, and certain inflammatory pathologies (Cherrington et al., *Adv. Cancer Res.* 79:1-38 (2000). Thus, the inhibition of vascular growth can inhibit cellular proliferation, growth, differentiation and/or survival. As Hh has been shown to promote angiogenesis, Hh antagonists would be expected to possess anti-angiogenic properties.

The gene BOC [brother of CDO or regional cell adhesion molecule-related/down-regulated by oncogenes (Cdon) binding protein] encodes a type I plasma membrane protein having an Ig/FNIII repeating domain, and which likely functions as a receptor subunit for cell-cell communications. BOC protein is known to interact with CDO (cell adhesion molecule-related/down-regulated by oncogenes), N-cadherins, and M-cadherins in a cis fashion, forming a receptor complex at sites of cell-cell contact in myoblasts. Kang et al., *PNAS* 100(7): 3989-3994 (2003).

Like BOC, CDO is also a type I cell surface receptor protein, further sharing similar similar ectodomain (EC+TM domain) structural features, such as Ig repeats and Fibronectin (FN) type III repeats. More precisely, as shown in FIG. 6, BOC has five Ig repeats, and 3 FN repeats, while CDO has four Ig repeats and three FNIII repeats. However, the intracellular domains of BOC and CDO do not share significant homology. SiRNA knockdown of CDO in *Drosophila* leads to loss of hedgehog signaling responses. Lum et al., *Science* 299: 2039-2044 (2003). Others have shown that mutation of CDO in mammals results in a microform of holoprosencephaly (HPE), which is suggestive of involvement in hedgehog signaling. Cole et al., *Curr. Biol.* 13: 411-415 (2003). However, while HPE is a phenotype of hedgehog signaling failure, Cole et al. also points out that less than 15% of all cases of naturally occurring HPE result from mutations in hedgehog signaling components. Thus, HPE alone is not definitive of involvement in hedgehog signaling.

During embryonic development, BOC and CDO are expressed in the musculoskeletal and central nervous systems and in areas of proliferation and differentiation. BOC and CDO has further been associated with myogenic differentiation (Kang et al, *EMBO J.* 21(1&2): 114-124 (2002) and macrophage defects (PCT/US2006/019651, filed 18 May 2006). Expression of CDO and BOC in myoblast cell lines is downregulated by the ras oncogene, and forced re-expression of either CDO or BOC can override ras-induced inhibition of myogenic differentiation. Kang et al., *J. Cell Biol.* 143:403-413 (1998); Kang et al., *EMBO J.* 21:114-124 (2002). The promyogenic properties of CDO and BOC were further shown to be present in the human rhabdomyosarcoma cell line, RD. Stable overexpression of CDO or BOC in RD cells led to enhanced expression of two markers of muscle cell differentiation, troponin T and myosin heavy chain, and to increased formation of elongated, myosin heavy chain-positive myotubes. It has further been suggested that CDO and BOC play a role in the inverse relationship between differentiation and transformation of cells in the skeletal muscle lineage. Wegorzewska et al., *Mol. Carcinogenesis.* 37(1): 1-4 (2003).

Applicants demonstrate herein that both BOC and CDO can bind to Shh and differentially regulate hedgehog signaling, operating in tandem through a negative feedback mechanism. While BOC overexpression can inhibit Shh signaling to a level similar as Ptch1 overexpression, CDO Δ(cyt) overexpression (CDO lacking the cytoplasmic domain) potentiated Hh signaling at suboptimal Shh concentrations. This suggests that BOC can sequester or antagonize Hh signaling, while CDO can amplify or agonize Hh signaling. Moreover, BOC and CDO, as well as antagonists thereof, could be an effective therapeutic to treat disorders that are implicated by aberrant hedgehog signaling.

SUMMARY OF THE INVENTION

In the broadest sense, the invention provides for a method of modulating hedgehog signaling using BOC and/or CDO and antagonists thereof. In a more directed sense, the method is expected to be applicable to the treatment of disorders or conditions related to hedgehog signaling, including cancer and the pathogenesis thereof. While both BOC and CDO appear in normal physiology to bind to Hh, BOC can sequester or prevent Hh from binding to its receptors (e.g., Ptch-1 and Ptch-2), thereby preventing activation of the canonical hedgehog signaling pathway. In contrast, CDO can amplify hedgehog signaling activity resulting from the binding of Shh to its receptors, especially at suboptimal concentrations. Agents which mimic the physiological activity of BOC, or antagonize CDO, would be expected to antagonize hedgehog signaling, while agents which inhibit BOC, including preventing it from binding to Hh, or agents that mimic the physiological activity of CDO, would be expected to agonize hedgehog signaling.

In one embodiment, the invention concerns an article of manufacture comprising a container and a composition of matter contained within the container, wherein the composition of matter may comprise a BOC/CDO hedgehog antagonist. In a specific aspect, a BOC/CDO hedgehog antagonist further comprises (1) a BOC hedgehog antagonist, (2) a CDO antagonist, or (3) any combination of (1) or (2). In another specific aspect, the BOC hedgehog antagonist may comprise: a BOC polypeptide, an agonist anti-BOC antibody, an agonist BOC-binding antibody fragment, or an agonist BOC binding oligopeptide. In yet another specific aspect, the CDO antagonist may comprise: a CDO antagonist polypeptide, an anti-CDO antibody, a CDO-binding antibody fragment, CDO-binding oligopeptide, CDO binding small organic molecule or CDO RNAi. The article may further optionally comprise a label affixed to the container, or a package insert included with the container, that refers to the use of the composition of matter described in (1), (2) or (3) for the therapeutic treatment or diagnostic detection of a conditions related to the over- or under-expression of hedgehog signaling.

In another embodiment, the present invention concerns the use of BOC/CDO hedgehog antagonist for the preparation of a medicament useful in the treatment of a condition which is responsive to the BOC/CDO hedgehog antagonist.

In yet another embodiment, the present invention concerns a method for inhibiting hedgehog signaling, comprising contacting a cell in which hedgehog signaling is active with an effective amount of a BOC/CDO hedgehog antagonist. In a specific aspect, the BOC/CDO hedgehog antagonist causes inhibition of the growth of the cell expressing the hedgehog polypeptide. In another specific aspect, the cell is a cancer cell or tumor. In yet another specific aspect, the BOC/CDO hedgehog antagonist binding to the hedgehog polypeptide causes death of the cell expressing active hedgehog signaling. In yet a further specific aspect, the BOC/CDO hedgehog antagonist is: (1) a BOC hedgehog antagonist; such as (a) a BOC polypeptide, (b) an agonist anti-BOC antibody, (c) an agonist BOC-binding antibody fragment, or (d) an agonist BOC binding oligopeptide; and/or (2) a CDO antagonist, including (a) a CDO antagonist polypeptide, such as (i) an anti-CDO antibody, (ii) a COD-binding antibody fragment, (iii) an antagonist CDO chimeric polypeptide, (iv) a CDO binding oligopeptide, and (b) a CDO binding small organic molecule, or (c) CDO RNAi. The BOC/CDO hedgehog antagonists employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The BOC hedgehog antagonists and CDO antagonist polypeptides employed in the methods of the present invention may optionally be produced in CHO cells, yeast cells or bacterial cells.

In yet a further embodiment, the present invention concerns a method of therapeutically treating a mammal having a cancerous tumour, comprising cells that express a hedgehog polypeptide, wherein the method comprises administering to the mammal a therapeutically effective amount of a BOC/CDO hedgehog antagonist that binds to the hedgehog polypeptide or a cell expressing it, thereby resulting in the effective treatment of the tumor. In yet a further specific aspect, the BOC/CDO hedgehog antagonist is: (1) a BOC hedgehog antagonist; such as (a) a BOC polypeptide, (b) an agonist anti-BOC antibody, (c) an agonist BOC-binding antibody fragment, or (d) an agonist BOC binding oligopeptide; and/or (2) a CDO antagonist, including (a) a CDO antagonist polypeptide, such as (i) an anti-CDO antibody, a COD-binding antibody fragment, (iii) an antagonist CDO chimeric polypeptide, (iv) a CDO binding oligopeptide, (b) a CDO binding small organic molecule, or (c) CDO RNAi. The BOC/CDO hedgehog antagonists employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The BOC hedgehog antagonists and CDO antagonist polypeptides employed in the methods of the present invention may optionally be produced in CHO cells, yeast cells or bacterial cells.

In yet a further embodiment, the present invention concerns a method of diagnosing the presence of a tumor in a mammal, comprising detecting the level of expression of a gene encoding a BOC polypeptide and/or CDO polypeptide (a) in a test sample of tissue or cells obtained from said mammal, and (b) in a control sample of known normal non-cancerous cells of the same tissue origin or type, wherein a lower level of expression of the BOC polypeptide in the test sample, and/or higher level of expression of the CDO polypeptide, as compared to the control sample, is indicative of the presence of tumor in the mammal from which the test sample was obtained.

In yet a further embodiment, the present invention concerns a method of diagnosing the presence of a tumor in a mammal, comprising: (a) contacting a test sample comprising tissue or cells obtained from the mammal with: (1) a BOC polypeptide, an anti-BOC antibody, a BOC-binding antibody fragment, a BOC binding oligopeptide, BOC sense/antisense nucleic acid, or BOC binding small organic molecule; or (2) a CDO polypeptide, an anti-CDO antibody, a CDO-binding antibody fragment, a CDO-binding oligopeptide, a CDO sense/antisense nucleic acid, a CDO binding small organic molecule, or a CDO RNAi or (3) any combination of (1) or (2); and (b) detecting the formation of a complex between the molecule(s) of (1), (2) or (3) and the test sample, wherein the formation of less or more complex in the sample relative to a control sample is indicative of the presence of a tumor in the mammal. Optionally, the molecules of (1), (2) or (3) are detectably labeled, attached to a solid support, or the like, and/or the test sample of tissue or cells is obtained from an individual suspected of having a cancerous tumor.

In yet a further embodiment, the present invention concerns a method for treating or preventing a cell proliferative disorder associated with altered, preferably decreased, expression or activity of a BOC polypeptide, the method comprising administering to a subject in need of such treatment an effective amount of a BOC hedgehog antagonist. In a specific aspect, the cell proliferative disorder is cancer and the BOC hedgehog antagonist is a BOC polypeptide. Effective treatment or prevention of the cell proliferative disorder may be a result of direct killing or growth inhibition of cells that underexpress a BOC polypeptide or by antagonizing the cell growth potentiating activity of a hedgehog polypeptide and/or hedgehog signaling component.

In yet a further embodiment, the present invention concerns a method for treating or preventing a cell proliferative disorder associated with altered, preferably increased, expression or activity of a CDO polypeptide, the method comprising administering to a subject in need of such treatment an effective amount of a CDO antagonist. In a specific aspect, the cell proliferative disorder is cancer and the CDO antagonist is an anti-CDO antibody. Effective treatment or prevention of the cell proliferative disorder may be a result of direct killing or growth inhibition of cells that overexpress a CDO polypeptide or by antagonizing the cell growth potentiating activity of a hedgehog polypeptide and/or hedgehog signaling component.

In yet a further embodiment, the present invention concerns the use of (a) a BOC polypeptide, (b) a nucleic acid encoding a BOC polypeptide or a vector or host cell comprising the nucleic acid of (a), (c) an anti-BOC polypeptide antibody, (d) a BOC-binding antibody fragment, (e) a BOC-binding oligopeptide, (f) a BOC sense/antisense nucleic acid or (g) a COC-binding small organic molecule in the preparation of a medicament useful for (i) the therapeutic treatment or diagnostic detection of a cancer or tumor, or (ii) the therapeutic treatment or prevention of a cell proliferative disorder.

In yet a further embodiment, the present invention concerns the use of (a) a CDO polypeptide, (b) a nucleic acid encoding a CDO polypeptide or a vector or host cell comprising the nucleic acid of (a), (c) an anti-CDO polypeptide antibody, (d) a CDO-binding antibody fragment (e) a CDO-binding oligopeptide, (f) a CDO sense/antisense nucleic acid, (g) a CDO-binding small organic molecule, or (h) CDO RNAi, in the preparation of a medicament useful for (I) the therapeutic treatment or diagnostic detection of a cancer or tumor, or (II) the therapeutic treatment or prevention of a cell proliferative disorder.

In yet a further embodiment, the present invention concerns a method for inhibiting the growth of a cancer cell, wherein the growth of said cancer cell is at least in part dependent upon the growth potentiating effect(s) of a hedgehog polypeptide and the modulation thereof by a BOC polypeptide and/or CDO polypeptide (wherein any or all of the hedgehog polypeptide, BOC polypeptide or CDO polypeptide may be expressed either by the cancer cell itself, a cell in close proximity thereto, or another/other cell that produces such polypeptide(s), wherein the method comprises contacting the hedgehog polypeptide with a BOC hedgehog antagonist and/or CDO antagonist that binds to the hedgehog, BOC and/or CDO polypeptide, as the case may be, thereby antagonizing the growth-potentiating activity of the hedgehog polypeptide and, in turn, inhibiting the growth of the cancer cell. In a specific aspect, the growth of the cancer cell is completely inhibited. In another specific aspect, the binding of the BOC hedgehog antagonist and/or CDO antagonist to the hedgehog polypeptide induces the death of the cancer cell. In yet a further specific aspect, the BOC/CDO hedgehog antagonist is: (1) a BOC hedgehog antagonist; such as (a) a BOC polypeptide, (b) an agonist anti-BOC antibody, (c) an agonist BOC-binding antibody fragment, or (d) an agonist BOC binding oligopeptide; and/or (2) a CDO antagonist, including (a) a CDO antagonist polypeptide, such as (i) an anti-CDO antibody, a COD-binding antibody fragment, (iii) an antagonist CDO chimeric polypeptide, (iv) a CDO binding oligopeptide, (b) a CDO binding small organic molecule, or (c) CDO RNAi. The BOC/CDO hedgehog antagonists employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The BOC hedgehog antagonists and CDO antagonist polypeptides employed in the methods of the present invention may optionally be produced in CHO cells, yeast cells or bacterial cells.

In yet a further embodiment, the present invention concerns a method of therapeutically treating a tumor in a mammal, wherein the growth of said tumor is at least in part dependent upon the growth potentiating effect(s) of a hedgehog polypeptide and the modulation thereof by a BOC polypeptide and/or CDO polypeptide (wherein either or both the hedgehog polypeptide, BOC polypeptide and/or CDO polypeptide may be expressed either by the cancer cell itself or another cell(s) that produce(s) polypeptide(s) that have a growth potentiating or modulating effect on cancer cells), wherein the method comprises administering to the mammal a therapeutically effective amount of a BOC/CDO hedgehog antagonist that binds to the hedgehog, BOC polypeptide, and/or CDO polypeptide, as the case may be, thereby antagonizing the growth-potentiating activity of the hedgehog polypeptide and resulting in the effective therapeutic treatment of the tumor. In yet a further specific aspect, the BOC/CDO hedgehog antagonist is: (1) a BOC hedgehog antagonist; such as (a) a BOC polypeptide, (b) an agonist anti-BOC antibody, (c) an agonist BOC-binding antibody fragment, or (d) an agonist BOC binding oligopeptide; and/or (2) a CDO antagonist, including (a) a CDO antagonist polypeptide, such as (i) an anti-CDO antibody, a COD-binding antibody fragment, (iii) an antagonist CDO chimeric polypeptide, (iv) a CDO binding oligopeptide, (b) a CDO binding small organic molecule, or (c) CDO RNAi. The BOC/CDO hedgehog antagonists employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The BOC hedgehog antagonists and CDO antagonist polypeptides employed in the methods of the present invention may optionally be produced in CHO cells, yeast cells or bacterial cells.

In yet a further embodiment, the invention concerns a method of preventing the proliferation, growth, differentiation or survival of a cell with an active hedgehog signaling pathway comprising contacting said cell with an effective amount of a BOC/CDO hedgehog antagonist. In a specific aspect, an active hedgehog signaling pathway may be determined by the overexpression or nuclear transportation of a Gli gene, (e.g., Gli1). In another specific aspect, an active hedgehog signaling pathway may be determined by the overexpression of a hedgehog gene or the presence of a mutated or dysfunctional hedgehog gene in the canonical hedgehog signaling pathway (e.g., ptch-1, ptch-2, Smo, Fu, Su(Fu), Cos-2, etc.). In yet another specific aspect, the BOC hedgehog antagonist is a BOC polypeptide and/or the CDO antagonist is an anti-CDO antibody. In yet a further specific aspect, the BOC/CDO hedgehog antagonist is: (1) a BOC hedgehog antagonist; such as (a) a BOC polypeptide, (b) an agonist anti-BOC antibody, (c) an agonist BOC-binding antibody fragment, or (d) an agonist BOC binding oligopeptide; and/or (2) a CDO antagonist, including (a) a CDO antagonist polypeptide, such as (i) an anti-CDO antibody, a COD-binding antibody fragment, (iii) an antagonist CDO chimeric polypeptide, (iv) a CDO binding oligopeptide, (b) a CDO binding small organic molecule, or (c) CDO RNAi. The BOC/CDO hedgehog antagonists employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The BOC hedgehog antagonists and CDO antagonist polypeptides employed in the methods of the present invention may optionally be produced in CHO cells, yeast cells or bacterial cells.

In yet a further embodiment, the invention concerns a method of inhibiting or preventing cellular proliferation comprising contacting a cell or tissue undergoing proliferation or in which proliferation is to be prevented, with an effective amount of a BOC/CDO hedgehog antagonist. In a specific aspect, the cell proliferation is cancer. In another specific aspect, the cell proliferation is benign hyperplasia. In yet another specific aspect, the benign hyperplasia is benign prostatic hyperplasia.

In yet a further embodiment, the invention concerns a method of treating cancer comprising contacting a cancer cell or tissue with an effective amount of a BOC/CDO hedgehog antagonist. In a specific aspect, the cancer is prostate (e.g., adenocarcinoma), bladder, biliary, lung (e.g., small cell or non-small cell), colon, kidney, liver, breast, urogenital cervical, uterine (e.g., endometrial), ovarian, testicular, cancer of the penis, cancer of the vagina, cancer of the urethra], gall bladder, esophageal or pancreatic. In another specific aspect, the cancer is skeletal or smooth muscle, stomach, cancer of the small intestine, cancer of the salivary gland, anal, rectal, thyroid, parathyroid, pituitary and nasopharyngeal. In yet another aspect, the method is combined with conventional anti-cancer therapy, such as the administration of a chemotherapeutic agent or monoclonal antibody targeting a hedgehog signaling component or another target implicated in the cancer.

In yet a further specific aspect, said cancer is a cancer of the neuronal system. In yet a still further aspect, the cancer is malignant glioma, meningioma, medulloblastoma, neuroectodermal tumors and ependymoma.

In yet a further specific aspect, said cancer is associated with breast tissue. In still yet a further aspect, the cancer is inferior ductal carcinoma, inferior lobular carcinoma, intraductal carcinoma, medullary carcinoma and tubular carcinoma.

In yet a further specific aspect, said cancer is associated with lung tissue. In still yet a further aspect, the cancer is adenocarcinoma, broncho-alveolar adenocarcinoma, squamous cell carcinoma and small cell carcinoma.

In yet a further embodiment, the invention concerns a method of inhibiting angiogenesis comprising contacting a cell or tissue in which angiogenesis is to be inhibited with an effective amount of a BOC/CDO hedgehog antagonist. In a specific aspect, the method may be combined with another anti-angiogenic therapy. In another specific aspect, such angiogenesis results from: tumor growth, tumor metastasis or abnormal growths by endothelial cells, including neovascular disease, age-related macular degeneration, diabetic retinopathy, retinopathy of prematurity, corneal graft rejection, neovascular glaucoma, retrolental fibroplasias, epidemic keratoconjuctivitis, Vitamin A deficiency, contact lens overwear, atopi keratiti, superior limbic keratitis, ptyergium keratitis sicca, Sjogren's syndrome, acne rosacea, phylctenulosis, syphilis, Mycobacteria infections, lipid degeneration, chemical burns, bacterial ulcers, fungal ulcers, Herpes simplex infections, Herpes Zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's granulomatosis, sarcoidosis, scleritis, Steven-Johnson syndrome, pemphigoid radial keratotomy, corneal graph rejection, rheumatoid arthritis, osteoarthritis, chronic inflammation (e.g., ulcerative colitis or Crohn's disease), hemangioma, Osler-Weber-Rendu disease, and hereditary hemorrhagic telangiectasia.

In yet another specific aspect, such angiogenesis results from: wound healing, ovulation, and implantation of the blastula after fertilization. In a further specific aspect, such angiogenesis occurs during: normal hair growth, trichosis, hypertrichosis, hirsutism or folliculitis including folliculitis ulerythrmatosa reticulata, keloid folliculitis, and pseudofolliculitis. When angiogenesis is desireable, the component attributable to hedgehog signaling may be augmented by application of (1) inhibitors of BOC, or agents which prevent it from binding to hedgehog as well as (2) CDO polypeptides or agents which augment or mimic the physiological activity of CDO.

In yet a further embodiment, the invention concerns a method to modulate the proliferation, differentiation, or survival of uncommitted stem cells in culture comprising contacting such cells with an effective amount of a BOC/CDO hedgehog antagonist. In a specific aspect, the method can differentiate stem cells into terminally differentiated neuronal cells for use in intracerebral grafting. In another specific aspect, such terminally differentiated neuronal cells are glial cells, schwann cells, chromaffin cells, cholinergic sympathetic or parasympathetic neurons, and peptidergic and serotonergic neurons. In yet another specific aspect, such BOC/CDO hedgehog antagonist is used in combination with another neurotrophic factor.

In yet a further embodiment, the invention concerns a method to modulate the proliferation, differentiation or survival of cells in a patient suffering from a neurological disorder comprising contacting such cells with a therapeutically effective amount of BOC/CDO hedgehog antagonist. In a specific aspect, the neurological disorder results from: (i) acute, subacute, or chronic injury to the nervous system, including traumatic injury, chemical injury, vascular injury and deficits, ischemia resulting from stroke, infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and spinocerebellar degenerations; and (iv) chronic immunological diseases of the nervous system or affecting the nervous system, including multiple sclerosis.

In yet a further embodiment, the invention concerns a method to modulate the proliferation, differentiation or survival of cells in a patient undergoing chondrogenesis or osteogenesis, comprising contacting such cells with an effective amount of a BOC/CDO hedgehog antagonist. In a specific aspect, the chondrogenesis or osteogenesis occurs in a therapeutic intervention in the treatment of cartilage of a diathroidal joint or a tempomandibular joint, or in cartilage transplantation and prosthetic device therapies. In another specific aspect, the chondrogenesis or osteogenesis occurs in regimen for the generation of bone in which skeletal tissue is deficient.

In yet a further embodiment, the invention concerns a method to modulate the proliferation, differentiation or survival of cells in a patient undergoing hair regeneration or regrowth, comprising contacting such cells with an effective amount of BOC/CDO hedgehog antagonist. In a specific aspect, the proliferation, differentiation or survival occurs after chemotherapy or radiotherapy.

In yet another embodiment, the invention provides for a method of stimulating surfactant production in a lung cell comprising contacting said cell with a BOC/CDO hedgehog antagonist in an amount effective to stimulate surfactant production.

In yet another embodiment, the invention provides for a method of stimulating lamellated body formation in a lung cell comprising contacting said cell with a BOC/CDO hedgehog antagonist in an amount effective to stimulate lamellated body formation. In one aspect, said cell is present in the lung tissue of a premature infant.

In yet another embodiment, the invention provides for a method of inhibiting hedgehog signaling comprising contacting a cell in which inhibition of said hedgehog signaling is desired with at least a therapeutically effective amount of a BOC/CDO hedgehog antagonist. In a specific aspect, the hedgehog signaling is involved in the regulation or repair and/or function in a wide range of: (i) cells and tissues having a hedgehog gain-of-function phenotype and (ii) cells and tissues with wild-type hedgehog activity. In another specific aspect, such hedgehog signaling is related an activity selected from the group consisting of: regulation of neural tissues, bone and cartilage formation and repair, regulation of spermatogenesis, regulation of smooth muscle, regulation of lung and liver, regulation of tissue arising from the primitive gut, regulation of hematopoietic function, regulation of skin and hair growth. In yet another specific aspect, such cells or tissue exhibiting the undesired hedgehog signaling are in vitro. In yet a further aspect, such cells or tissue exhibiting the undesired hedgehog signaling are in vivo.

Yet further embodiments of the present invention will be evident to the skilled artisan upon a reading of the present specification.

BRIEF DESCRIPTION OF THE DRAWINGS

FIG. 1A shows the nucleotide sequence DNA59586 (SEQ ID NO:1), which encodes PRO1190, a native sequence BOC polypeptide. The nucleotide sequence is a clone designated herein as "UNQ604", "DNA59586" and/or "DNA59586-1520".

FIG. 1B sequence the nucleotide sequence DNA227967 (SEQ ID NO:2), which encodes PRO38430, a native sequence CDO polypeptide. The nucleotide sequence is a clone designated herein as "UNQ9067" and/or "DNA227967". The location of the initiator methionine and termination codons in the respective DNA59586 and DNA227967 molecules are also indicated.

FIG. 2A shows the derived amino acid sequence of a native sequence BOC polypeptide (SEQ ID NO:3).

FIG. 2B shows the derived amino acid sequence of a native sequence CDO polypeptide (SEQ ID NO:4). Various features of the BOC polypeptide (PRO1190) and CDO polypeptide (PRO38430) indicated in FIGS. 2A and 2B, respectively, are indicated.

DETAILED DESCRIPTION OF THE INVENTION

I. Overview

Figure 3:
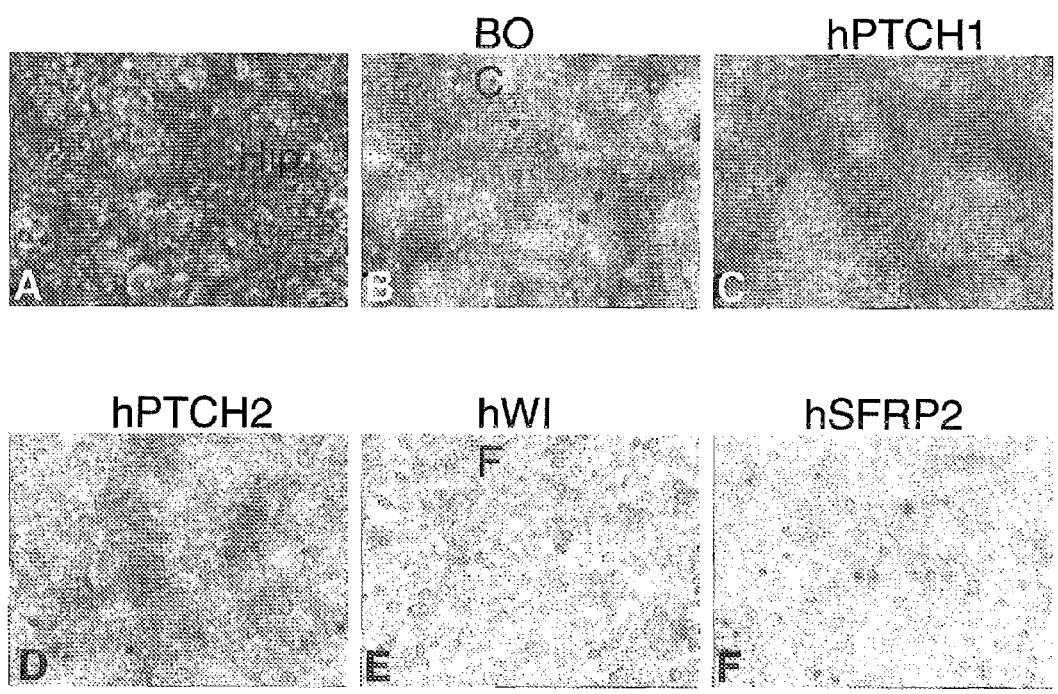
FIGS. 3A-F show the binding of BOC and various other known Shh binding cell surface proteins (e.g., Hip, BOC, Ptch1, Ptch2) in micrographs of Cos7 cells transfected with these Sh-binding cell surface proteins, sonic hedgehog-alkaline phosphatase chimeras (Shh-AP) and the negative controls WIF and sFRP2, which are known Wnt pathway signaling components.

The present invention relates to the discovery that signal transduction pathways regulated by hedgehog signaling (e.g., hedgehog, patched, smoothened, fused, suppressor of fused, costal-2, etc.) can be modulated by BOC and/or CDO polypeptide. While not limited to this particular mechanism of action, it appears that BOC may operate as a decoy receptor or sequestering agent for hedgehog, thereby preventing secreted hedgehog from otherwise binding to the Hh receptors thereby initiating hedgehog signaling, while CDO seems to play the opposite role—potentiating or amplifying hedgehog signaling.

Thus, it is specifically contemplated that the BOC/CDO hedgehog antagonists of the present invention will not only interfere with aspects of hedgehog signal transduction activity, but will likewise be capable of changing the fate of a cell or tissue that is affected by hedgehog signaling, such as cells undergoing normal development or disease states that are characterized by aberrant (i.e., over and/or under-expressing) hedgehog signaling. More specifically, such hedgehog signaling can occur either (i) as wild-type hedgehog signaling (such as that resulting from somatic mutation or congenital defect) or (ii) as a result from hyperactivation of hedgehog pathway. Disorders resulting from hyperactivation of the hedgehog pathway can be attributed to mutations arising in hedgehog signaling components or inappropriate activation or stimulation that does not result from a mutation or lesion in a hedgehog signaling component. It is therefore desireable to have a method for identifying those cells in which the hedgehog pathway is hyperactive such that treatment with BOC/CDO hedgehog antagonists can be efficiently targeted. One of skill in the art will readily recognize that BOC/CDO hedgehog antagonists are suitable for the treatment of conditions or disorders characterized by hyperactive hedgehog signaling as well as modifying the cell fate during development by suppression of hedgehog concentration.

II. Definitions

A "BOC polypeptide," and includes both "native sequence BOC polypeptides" and "BOC polypeptide variants", as described below, and chimeric BOC polypeptides, which are BOC polypeptides fused to a heterologous sequence (e.g. immunoadhesin).

A "CDO polypeptide," and includes both "native sequence CDO polypeptides" and "CDO polypeptide variants", as described below, and chimeric CDO polypeptides, which are CDO polypeptides fused to a heterologous sequence (e.g., immunoadhesin).

A "native sequence BOC polypeptide" comprises a polypeptide having the same amino acid sequence as the corresponding BOC polypeptide derived from nature. Such native sequence BOC polypeptides can be isolated from nature or can be produced by recombinant or synthetic means. The term "native sequence BOC polypeptide" specifically encompasses naturally-occurring truncated or secreted forms of the specific BOC polypeptide (e.g., an extracellular domain sequence), naturally-occurring variant forms (e.g., alternatively spliced forms) and naturally-occurring allelic variants of the polypeptide. In one specific aspect, the native sequence BOC polypeptides disclosed herein are mature or full-length native sequence polypeptides corresponding to the sequences recited in FIG. 2A.

A "native sequence CDO polypeptide" comprises a polypeptide having the same amino acid sequence as the corresponding CDO polypeptide derived from nature. Such native sequence CDO polypeptides can be isolated from nature or can be produced by recombinant or synthetic means. The term "native sequence CDO polypeptide" specifically encompasses naturally-occurring truncated or secreted forms of the specific CDO polypeptide (e.g., an extracellular domain sequence), naturally-occurring variant forms (e.g., alternatively spliced forms) and naturally-occurring allelic variants of the polypeptide. In one specific aspect, the native sequence CDO polypeptides disclosed herein are mature or full-length native sequence polypeptides corresponding to the sequences recited in FIG. 2B.

"BOC polypeptide variant or CDO polypeptide variant" means a BOC or CDO polypeptide, respectively, preferably active forms thereof, as defined herein, having at least about 80% amino acid sequence identity with a full-length native sequence BOC or CDO polypeptide sequence, respectively, as disclosed herein, and variant forms thereof lacking the signal peptide, an extracellular domain, or any other fragment of a full length native sequence BOC polyeptide or CDO polypeptide, respectively, such as those referenced herein. Such variant polypeptides include, for instance, polypeptides wherein one or more amino acid residues are added, or deleted, at the N- or C-terminus of the full-length native amino acid sequence. In a specific aspect, such variant polypeptides will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence BOC polypeptide or CDO polypeptide, respectively, as disclosed herein, and variant forms thereof lacking the signal peptide, an extracellular domain, or any other fragment of a full length native sequence BOC polypeptide or CDO polypeptide, respectively, such as those disclosed herein. In a specific aspect, such variant polypeptides will vary at least about 1, 2, 3, 4, 5, 6, 7, 8, 9, 10, 20, 25, 30, 35, 40, 45, 50, 60, 70, 80, 90, 100, 125, 150, 200, 250, 300 or more amino acid residues in length from the corresponding native sequence polypeptide. Alternatively, such variant polypeptides will have no more than one conservative amino acid substitution as compared to the corresponding native polypeptide sequence, alternatively no more than 2, 3, 4, 5, 6, 7, 8, 9, or 10 conservative amino acid substitution as compared to the native polypeptide sequence.

"Percent (%) amino acid sequence identity" with respect to the BOC polypeptide or CDO polypeptide sequences identified herein is defined as the percentage of amino acid residues in a candidate sequence that are identical with the amino acid residues in the specific BOC polypeptide sequence, or CDO polypeptide sequence, respectively, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

"BOC variant polynucleotide" or "BOC variant nucleic acid sequence" means a nucleic acid molecule which encodes a BOC polypeptide, preferably active forms thereof, as defined herein, and which have at least about 80% nucleic acid sequence identity with a nucleotide acid sequence encoding a full-length native sequence BOC polypeptide sequence identified herein, or any other fragment of the respective full-length BOC polypeptide sequence as identified herein (such as those encoded by a nucleic acid that represents only a portion of the complete coding sequence for a full-length BOC polypeptide).

"CDO variant polynucleotide" or "CDO variant nucleic acid sequence" means a nucleic acid molecule which encodes a CDO polypeptide, preferably active forms thereof, as defined herein, and which have at least about 80% nucleic acid sequence identity with a nucleotide acid sequence encoding a full-length native sequence CDO polypeptide sequence identified herein, or any other fragment of the respective full-length CDO polypeptide sequence as identified herein (such as those encoded by a nucleic acid that represents only a portion of the complete coding sequence for a full-length CDO polypeptide). Ordinarily, such variant polynucleotides (i.e., either BOC or CDO) will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding the respective full-length native sequence BOC or CDO polypeptide sequence, respectively, or any other fragment of the respective full-length BOC or CDO polypeptide sequence identified herein. Such variant polynucleotides do not encompass the native nucleotide sequence.

Ordinarily, such variant polynucleotides vary at least about 50 nucleotides in length from the native sequence polypeptide, alternatively the variance can be at least about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to BOC polypeptide-encoding nucleic acid sequences or CDO polypeptide-encoding nucleic acid sequences identified herein, is defined as the percentage of nucleotides in a candidate sequence that are identical with the nucleotides in the BOC or CDO nucleic acid sequence of interest, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

$$100 \text{ times the fraction } W/Z$$

where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 3 and 4, demonstrate how to calculate the % nucleic acid sequence identity of the nucleic acid sequence designated "Comparison DNA" to the nucleic acid sequence designated "REF-DNA", wherein "REF-DNA" represents a hypothetical BOC-encoding nucleic acid sequence of interest, "Comparison DNA" represents the nucleotide sequence of a nucleic acid molecule against which the "REF-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, BOC variant polynucleotides or CDO variant polynucleotides are nucleic acid molecules that encode BOC polypeptides or CDO polypeptides, respectively, and which are capable of hybridizing, preferably under stringent hybridization and wash conditions, to nucleotide sequences encoding a full-length BOC polypeptide, or full-length CDO polypeptide, respectively, as disclosed herein. Such variant polypeptides may be those that are encoded by such variant polynucleotides.

"Isolated", when used to describe the various BOC polypeptides or CDO polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, such polypeptides will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Such isolated polypeptides includes the corresponding polypeptides in situ within recombinant cells, since at least one component of the BOC polypeptide or CDO polypeptide from its natural environment will not be present. Ordinarily, however, such isolated polypeptides will be prepared by at least one purification step.

An "isolated" BOC polypeptide-encoding nucleic acid or CDO polypeptide-encoding nucleic acid is a nucleic acid molecule that is identified and separated from at least one contaminant nucleic acid molecule with which it is ordinarily associated in the natural source of the polypeptide-encoding nucleic acid. Any of the above such isolated nucleic acid molecule is other than in the form or setting in which it is found in nature. Any such nucleic acid molecules therefore are distinguished from the specific polypeptide-encoding nucleic acid molecule as it exists in natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The ordinarily skilled artisan will recognize how to adjust the temperature, ionic strength, etc. as necessary to accommodate factors such as probe length and the like.

The term "epitope tagged" when used herein refers to a chimeric polypeptide comprising a BOC polypeptide or CDO polypeptide fused to a "tag polypeptide". The tag polypeptide has enough residues to provide an epitope against which an antibody can be made, yet is short enough such that it does not interfere with the activity of the polypeptide to which it is fused. The tag polypeptide preferably also is sufficiently unique so that such antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a BOC polypeptide or CDO polypeptide which retain a biological and/or an immunological activity of native or naturally-occurring BOC polypeptide or CDO polypeptide, respectively, wherein "biological" activity refers to a biological function (either inhibitory or stimulatory) caused by a native or naturally-occurring BOC polypeptide or CDO polypeptide, respectively, other than the ability to induce the production of an antibody against an antigenic epitope possessed by a native or naturally-occurring BOC polypeptide or CDO polypeptide, respectively, and an "immunological" activity refers to the ability to induce the production of an antibody against an antigenic epitope possessed by a native or naturally-occurring BOC polypeptide or CDO polypeptide, respectively. An active BOC polypeptide or CDO polypeptide, as used herein, is an antigen that is differentially expressed, either from a qualitative or quantitative perspective, in diseased tissue (e.g. tumor, cancer, tissue with aberrant hedgehog expression), relative to its expression on similar, undiseased tissue.

The term "antagonist" is used in the broadest sense, and includes any molecule that partially or fully blocks, inhibits, or neutralizes, preferably specifically, a biological activity of target it is directed against.

"Treating" or "treatment" or "alleviation" refers to both therapeutic treatment and prophylactic or preventative measures, wherein the object is to prevent or slow down (lessen) the progression of a disease. "Diagnosing" refers to the process of identifying or determining the distinguishing characteristics of a disease or tumor. The process of diagnosing is sometimes also expressed as staging or tumor classification based on severity or disease progression.

Subjects in need of treatment or diagnosis include those already with aberrant hedgehog signaling as well as those prone to having or those in whom aberrant hedgehog signaling is to be prevented. A subject or mammal is successfully "treated" for aberrant hedgehog signaling if, according to the method of the present invention, after receiving a therapeutic amount of a BOC/CDO hedgehog antagonist, the patient shows observable and/or measurable reduction in or absence of one or more of the following: reduction in the number of tumor cells or absence of such cells; reduction in the tumor size; inhibition (i.e., slow to some extent and preferably stop) of tumor cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent such BOC/CDO hedgehog antagonists may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and tests for calcium level and other enzymes to determine the extent of metastasis. CT scans can also be done to look for spread to regions outside of the tumor or cancer. The invention described herein relating to the process of prognosing, diagnosing and/or treating involves the determination and evaluation of BOC and hedgehog amplification and expression.

"Mammal" for purposes of the treatment of, alleviating the symptoms of or diagnosis of a cancer refers to any animal classified as a mammal, including humans, domestic and farm animals, and zoo, sports, or pet animals, such as dogs, cats, cattle, horses, sheep, pigs, goats, rabbits, ferrets, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which a molecule that binds BOC or CDO of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a BOC/CDO hedgehog antagonist) to a mammal. The components of the liposome are commonly arranged in a bilayer formation, similar to the lipid arrangement of biological membranes.

A "small molecule" or "small organic molecule" is defined herein to have a molecular weight below about 500 Daltons.

An "effective amount" of a BOC/CDO hedgehog antagonist agent is an amount sufficient to inhibit, partially or entirely, hedgehog signaling that is at least in part dependent upon simulation from hedgehog. Alternatively, an effective amount of BOC/CDO hedgehog antagonist is an amount sufficient to reduce the rate of proliferation of a cell and/or rate of survival of a cell that is expressing or overexpressing hedgehog. An "effective amount" may be determined empirically and in a routine manner, in relation to this purpose.

The term "therapeutically effective amount" refers to a BOC/CDO hedgehog antagonist or other drug effective to "treat" a disease or disorder in a subject or mammal. In the case of hedgehog signaling, the therapeutically effective amount of the drug will restore aberrant hedgehog signaling to normal physiological levels; reduce the tumor size; inhibit (i.e., slow to some extent and preferably stop) the infiltration of tumor cells into peripheral tissue or organs; inhibit (i.e., slow to some extent and preferably stop) tumor metastasis; inhibit, to some extent, tumor growth; and/or relieve to some extent one or more of the symptoms associated with the tumor or cancer. See the definition herein of "treating". To the extent the drug may prevent growth and/or kill existing cancer cells, it may be cytostatic and/or cytotoxic.

A "growth inhibitory amount" of a BOC/CDO hedgehog antagonist is an amount capable of inhibiting the growth of a cell, especially tumor, e.g., cancer cell, either in vitro or in vivo. For purposes of inhibiting neoplastic cell growth, such an amount may be determined empirically and in a routine manner.

A "cytotoxic amount" of a BOC/CDO hedgehog antagonist is an amount capable of causing the destruction of a cell, especially a tumor cell, e.g., cancer cell, either in vitro or in vivo. For purposes of inhibiting neoplastic cell growth may be determined empirically and in a routine manner.

The term "anti-BOC antibody" is used in the broadest sense and specifically covers, for example, anti-BOC monoclonal antibodies (including agonist and neutralizing antibodies), anti-BOC antibody compositions with polyepitopic specificity, polyclonal antibodies, single chain anti-BOC antibodies, multispecific antibodies (e.g., bispecific) and antigen binding fragments (see below) of all of the above enumerated antibodies as long as they exhibit the desired biological or immunological activity. The term "anti-CDO antibody" is used in the broadest sense and specifically covers, for example, anti-CDO monoclonal antibodies (including antagonist and neutralizing antibodies), anti-CDO antibody compositions with polyepitopic specificity, polyclonal antibodies, single chain anti-CDO antibodies, multispecific antibodies (e.g., bispecific) and antigen binding fragments (see below) of all of the above enumerated antibodies as long as they exhibit the desired biological or immunological activity.

The term "immunoglobulin" (Ig) is used interchangeably with antibody herein.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant dmain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the approximately 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about Kabat residues 24-34 (L1), 50-56 (L2) and 89-97 (L3) in the $V_L$, and around about Kabat residues 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. around about Chothia residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681, (Elsevier, N.Y., 1981)), recombinant DNA methods (see, e.g., U.S. Pat. No. 4,816, 567), phage display technologies (see, e.g., Clackson et al., *Nature*, 352:624-628 (1991); Marks et al., *J. Mol. Biol.*, 222: 581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/ 34096; WO 1996/33735; WO 1991/10741; Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No.5,545,807; WO 1997/17852; U.S. Pat. Nos. 5,545,807; 5,545,806; 5,569,825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, *Proc. Natl. Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al, *Nature* 332:323-329 (1988); and Presta, *Curr. Op. Struct. Biol.* 2:593-596 (1992).

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein En*2, 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain ($C_H 1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

A "BOC/CDO hedgehog antagonist" is a molecule that antagonizes (e.g., neutralizes or impedes) the native or natural function of a hedgehog polypeptide or hedgehog signaling component, including, for example (i) by blocking the ability of hedgehog to transduce a signal, such as by blocking a native hedgehog ligand (e.g., Shh, Dhh, Ihh) from binding to a receptor, (ii) by blocking a hedgehog receptor (e.g., ptch-1, ptch-2, Smo, etc.) from transmitting to a downstream component in the hedgehog signaling pathway, (iii) by blocking the potentiating or stimulatory activity of a positive regulatory hedgehog signaling component (e.g., CDO), or (iv) by activating or enhancing the repressive activity of a negative hedgehog signaling regulatory component (e.g., BOC). The term expressly includes (1) "BOC hedgehog antagonists," further defined as BOC polypeptides (including chimeric BOC polypeptides), and certain (i.e., those that do not diminish the binding between BOC and hedgehog) anti-BOC antibodies, BOC-binding antibody fragments thereof, (2) "CDO antagonists", including anti-CDO antibodies, CDO-binding antibody fragments, antagonist CDO chimeric polypeptides, CDO binding oligopeptides, CDO sense/antisense nucleic acid, CDO binding small organic molecules, CDO RNAi and/or (3) any combination of the molecules of (1) or (2). A "CDO antagonist polypeptide" includes an anti-CDO antibody, an antagonist CDO chimeric polypeptide and a CDO binding oligopeptide. Methods for identifying BOC hedgehog antagonists and CDO antagonists may comprise contacting such a polypeptide, including a cell expressing it, with a candidate agonist or antagonist molecule and measuring a detectable change in one or more biological activities normally associated with such polypeptide.

An "interfering RNA" or RNAi is RNA of 10 to 50 nucleotides in length which reduces expression of a target gene, wherein portions of the strand are sufficiently complementary (e.g. having at least 80% identity to the target gene). The method of RNA interference refers to the target-specific suppression of gene expression (i.e., "gene silencing"), occurring at a post-transcriptional level (e.g., translation), and includes all posttranscriptional and transcriptional mechanisms of RNA mediated inhibition of gene expression, such as those described in P. D. Zamore, *Science* 296: 1265 (2002) and Hannan and Rossi, *Nature* 431: 371-378 (2004). As used herein, RNAi can be in the form of small interfering RNA (siRNA), short hairpin RNA (shRNA), and/or micro RNA (miRNA).

Such RNAi molecules are often a double stranded RNA complexes that may be expressed in the form of separate complementary or partially complementary RNA strands. Methods are well known in the art for designing double-stranded RNA complexes. For example, the design and synthesis of suitable shRNA and siRNA may be found in Sandy et al, *BioTechniques* 39: 215-224 (2005).

An "RNA coding region" is a nucleic acid that can serve as a template for the synthesis of an RNA molecule, such as a double-stranded RNA complex. Preferabley, the RNA coding region is a DNA sequence.

A "small interfering RNA" or siRNA is a double stranded RNA (dsRNA) duplex of 10 to 50 nucleotides in length which reduces expression of a target gene, wherein portions of the first strand is sufficiently complementary (e.g. having at least 80% identity to the target gene). siRNAs are designed specifically to avoid the anti-viral response characterized by elevated interferon synthesis, nonspecific protein synthesis inhibition and RNA degradation that oftern results in suicide or death of the cell associated with the use of RNAi in mammalian cells. Paddison et al, *Proc Natl Acad Sci USA* 99(3): 1443-8. (2002).

The term "hairpin" refers to a looping RNA structure of 7-20 nucleotides.

A "short hairpin RNA" or shRNA is a single stranded RNA 10 to 50 nucleotides in length charactertized by a hairpin turn which reduces expression of a target gene, wherein portions of the RNA strand are sufficiently complementary (e.g. having at least 80% identity to the target gene).

The term "stem-loop" refers to a pairing between two regions of the same molecule base-pair to form a double helix that ends in a short unpaired loop, giving a lollipop-shaped structure.

A "micro RNA" (previously known as stRNA) is a single stranded RNA of about 10 to 70 nucleotides in length that are initially transcribed as pre-miRNA characterized by a "stem-loop" structure, which are subsequently processed into mature miRNA after further processing through the RNA-induced silencing complex (RISC).

A "BOC binding oligopeptide" or a "CDO binding oligopeptide" is an oligopeptide that binds, preferably specifically, to a BOC polypeptide or a CDO polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. *Proc. Natl. Acad. Sci. USA*, 87:6378 (1990); Lowman, H. B. et al. *Biochemistry*, 30:10832 (1991); Clackson, T. et al. *Nature*, 352: 624 (1991); Marks, J. D. et al., *J. Mol. Biol.*, 222:581 (1991); Kang, A. S. et al. *Proc. Natl. Acad. Sci. USA*, 88:8363 (1991), and Smith, G. P., *Current Opin. Biotechnol.*, 2:668 (1991).

A BOC/CDO hedgehog antagonist "which binds" a target antigen of interest, e.g. hedgehog, BOC or CDO, is one that binds the target with sufficient affinity so as to be a useful diagnostic, prognostic and/or therapeutic agent in targeting a cell or tissue expressing the antigen, and does not significantly cross-react with other proteins. The extent of binding to a non desired marker polypeptide will be less than about 10% of the binding to the particular desired target, as determinable by common techniques such as fluorescence activated cell sorting (FACS) analysis or radioimmunoprecipitation (RIA).

Moreover, the term "specific binding" or "specifically binds to" or is "specific for" a particular hedgehog, BOC polypeptide or CDO polypeptide or an epitope thereof, means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In one embodiment, such terms refer to binding where a molecule binds to a particular polypeptide or epitope on a particular polypeptide without substantially binding to any other polypeptide or polypeptide epitope. Alternatively, such terms can be described by a molecule having a Kd for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or greater.

A BOC/CDO hedgehog antagonist that "inhibits the growth of tumor cells expressing a hedgehog BOC polypeptide or CDO polypeptide" or a "growth inhibitory" amount of any such molecule is one which results in measurable growth inhibition of cancer cells expressing hedgehog and/or underexpressing the BOC polypeptide or CDO polypeptide, respectively. Preferred compositions for use in treatment comprise growth inhibitory amounts of at least one type of BOC/CDO hedgehog antagonist (e.g., BOC polypeptide, anti-CDO antibody), so as to inhibit growth of tumor cells by greater than 20%, preferably from about 20% to about 50%, and even more preferably, by greater than 50% (e.g., from about 50% to about 100%) as compared to the appropriate control. In one embodiment, growth inhibition can be measured at a molecule concentration of about 0.1 to 30 µg/ml or about 0.5 nM to 200 nM in cell culture, where the growth inhibition is determined 1-10 days after exposure of the tumor cells to the antibody. Growth inhibition of glioma tumor cells in vivo can be determined in various ways such as is described in the Experimental Examples section below. An amount of any of the above molecules of this paragraph is growth inhibitory in vivo if administration of such molecule at about 1 µg/kg to about 100 mg/kg body weight results in reduction in tumor size or tumor cell proliferation within about 5 days to 3 months from the first administration of the antibody, preferably within about 5 to 30 days.

A BOC/CDO hedgehog antagonist which "induces apoptosis" is one which induces programmed cell death of a glioma tumor cell as determined by binding of annexin V, fragmentation of DNA, cell shrinkage, dialation of endoplasmic reticulum, cell fragmentation, and/or formation of membrane vesicles (called apoptotic bodies). The cell is usually one which overexpresses a hedgehog polypeptide. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cells in an annexin binding assay.

A BOC/CDO hedgehog antagonist which "induces cell death" is one which causes a viable tumor or cancer cell to become nonviable. Such a cell is one which expresses a hedgehog polypeptide, preferably overexpresses it, underexpresses a BOC polypeptide and/or overexpresses a CDO polypeptide, as compared to a non-diseased cell. The BOC polypeptide or CDO polypeptide may be a transmembrane polypeptide expressed on the surface of such cancer cell or may be a polypeptide that is produced and secreted by such a cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. The ability to induce cell death can be assessed relative to untreated cells by suitable techniques, such as loss of membrane integrity as evaluated by uptake of propidium iodide (PI), trypan blue (see Moore et al. *Cytotechnology* 17:1-11 (1995)) or 7AAD. Preferred cell death-inducing BOC/CDO hedgehog antagonists are those which induce PI uptake in the PI uptake assay in BT474 cells.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al, *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

A "BOC-deficient tumor or cancer" and/or "CDO-hyperactive tumor or cancer optionally produces insufficient levels of BOC polypeptide or excessive levels of CDO polypeptide, respectively, on the surface of cells thereof, such that hedgehog signaling is active or hyperactive, such that a BOC hedgehog antagonist or CDO antagonist can bind thereto or otherwise target and have a therapeutic effect with respect to the tumor.

In another embodiment, a "BOC-deficient tumor or cancer" and/or "CDO-hyperactive tumor or cancer" optionally produces and secretes insufficient levels of BOC polypeptide, or excessive levels of CDO polypeptide, respectively, such that hedgehog signaling is active or hyperactive, and a BOC hedgehog antagonist and/or CDO antagonist can bind thereto or otherwise target and have a therapeutic effect with respect to the cancer.

A tumor that "overexpresses" hedgehog or in which hedgehog signaling is "hyperactive" is one which has significantly higher levels of hedgehog at the cell surface thereof, or that produces and secretes, compared to a noncancerous cell of the same tissue type. Such overexpression may result from gene amplification or by increased transcription or translation. Various diagnostic or prognostic assays that measure enhanced expression of hedgehog resulting in increased levels at the cell surface or that which is secreted, such as immunohistochemistry assay using anti-hedgehog antibodies, FACS analysis, etc. Alternatively, the levels of hedgehog-encoding nucleic acid or mRNA can be measured in the cell, e.g., via fluorescent in situ hybridization using a nucleic acid based probe corresponding to a hedgehog-encoding nucleic acid or the complement thereof, (FISH; see WO98/45479 published October, 1998), Southern blotting, Northern blotting, or polymerase chain reaction (PCR) techniques, such as real time quantitative PCR (RT-PCR). Alternatively, hedgehog polypeptide overexpression is determinable by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). In addition to the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the therapeutic agent.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include hydroxyureataxanes (such as paclitaxel and doxetaxel) and/or anthracycline antibiotics; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylomithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY 117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell, especially a hedgehog overexpressing of BOC-underexpressing cell, either in vitro or in vivo. Thus, the growth inhibitory agent may be one which significantly reduces the percentage of hedgehog-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes or hydroxyureataxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). These molecules promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-ββ; platelet-growth factor; transforming growth factors (TGFs) such as TGF-α and TGF-β; insulin-like growth factor-I and -II; erythropoietin (EPO); osteoinductive factors; interferons such as interferon -α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

"Adenocarcinoma" refers to a malignant tumor originating in the glandular epithelium.

"Mesenchymal cells" are cells of mesncymal original including fibroblasts, stromal cells, smooth muscle cells, skeletal muscle cells, cells of osteogenic origin such as chondrocytes, cells of hematopoietic origin such as monocytes, macrophages, lymphocytes, granulocytes and cells of adipose origin such as adipocytes.

"Angiogenesis" is the formation of blood vessels, including both the formation of a new vasculature or alteration of an existing vascular system, which benefits tissue perfusion. This includes both the formation of new vessels by sprouting of endothelial cells from existing blood vessels or the remodeling of existing vessels to alter size, maturity, direction of flow properties to improve blood perfusion of tissue. While the latter process is sometimes referred more specifically as "arterogenesis", both processes are enveloped by the definition envisioned herein. Angiogenesis is a multistep process in which endothelial cells focally degrade and invade through their own basement membrane, migrate through interstitial stroma toward an angiogenic stimulus, proliferate proximal to the migrating tip, organize into blood vesels, and reattach to newly synthesized basement membrane. Folkman et al., *Cancer Res.* 43: 175-203 (1985).

"Basal cell carcinoma" refers to a variety of clinical and histological forms of cancers skin tissues such as nodular-ulcerative, superficial, pigmented, morphealike, fibroepithelioma and nevoid syndrome.

"Burn wounds" are lesions in the skin resulting from exposure to heat or chemical agents.

"Carcinoma" refers to a malignant growth derived from epithelial cells that tends to metastasize to other areas of the body. Examples include "basal cell carcinoma"—an epithelial tumor of the skin that, while seldom metastasizing, can result in local invasion and destruction; "squamous cell carcinoma"—tumors arising from squamous epithelium and having cuboid cells; "carcinosarcoma"—malignant tumors comprising both carcinomatous and sarcomatous tissues; "adenocystic carcinoma"—tumors characterized by large epithelial masses containing round gland-like spaces or cysts, frequently containing mucus, that are bordered by layers of epithelial cells;—"epidermoid carcinoma"—see squamous cell carcinoma; "nasopharyngeal carcinoma"—malignant tumor arising in the epithelial lining of the space behind the nose; "renal cell carcinoma"—tumor in the renal parenchyma composed of tubular cells in varying arrangements. Additional carcinomatous epithelial growth include "papillomas", which are benign tumors derived from the epithelium and having papillomavirus as a causative agent; and "epidermoidomas", which are cerebral of meningeal tumors formed by inclusion of ectodermal elements at the time of closure of the neural groove.

"Corium" or "dermis" refers to the layer of the skin deep to the epidermis, consisting of a dense bed of vascular connective tissue, and containing the nerves and terminal organs of sensations. The hair roots, and sebaceous and sweat glands are structures of the epidermis which are deeply embedded in the dermis.

"Dermal skin ulcers" refer to lesions on the skin cause by superficial loss of tissue, usually with inflammation. Dermal skin ulcers that can be treated by the method of the present invention include decubitus ulcers, diabetic ulcers, venous stasis ulcers and arterial ulcers. Decubitus wounds are chronic ulcers resulting from the application of pressure to the skin for extended periods of time. These type of wounds are also referred to as bedsores or pressure sores. Venous statis ulcers result from the stagnation of blood or other fluids from defective veins. Arterial ulcers refer to necrotic skin in the area around arteries having poor blood flow.

"Epithelia," "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithelial tissue includes: olfactory epithelium—the pseudostratified epithelium lining the olfactory region of the nasal cavity, and containing the receptors for the sense of smell; glandular epithelium—the epithelium composed of secreting cells squamous epithelium; squamous epithelium—the epithelium comprising one or more cell layers, the most superficial of which is composed of flat, scalelike or platelike cells. Epithelium can also refer to transitional epithelium, like that which is characteristically found lining hollow organs that are subject to great mechanical change due to contraction and distention, e.g., tissue which represents a transition between stratified squamous and columnar epithelium.

"Epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secret sweat, and are situated in the corium or subcutaneous tissue.

"Epidermis" refers to the protective outermost and nonvascular layer of the skin.

"Excisional wounds" include tears, abrasions, cuts, punctures or lacerations in the epithelial layer of the skin and may extend into the dermal layer and deeper, and result from surgical procedures or accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hedgehog" or "hedgehog polypeptide" (Hh) is used herein to refer generically to any of the mammalian homologs of the *Drosophila* hedgehog, i.e., sonic hedgehog (sHh), desert hedgehog (dHh) or Indian hedgehog (IHh). The term may be used to describe protein or nucleic acid.

The terms "hedgehog signaling pathway", "hedgehog pathway" and "hedgehog signal transduction pathway" as used herein, interchangeably refer to the signaling cascade mediated by hedgehog and its receptors (e.g., patched, patched-2) and which results in changes of gene expression and other phenotypic changes typical of hedgehog activity. The hedgehog pathway may be activated in the absence of hedgehog through activation of a downstream component (e.g., overexpression of Smoothened or transfections with Smoothened or Patched mutants to result in constitutive activation with activate hedgehog signaling in the absence of hedgehog). The transcription factors of the Gli family are often used as markers or indicators of hedgehog pathway activation.

The term "Hh signaling component" refers to gene products that participate in the Hh signaling pathway. An Hh signaling component frequently materially or substantially affects the transmission of the Hh signal in cells or tissues, thereby affecting the downstream gene expression levels and/or other phenotypic changes associated with hedgehog pathway activation.

Each Hh signaling component, depending on their biological function and effects on the final outcome of the downstream gene activation or expression, can be classified as either positive or negative regulators. A positive regulator is an Hh signaling component that positively affects the transmission of the Hh signal, i.e., stimulates downstream biological events when Hh is present. A negative regulator is an Hh signaling component that negative affects the transmission of the Hh signal, i.e. inhibits downstream biological events when Hh is present.

The term "hedgehog gain-of-function" refers to an aberrant modification or mutation of a hedgehog signaling component (e.g., ptch, Smo, Fused, Su(fu), Cos-2, etc.) or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptch gene product to regulate the level of expression of the transcription activation factors Gli1, Gli2 and/or Gli3. The term "hedgehog gain-of-function" is also used herein to refer to any similar cellular phenotype (e.g., exhibiting excess proliferation) that occurs due to an alteration anywhere in the hedgehog singal transduction pathway, including, but not limited to, a modification or mutation of hedgehog itself. For example, a tumor cell with an abnormally high proliferation rate to activation of the hedgehog signaling pathway would have a "hedgehog gain-of-function" phenotype, even if hedgehog is not mutated in that cell.

"Internal epithelial tissue" refers to tissue inside the body that has characteristics similar to the epidermal layer of the skin (e.g., the lining of the instestine).

"Keratosis" refers to a proliferative skin disorder characterized by hyperplasia of the horny layer of the epidermis. Example keratotic disorders include: keratosis follicularis, keratosis palmaris et plantaris, keratosis pharyngea, keratosis pilaris, and actinic keratosis.

"Lamellated bodies" refers to a subcellular structure found in lung cells that are producing surfactants. Lamellated bodies are believed to be the source of lung surfactant biosynthesis.

The term "overexpression" as used herein, refers to cellular gene expression levels of a tissue that is higher than the normal expression levels for that tissue.

The term "patched loss-of-function" refers to an aberrant modification or mutation of a ptch gene, or a decreased expression level of the gene, which results in a phenotype that resembles contacting the cell with a hedgehog protein, e.g., aberrant activation of a hedgehog pathway. The loss-of-function may include a loss of the ability of the ptch gene product to regulate the expression level of the transcription activation factors Gli1, Gli2 and/or Gli3.

The term "proliferating" and "proliferation" refer to a cell or cells undergoing mitosis.

The term "proliferative skin disorder" refers to any disease/disorder of the skin marked by unwanted or aberrant proliferation of cutaneous tissue. Such conditions are typically characterized by epidermal proliferation or incomplete cell differentiation, and include, for example, X-linked ichthyosis, psoriasis, atopic dermatitis, allergic contact dermatitis, epidermolyitic hyperkeratosis, and seborrheic dermatitis. For example, epidermodysplasia is a form of faulty development of the epidermis. Another example is "epidermolysis", which refers to a loosened state of the epidermis with formation of blebs and bulae either spontenously or at the site of the trauma.

"Psoriasis" refers to a hyperproliferative skin disorder that alters the skin's regulatory mechanisms. In particular, lesions are formed which involve primary and secondary alternations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorophonuclear leukocyte infiltration into the epidermis layer resulting in an increase in the basal cell cycle. Additionally, hyperkeratotic and parakeratotic cells are present.

"skin" refers to the outer protective covering of the body, consisting of the corium and the epidermis, including the sweat and sebaceous glands, as well as hair follicle structures.

"small cell carcinoma" refers to malignant neoplasms of the bronchus. Cells of such tumors have endocrine-like characteristics and may secrete one or more of a wide range of hormones, especially regulatory peptides like bombesin.

The term "smoothened gain-of-function" refers to an aberrant modification or mutation of a Smo gene, or in the ability of a ptch gene product to bind to Smo and thereby suppress hedgehog signaling, which results in a phenotype that resembles activating the hedgehog pathway with hedgehog, e.g., aberrant activation of a hedgehog pathway.

"Urogenital" refers to the organs and tissues of the urogenital tract, which includes among other tissues, the prostate, ureter, kidney, and bladder. A "urogenital cancer" is a cancer of a urogenital tissue.

TABLE 1

| Reference | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the reference polypeptide) = 5 dividedby 15 = 33.3%

TABLE 2

| Reference | XXXXXXXXXX | (Length = 10 amino acids) |
| Comparison Protein | XXXXXYYYYYZZYZ | (Length = 15 amino acids) |

% amino acid sequence identity = (the number of identically matching amino acid residues between the two polypeptide sequences as determined by ALIGN-2) divided by (the total number of amino acid residues of the reference polypeptide) = 5 divided by 10 = 50%

TABLE 3

| Reference-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the reference-DNA nucleic acid sequence) = 6 divided by 14 = 42.9%

TABLE 4

| Reference-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the reference-DNA nucleic acid sequence) = 4 divided by 12 = 33.3%

III. Hedgehog Antagonist Methods

In one embodiment, the present invention relates to methods of modulating a differentiated state, survival, and/or proliferation of a cell.

As hedgehog is known to stimulate angiogenesis, it follows based on the teachings herein that BOC and CDO, which have opposite effects on hedgehog signaling activity, would have opposite effects on angiogeneis. Thus, BOC polypeptides would inhibit, while CDO polypeptides would stimulate angiogenesis, particularly when some level of hedgehog activity is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these diseases.

Diseases associated with or resulting from angiogenesis include: ocular neovasscular disease, age-related macular degeneration, diabetic retinopathy, retinopathy of prematurity, corneal graft rejection, neovascular glaucoma, retrolental fibroplasias, epidemic keratoconjuctivitis, Vitamin A deficiency, contact lens overwear, atopic keratitis, superior limbic keratitis, pterygium keratitis sicca, Sjogren's syndrome, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's granulomatosis, sacroidosis, scleritis, Stevens-Johnson syndrome, pemphigoid radial keratotomy, corneal graph rejection, rheumatoid arthritis, systemic lupus, polyarteritis, trauma, Wegener's granulomatosis, sarcoidosis, scleritis, Stevens-Johnson syndrome, pemphigoid radial keratotomy, corneal graph rejection, rheumatoid arthritis, osteoarthritis chronic inflammation (e.g., ulcerative colitis or Crohn's disease), hemangioma, Osler-Weber Rendu disease, and hereditary hemorrhagic telangiectasis.

Angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, osteosarcoma, and benign tumors such as acoustic neuroma, neurofibroma, trachoma and pyogenic granulomas. Angiogenic factors have been found associated with several solid tumors, and preventing angiogenesis could halt the growth of these tumors and the resultant damage to the animal due to the presence of the tumor. Angiogenesis is also associated with blood-born tumors such as leukemias, any of various actute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis in important in metastasis. Initially, angiogenesis is important in the vascularization of the tumor which allows cancerous cells to enter the blood stream and to circulate throughout the body. After the tumor cells have left the primary site, and have settled into the secondary, metastatic site, angiogenesis must occur before the new tumor can grow and expand. Therefore, prevention of angiogenesis could lead to the prevention of metastasis of tumors and possibly contain the neoplastic growth at the primary site.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

The BOC/CDO hedgehog antagonists of the invention are useful for the treatment and/or prevention of respiratory distress syndrome or other disorders resulting from inappropriate lung surface tension. Respiratory distress syndrome results from insufficient surfactant in the alveolae of the lungs. The lungs of vertebrates contain surfactant, a complex mixture of lipids and protein that causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface areas increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant in normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can also in adults, typically as a consequence of failure in surfactant biosynthesis.

Lung tissue of premature infants shows high activity of the hedgehog signaling pathway. Inhibition of this pathway using hedgehog antagonists increases the formation of lamellated bodies and increases the expression of genes involved in surfactant biosynthesis. Lamellar bodies are subsellular structures associated with surfactant biosynthesis. For these reasons, treatment of premature infants with a hedgehog antagonist should stimulate surfactant biosynthesis and ameliorate RDS. In cases where adult RDS is associated with hedgehog pathway activiation, treatment with BOC/CDO hedgehog antagonist should also be effective.

It is further contemplated that use of BOC/CDO hedgehog antagonists may be specifically targeted to disorders where the affected tissue and/or cells exhibit high hedgehog pathway activation. Expression of gli genes activated by the hedgehog signaling pathway, including gli-1, gli-2 and gli-3, most consistently correlate with hedgehog signaling across a wide range or tissues and disorders, while gli-3 is somewhat less so. The gli genes encode transcription factors that activate expression of many genes needed to elicit the full effects of hedgehog signaling. However, the Gli-3 transcription factors can also act as a repressor of hedgehog effector genes, and therefore, expression of gli-3 can cause a decreased effect of the hedgehog signaling pathway. Whether gli-3 acts as a transcriptional activator or repressor depends on post-translational events, and therefore it is expected that methods for detecting the activating form (versus the repressing form) of Gli-3 protein would also be a reliable measure of hedgehog pathway activation. The gli-1 gene is strongly expressed in a wide array of cancers, hyperplasias and immature lungs, and serves as a marker for the relative activation of the hedgehog pathway. In addition, tissues such as immature lung, that have high gli gene expression, are strongly affected by hedgehog inhibitors. Accordingly, it is contemplated that the detection of gli gene expression may be used as a powerful predictive tool to identity tissues and disorders that will particularly benefit from treatment with a hedgehog antagonist.

In preferred embodiments, gli-1 expression levels are detected, either by direct detection of the transcript or by detection of protein levels or activity. Transcripts may be detected using any of a wide range of techniques that depend primarily on hybridization or probes to the gli-1 transcripts or to cDNAs synthesized therefrom. Well known techniques include Northern blotting, reverse-transcriptase PCR and microarray analysis of transcript levels. Methods for detecting Gli protein levels include Western blotting, immunoprecipitation, two-dimensional polyacrylamide gel electrophoresis (2D SDS-PAGE —preferably compared against a standard wherein the position of the Gli proteins has been determined), and mass spectroscopy. Mass spectroscopy may be coupled with a series of purification steps to allow high-throughput indentification of many different protein levels in a particular sample. Mass spectroscopy and 2D SDS-PAGE can also be used to identify post-transcriptional modifications to proteins including proteolytic events, ubiquitination, phosphorylation, lipid modification, etc. Gli activity may also be assessed by analyzing binding to substrate DNA or in vitro transcriptional activation of target promoters. Gel shift assay, DNA footprinting assays and DNA-protein crosslinking assays are all methods that may be used to assess the presence of a protein capable of binding to Gli binding sites on DNA. *J. Mol. Med* 77(6):459-68 (1999); *Cell* 100(4): 423-34 (2000); *Development* 127(19): 4923-4301 (2000).

In certain embodiments, gli transcript levels are measured and diseased or disordered tissues showing abnormally high gli levels are treated with a BOC/CDO hedgehog antagonist. In other embodiments, the condition being treated is known to have a significant correlation with aberrant activation of the hedgehog pathwy, even though a measurement of gli expression levels is not made in the tissue being treated. Premature lung tissue, lung cancers (e.g., adeno carcinomas, broncoalveolar adenocarcinoma, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated gli-1 expression levels in certain cases. Accordingly, gli-1 expression levels are a powerful diagnostic device to determine which of these tissues should be treated with a BOC/CDO hedgehog antagonist. In addition, there is substantial correlative evidence that cancers of the urothelial cells (e.g., bladder cancer, other urogenital cancers) wil also have elevated gli-1 levels in certain cases. For example, it is known that loss of heterozygosity on chromosome 9q22 is common in bladder cancers. The ptch-1 gene is located at this position and ptch-1 loss of function is probably a partial cause of hyperproliferation, as in many other cancer types. Accordingly, such cancers would also show high gli expression and would be particularly amenable to treatment with a hedgehog antagonist.

Expression of ptch-1 and ptch-2 is also activated by the hedgehog signaling pathway, but not typically to the same extent as gli genes, and as a result are inferior to the gli genes as markers of hedgehog pathway activation. In certain tissues, only one of ptch-1 or ptch-2 is expressed although the hedgehog pathway is highly active. For example, in testicular development, desert hedgehog plays an important role and the hedgehog pathway is activated, but only ptc-2 is expressed. Accordingly, these genes may be individually unreliable as markers for hedgehog pathway activation, although simulatenous measurement of both genes is contemplated as a more useful indicator for tissues to be treated with a hedgehog antagonist.

Because gli is so ubiquitously expressed during hedgehog activation, any degree of gli overexpression should be useful in determining that a BOC/CDO hedgehog antagonist will be an effective therapeutic. In preferred embodiments, gli should be expressed at a level at least twice as high as normal. In particularly preferred embodiments, expression is four, six, eight or ten times as high as normal.

In light of the broad involvement of hedgehog signaling in the formation of ordered spatial arrangements of differentiated tissues in vertebrates, the BOC/CDO hedgehog antagonists of the present invention could be used in a process for generating and/or maintaining an array of different vertebrate tissue both in vitro and in vivo. The BOC/CDO hedgehog antagonist, whether inductive or anti-inductive with respect to proliferation or differentiation of a given tissue type, can be, as appropriate, any of the preparations described above.

The BOC/CDO hedgehog antagonists of the present invention are further applicable to cell culture techniques wherein reduction in hedgehog signaling is desirable. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once use of the present method may be in culture of neuronal stem cells, such as in the use of such cultures for the generation of new neurons and glia. These cultures can be contacted with BOC/CDO hedgehog antagonists in order to alter the rate of proliferation or neuronal stem cells in the culture and/or alter the rate of differentiation, or to maintain the integrity of a culture of certain terminally differentiated neuronal cells. In an exemplary embodiment, the subject method can be used to culture, certain neuron types (e.g., sensory neurons, motor neurons). Such neuronal cultures can be used as convenient assay systems as well as sources of implantable cells for therapeutic treatments.

The BOC/CDO hedgehog antagonists of the present invention are further applicable to intracerebral grafting, an emerging treatment for disorders of the central nervous system. For example, one approach to repairing damaged brain tissues involves the transplantation of cells from fetal or neonatal animals into the adult brain. Dunnett et al., *J. Exp. Biol.* 123: 265-289 (1987). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog antagonists employed in the present method to culture such stem cells can be to regulate differentiation of the uncommitted progenitor, or to regulate further restriction of the developmental fate of a committed progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic, sympathetic or parasympathetic neurons, as well as peptinergic and serotonergic neurons. The BOC/CDO hedgehog antagonist can be used alone, or in combination with other neurotrophic factors that act to more particularly enhance a particular differentiation fate of the neuronal progenitor cell.

In addition to use of the BOC/CDO hedgehog antagonists in combination with implantation of cell cultures, another aspect of the present invention relates to the therapeutic application of BOC/CDO hedgehog antagonists to regulate the growth state of neurons and other neuronal cells in both the central nervous system and the peripheral nervous system.

The ability of the hedgehog pathway component (e.g., ptch, hedgehog, and smoothened) to regulate neuronal differentiation during development of the nervous system and also presumably in the adult state indicates that in certain instances, the subject BOC/CDO hedgehog antagonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplated applications of the subject method to the treatment (e.g., prevention, reduction in severity, etc.) of neurological conditions deriving from: (i) acute, subacute, or chronic injury to the nervous system, including traumatic injury, chemical injury, vascular injury and deficits (such as the isehemia resulting from stroke), together with infectious/inflammatory and tumor-induced injury; (ii) aging of the nervous system, including Parkinson's disease, Huntington's chorea, amyotrophic lateral sclerosis and the like, as well as spinocerebellar degeneration; and (iv) chronic immunological diseases of the nervous system or affecting the nervous system, including multiple sclerosis.

As appropriate, the BOC/CDO hedgehog antagonists of the subject method can also be used in generating nerve prosthesis for the repair of central and peripheral nerve damage. In particular, where a crushed or severed axon is intubulated by the use of a prosthetic device, hedgehog antagonists can be added to the prosthetic device to regulate the rate of growth and regeneration of the dendritic processes. Exemplary nerve guidance channels are described in U.S. Pat. Nos. 5,092,871 and 4,955,892.

In another embodiment, the BOC/CDO hedgehog antagonists of the subject method can be used in the treatment of neoplastic or hyperplastic transformation such as may occur in the central nervous system. For instance, the BOC/CDO hedgehog antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In an alternative embodiment, the BOC/CDO hedgehog antagonists of the subject method can be used as part of a treatment regimen for malignant medulloblastoma and other primary CNS malignant neuroectodermal tumors. Medulloblastoma, a primary brain tumor, is the most common brain tumor in children. A medulloblastoma is a primitive neuroectodermal (PNET) tumor arising in the posterior fossa. They account for approximately 25% of all pediatric brain tumors. Histologically, they are small round cell tumors commonly arranged in a true rosette, but may display some differentiation to astrocytes, ependymal cells or neurons. PNETs may arise in other areas of the brain including the pineal gland (pineoblastoma) and cerebrum. Those arising in the supratentorial region generally have a worsened prognosis.

Medulloblastom/PNETs are known to recur anywhere in the CNS after resection, and can even metastasize to bone. Pretreatment evaluation should therefore include and examination of the spinal cord to exclude the possibility of "dropped metastases". Gadolinium-enhanced MRI has largely replaced myelography for this purpose, and CSF cytology is obtained postoperatively as a routine procedure.

In other embodiment, the BOC/CDO hedgehog antagonists of the subject method is used as part of a treatment program for ependymomas. Ependymomoas account for approximately 10% of the pediatric brain tumors in children. Grossly, they are tumors that arise from the ependymal lining of the ventricles and microscopically form rosettes, canals, and perivascular rosettes. In the CHOP series of 51 children reported with epenymomas, ¾ were histologically benign. Approximately ⅔ arose from the region of the $4^{th}$ ventricule. One third presented in the supratentorial region. Age at presentation peaks between birth and 4 years, as demonstrated by SEER data as well as date from CHOP. The median age is about 5 years. Because so many children with this disease are babies, they often require multimodal therapy.

In other embodiment, the BOC/CDO hedgehog antagonists of the subject method can be used in cell culture and therapeutic method relating to the generation and maintenance of non-neuronal tissue. Such uses are contemplated as a result of the involvement of hedgehog signaling components (e.g., ptc, hedgehog, smo, fused, su(fu), Cos-2, etc.) in morphogenic signals of other vertebrate organogenic pathways, such as endodermal patterning, and mesodermal and endodermal differentiation.

As hedgehog signaling, especially ptc, hedgehog, and smoothened, are involved in controlling the development of stem cells responsible for formation of the digestive tract, liver, lungs, and other organs derived from the primitive gut. Shh is the inductive signal from the endoderm to the mesoderm, which is critical to gut morphogenesis. Therefore, for example, the BOC/CDO hedgehog antagonists of the instant method can be employed for regulating the development and maintenance of an artificial liver that can have multiple metabolic functions of a normal liver. In an exemplary embodiment, the subject method can be used to regulate functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, the BOC/CDO hedgehog antagonists of the subject method can be employed therapeutically to regulate such organs after physical, chemical or pathological insult. For instance, therapeutics comprising BOC/CDO hedgehog antagonist can be used in liver repair subsequent to a partial hepactectomy.

In another embodiment, the subject method can be used to control or regulate the proliferation and/or differentiation of pancreatic tissue both in vivo and in vitro. The generation of the pancreas and small intestine from the embryonic gut depends on intercellular signaling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog (Shh). Apelqvist et al., Curr. Biol. 7: 801-4 (1997). The Shh gene is expressed throughout the embryonic bud endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. The Ipf1/Pdx1 was used to selectively express Shh in the developing pancreatic epithelium. The pancreatic mesoderm of Ipf1/Pdx1-Shh transgenic mice developed into smooth muscle and insterstitial cells of Cajal—cells which are characteristic of the intestine, rather than pancreatic mesenchyme and spleen. Apelqvist et al., supra. Also, pancreatic explants exposed to Shh underwent as similar expression of endodermally derived Shh controls the fate of adjacent mesoderm at different regions of the gut tube.

In another embodiment, BOC/CDO hedgehog antagonists are used to generate endodermal tissue from non-endodermal stem cells including mesenchymal cells and stem cells derived from mesodermal tissues. Exemplary mesodermal tissues from which stem cells may be isolated include skeletal muscle, cardiac muscle, kidney, cartilage and fat.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog and smoothened in the formation of ordered spatial arrangements of pancreatic tissues, the BOC/CDO hedgehog antagonists of the subject method could be used as part of a technique to generate and/or maintain such tissue both in vitro and in vivo. For instance, modulation of the function of hedgehog can be employed in both cell culture and therapeutic methods involving generation and maintenance of β-cells and possibly also from non-pancreatic tissue, such as in controlling the development and maintenance of tissue from the digestive tract, spleen, lungs, urogenital organs (e.g., bladder), and other organs which derive from the primitive gut.

In a specific embodiment, the BOC/CDO hedgehog antagonists of the present invention can be used in the treatment of hyperplastic and neoplastic disorders affecting pancreatic tissue, especially those characterized by aberrant proliferation of pancreatic cells. For instance, pancreatic cancers are marked by abnormal proliferation of pancreatic cells, which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, such as through using BOC/CDO hedgehog antagonists, can provide a means for more carefully controlling the characteristics of a cultured tissue. In an exemplary embodiment, the subject method can be used to augment production of prosthetic devise which require β-islet cells, such as may be used in the encapsulation devices described in, for example, as described in U.S. Pat. Nos. 4,892,538, 5,106, 627, 4,391,909 and 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature B-cells can be observed. By utilizing the subject hedgehog antagonists, the differentiaton path or proliferative index of the cells can be regulated.

Furthermore, manipulation of the differentiative state of pancreatic tissue can be utilized in conjunction with transplantation of artificial pancreas. For instance, manipulation of hedgehog function to affect tissue differentiation can be utilized as a means of maintaining graft viability.

The BOC/CDO hedgehog antagonists of the present invention may be used to regulate the regeneration of lung tissue, e.g., in the treatment of emphysema. It has been reported that Shh regulates lung mesenchymal cell proliferation in vivo. Bellusci et al., *Development* 124: 53 (1997).

The BOC/CDO hedgehog antagonists of the present invention may also be used as part of a treatment of lung carcinoma and adenocarcinoma, and other proliferative disorders involving the lung epithelia. It has been shown that Shh is expressed in human lung squamous carcinoma and adenocarcinoma cells. Fujita et al., *Biochem. Biophys. Res. Commun.* 238: 658 (1997). The expression of Shh was also detected in the human lung squamous carcinoma tissues, but not in the normal lung tissue of the same patient. They also observed that Shh stimulates the incorporation of BrdU into the carcinoma cells and stimulates their cell growth, while anti-Shh-H inhibited their cell growth. These results suggest that a ptc, hedgehog, and/or smoothened is involved in cell growth of such transformed lung tissue and thereore indicates that the subject can be used as part of a treatment of lung carcinoma and adenocarcinomas, and other proliferative disorders involving the lung epithelia.

The BOC/CDO hedgehog antagonists of the present invention, based on the involvement of hedgehog signaling in various tumors, or expression of hedgehog or its receptors in such tissues during development, can be treatment by the present method. Such tumors include, but are not limited to: tumors related to Gorlin's syndrome (e.g., medulloblastoma, meningioma, etc.), tumors evidence in ptc knock-out mice (e.g., hemangiona, rhabdomyosarcoma, etc.), tumors resulting from gli-1 amplification (e.g., glioblastoma, sarcoma, etc.), tumors resulting from Smo dysfunction (e.g., basal cell carcinoma, etc.), tumors connected with TRC8, a ptc homolog (e.g., renal carcinoma, thyroid carcinoma, etc.), Ext-1 related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.).

The BOC/CDO hedgehog antagonists of the present invention may also be used to treat several forms of cancer. These cancer include, but are not limited to: prostate cancer, bladder cancer, lung cancer (including small cell and non-small cell), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional cancer types include cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

In another embodiment, the BOC/CDO hedgehog antagonists of the present invention can be used in the in vitro generation of skeletal tissue, such as from skeletogenic stem cells, as well as the in vivo treatment of skeletal tissue deficiencies. The present invention particularly contemplated the use of BOC/CDO hedgehog antagonists to regulate the rate of chrondrogenesis and/or osteogenesis. By "skeletal tissue deficiency", it is meant a deficiency in bone or other sketal connective tissue at any site where it is desired to restore the bone or connective tissue, no matter how the deficiency originated, e.g., whether as a result of surgical intervention, removal of tumor, ulceration, implant, fracture, or other traumatic or degenerative conditions.

For example, one suitable method is the use of the BOC/CDO hedgehog antagonists of the present invention in a regimen for restoring cartilage function to connective tissue. Such methods are useful in, for example, the repair of defects or lesions in cartilage tissue which is the result of degenerative wear such as that which results in arthritis, as well as other mechnical derangements which may be caused by trauma to the tissue, such as a displacement of torn meniscus tissue, meniscectomy, a laxation of a joint by a torn ligament, malignment of joint, bone fracture, or by hereditary disease. The present reparative method is also useful for remodeling cartilage matrix, such as in plastic or reconstructive surgery, as well as periodontal surgery. The present method may also be applied to improving a previous procedure, for example, following surgical repair of meniscus, ligament, or cartilage. Furthermore, it may prevent the onset or exacerbation of degenerative disease if applied early enough after trauma.

In one embodiment of the present invention, the BOC/CDO hedgehog antagonists of the subject method comprises treating the afflicted connective tissue with a therapeutically effective amount of a BOC/CDO hedgehog antagonist, in order to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In another embodiment, the BOC/CDO hedgehog antagonists of the subject method can be used as part of a therapeutic intervention in the treatment of cartilage of a diarthroidal joint, such as a knee, an ankle, an elbow, a hip, a wrist, a knuckly or either a finger or toe, or a tempomandibular joint. The treatment can be directed to the meniscus of the joint, to the articular cartilage of the joint, or both. To further illustrate, the subject method can be used to treat a degenerative disorder or a knee, such as which might be the result of traumatic injury (e.g., a sports injury or excessive wear) or osteoarthritis. The subject antagonists may by administered as an injection into the joint with, for instance an arthroscopic needle. In some instances, the injected agent can be in the form of a hydrogel or other slow release vehicle described above in order to permit a more extended and regular contact of the agent with the treated tissue.

The present method may also be used in the field of cartilage transplantation and prosthetic device therapies. Because of the characteristics of cartilage and fibrocartilage vary between different tissues (e.g., articular, meniscal, ligaments, tendons, between two ends of same ligament or tendon, and between the superficial and deep parts of the tissue), problems arise when these tissues are surgically repaired after injury. The zonal arrangement of these tissues may reflect a gradual change in mechanical properties, and failure occurs when implanted tissue, which has not differentiated under those conditions, lacks the ability to appropriately respond. For example, when meniscal cartilage is used to repair anterior cruciate ligaments, the tissue undergoes a metaplasis to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al, Clin. Orthop. Relat. Red. 252: 129 (1990)), isolated chondrocytes (Grande et al., J. Orthop. Res. 7: 208 (1989); Takigawa et al., Bone Miner 2: 449 (1987)), and chondrocytes attached to natural or synthetic polymers (Walitani et al, J. Bone Jt. Surg. 71B:74 (1989); Vacanti et al., Plast. Resconstr. Surg. 88:753 (1991); von Schroeder et al., J. Biomed. Mater. Res. 25: 329 (1991); Freed et al., J. Biomed. Mater. Res. 27: 11 (1993); U.S. Pat. No. 5,041,138). For example, chondrocytes can be grown in culture on biodegradable, biocompatible highly porous scaffolds formed from polymers such as polyglycolic acid, polylactic acid, agarose gel, or other polymers that degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own affected body portion (e.g., ear, nose, etc.), or flexible matrices can be used which allow for manipulation at the time of implantation, as in a joint.

In another embodiment, implants may be contacted with the BOC/CDO hedgehog antagonists during certain stages of the culturing process in order to manage the rate of differentiation of chondrocytes and the formation of hypertrophic chondrocytes in the culture.

In another embodiment, the implanted device is treated with a BOC/CDO hedgehog antagonists in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, BOC/CDO hedgehog antagonists of the subject method are used to enhance attachment of prosthetic devices. To illustrate, the subject method can be used in the implantation of a periodontal prosthesis, wherein the treatment of the surrounding connective tissue stimulates formation of periodontal ligament about the prothesis.

In still further embodiments, the subject method can be employed as part of a regimen for the generation of bone (osteogenesis) at a site in an animal where such skeletal tissue is deficient. Indian hedgehog is particularly associated with the hypertrophic chondrocytes that are ultimately replaced by osteoblasts. For instance, administration of a BOC/CDO hedgehog antagonist of the present invention can be employed as part of a method for regulating the rate of bone loss in a subject. For example, preparations comprising hedgehog antagonists can be employed, for example, to control endochondral ossification in the formation of a "model" for ossification.

In yet another embodiment, a BOC/CDO hedgehog antagonist can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulated both early and late stages of spermatogenesis. Bitgood et al., Curr. Biol. 6: 298 (1996). In a preferred embodiment, the BOC/CDO hedgehog antagonist can be used as a contraceptive. In a similar fashion, BOC/CDO hedgehog antagonists of the subject method are potentially useful for modulating normal ovarian function.

The BOC/CDO hedgehog antagonists of the invention also may be used in the treatment (including prophylaxis) of disorders afflicting epithelial tissue, as well as in cosmetic uses. In general, the method can be characterized as including a step of administering to an animal an amount of a hedgehog antagonist effective to alter the growth state of the treated epithelial tissue. The mode of administration and dosage regimens will vary depending on the epithelial tissue(s) that is to be treated. For example, topical formulations will be preferred where the treated tissue is epidermal tissue, such as dermal or mucosal tissues.

The BOC/CDO hedgehog antagonists of the present invention, are further suitable for use in modulating or promoting wound healing. Specifically, "promoting wound healing" means a wound healing more quickly as a result of application of the treatment that a similar wound heals in the absence of the treatment. "Promotion of wound healing" can also mean that the method regulates the proliferation and/or growth of, inter alia, keratinocytes, or that the wound heals with less scarring, less wound contractions, less collagen deposition and more superficial surface area. In certain instances, "promotion of wound healing" can also mean that certain methods of wound healing have improved success rates, (e.g., the take rates of skin grafts), when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest of circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the BOC/CDO hedgehog antagonists of the subject method, the rate of proliferation of epithelial cells in and proximal to the wound can be controlled in order to accelerate closure of the wound and/or minimize the formation of scar tissue.

The BOC/CDO hedgehog antagonists of subject method can also be effective as part of a therapeutic regimen for treating oral and paraoral ulcers, e.g., resulting from radiation and/or chemotherapy. Such ulcers commonly develop within days afer chemotherapy or radiation therapy. These ulcers usually begin as small, painful irregularly shaped lesions usually covered by a delicate gray necrotic membrane and surrounded by inflammatory tissue. In many instances, lack of treatment results in the proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is also present with all its complicating factors. According to the present invention, a treatment for such ulcers that include application of a BOC/CDO hedgehog antagonist can reduce the abnormal proliferation and differentiation of the affected epithelium, helping to reduce the severity of subsequent inflammatory events.

The BOC/CDO hedgehog antagonists of the subject method can also be used to treat wounds resulting from dermatological diseases, such as lesions resulting from autoimmune disorders such as psoriasis and atopic dermatitis. Atopic dermatitis refers to skin trauma resulting from allergies associated with an immune response caused by allergens such as pollens, foods, dander, insect venoms and plant toxins.

In other embodiments, an antiproliferative preparation of the BOC/CDO hedgehog antagonists of the invention can be used to inhibit lens epithelial cell proliferation to prevent post-operative complications of extracapsular cataract extraction. Cataracts are an intractable eye disease and various studies on the treatment of cataracts have been made. However, at present, treatment is primarily obtained through surgery. Cataract surgeries have been applied for a long time and various operative methods have been examined. Extracapsular lense extraction has become the method of choice for removing cataracts. The major medical advantages of this technique over the intracapsular extraction is lower incidence of aphakic cystoid macular edema and retinal detachment. Extracapsular extractionis also required for implantation of posterior chamber-type intraocular lenses, which are now considered to be the lenses of choice in most cases.

However, a disadvantage of extracapsular cataract extraction is the high incidence of posterior lens opacification, often called after-cataract, which can occur in up to 50% of cases within three years of surgery. After-cataract is caused by proliferation of equatorial and anterior capsule lens epithelial cells that remain after extracapsular lens extraction. These cells proliferate to cause Sommerling rings, and along with fibroblasts, which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution continaing a hedgehog antagonist preparation into the anterior chamber of the eye after lens removal. Furthermore, the solution can be osmotically balanced to provide a minimally effective dosage when instilled into the anterior chamber of the eye, thereby inhibiting subcapsular epithelial growth with some specificity.

The BOC/CDO hedgehog antagonists of the invention may also be used in the treatment of corneopathies marked by corneal epithelial cell proliferation, as for example in ocular epithelial disorders such as eptithelial downgrowth or squamous cell carcinomas of the ocular surface. Hedgehog proteins have been shown to regulate mitogenesis and photoreceptor differentiation in the vertebrate retina (Levine et al., *J. Neurosci.* 17: 6277 (1997)), and Ihh is a candidate factor from the pigmented epithelium to promote retinal progenitor proliferation and photoreceptor differentiation. Likewise, Jensen et al., *Development* 124: 363 (1997), demonstrated that treatment of cultures of perinatal mouse retinal cells with the amino-terminal fragment of Shh protein results in an increase in the proportion of cell that incorporate bromodeoxyuridine, in total cell numbers, and in rod photoreceptors, amacrine cells and Müller glial cells. This suggests that Shh promotes the proliferation of retinal precursor cells, which means that the BOC/CDO hedgehog antagonists of the present invention would be expected to modulate such Shh-mediated proliferation. Thus, the subject method can be used in the treatment of proliferative diseases of retinal cells and regulate photoreceptor differentiation.

Yet another embodiment of the invention relates to the use of the BOC/CDO hedgehog antagonists of the subject method to control hair growth. Hair is basically composed of keratin, a tough and insoluble protein. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catgen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, method for increasing or reducing hair growth can be carried out by potentiating or inhibiting, respectively, the proliferation of these stem cells.

In certain embodiments, the BOC/CDO hedgehog antagonists of the subject method can be employed as a way of reducing the growth of human hair as opposed to its convention removal by cutting, shaving, or depilation. For instance, BOC/CDO hedgehog antagonists can be used in the treatment of trichosis characterized by abnormally rapid growth of hair, e.g., hypertrichosis. In an exemplary embodiment, BOC/CDO hedgehog antagonists can be used to manage hirsutism, a disorder marked by abnormal hairiness. The subject method can also provide a process for extending the duration of depilation.

Moreover, because a BOC/CDO hedgehog antagonist will often be cytostatic to epithelial cells, rather than cytotoxic, they can be used to protect hair follicle cells from cytotoxic agents that are required progression into S-phase of the cell-cycle for efficacy, e.g., radiation-induced death. As a result, treatment by BOC/CDO hedgehog antagonists can provide protection by causing the hair follicle cells to become quite quiescent, e.g., by inhibiting the cells from entering S-phase, and thereby preventing the follicle cells from undergoing mitotic catastrophe or programmed cells death. For example, BOC/CDO hedgehog antagonists can be used for patients undergoing chemo- or radiation-therapies that ordinarily result in hair loss. By inhibiting cell-cycle progression during such therapies, the subject treatment can protect hair follicle cells from death, which might otherwise result from activation of cell death programs. After the therapy has concluded, the instant method can also be removed with concomitant relief of the inhibition of follicle cell proliferation.

The BOC/CDO hedgehog antagonists of the present invention can also be used in the treatment of folliculitis, such as folliculitis decalvans, folliculitis ulerythematosis reticulate or keloid folliculitis. For example, a cosmetic preparation of a BOC/CDO hedgehog antagonist can be applied topically in the treatment of pseudofolliculitis, a chronic disorder occurring most often in the submandibular region of the neck and associated with shaving, the characteristic lesions of which are erythematous papules and pustules containing buried hairs.

In other embodiments, the BOC/CDO hedgehog antagonists can be used as a way of increasing the growth of human hair. Sato et al., *J. Clin. Invest.* 104: 855-864 (1999) reported that upregulation of Shh activity in postnatal skin functions as a biologic switch that induces resting hair follicles to enter anagen with consequent hair growth. Sato et al., used an adenovirus vector, AdShh, to transfer the murine Shh cDNA to skin of postnatal day 19 C57BL/6 mice. The treated skin showed increased mRNA expression of Shh, Patched, Smo and Gli-1. In mice receiving AdShh, but not in controls, acceleration into anagen was evident, since hair follicle size and melanogenesis increased and the hair-specific keratin ghHb-1 and the melanin synthesis-related tyrosinase mRNAs accumulated. Finally, C57BL/6 mice showed marked acceleration of the onset of new hair growth in the region of AdShh administration to skin weeks after treatment, but not in control vector-treated or untreated areas. After 6 months, AdShh-treated skin showed normal hair and normal skin morphology. Thus, the BOC/CDO hedgehog antagonists of the present invention may be useful to regulate or modulate Shh-induced hair growth.

In another aspect of the invention, the subject method can be used to regulate the induction of Shh induced differentiation and/or inhibit proliferation of epithelially derived tissue. Thus, the BOC/CDO hedgehog antagonists of the present invention can provide for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For example, the pharmaceutical preparations of the BOC/CDO hedgehog antagonists of the invention are intended for the treatment of hyperplastic conditions, such as keratosis, as well as for the treatment of neoplastic epidermal conditions such as those characterized by a high proliferation rate for various skin cancers, e.g., squamous cell carcinoma. The BOC/CDO hedgehog antagonists of the invention can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the BOC/CDO hedgehog antagonists of the present invention are suitable for the treatment of dermatological ailments linked to keratinization disorders causing abnormal proliferation of skin cells, which disorder may be marked by either inflammatory or non-inflammatory components. BOC/CDO hedgehog antagonists that promote quiescence or differentiation can be used to treat varying forms of psoriasis, e.g., cutaneous, mucosal or ungual. Psoriasis, as described above, is typically characterized by epidermal keratinocytes that display marked proliferative activation and differentiation along a "regenerative" pathway. Treatment with such BOC/CDO hedgehog antagonist according to the present method can be used to reverse the pathological epidermal activation and can provide a basis for sustained remission of the disease.

A variety of other keratotic lesions are also candidates for treatment with the BOC/CDO hedgehog antagonists of the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a BOC/CDO hedgehog antagonist composition in amounts sufficient to inhibit hyperproliferation of epidermal/epidermoid cells of the lesion.

Acne represents yet another dermatologic ailment which may be treated by the BOC/CDO hedgehog antagonists of the subject method. Acne vulgaris, a multifactor disease most commonly occurring in teenagers and young adults, is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative BOC/CDO hedgehog antagonist, particularly topical preparations, may be useful for preventing the transitional features of the ducts, e.g., hypercornification, which lead to lesion formation. The subject treatment may further include, for example, antibiotics, retinoids and antiandrogens.

The BOC/CDO hedgehog antagonists of the present invention may also be used in a method treating various forms of dermatitis. Dermatitis is a descriptive term referring to poorly demarcated lesions that are either pruritic, erythematous, scaly, blistered, weeping, fissured or crusted. These lesions arise from any of a wide variety of causes. The most common types of dermatitis are atopic, contact and diaper dermatitis. For example, seborrheic dermatitis is a chronic, usually pruritic, dermatitis with erythema, dry, moist, or greasy scaling, and yellow-crusted patches on various areas, especially the scalp, with exfoliation of an excessive amount of dry scales. The BOC/CDO hedgehog antagonists of the subject method may also be used in the treatment of stasis dermatitis, an often chronic, usually eczematous dermatitis. Actinic dermatitis is a dermatitis that due to exposure to actinic radiation such as that from the sun, ultraviolet waves, or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipruritics, and antibiotics. Additional skin ailments that may be treated with the BOC/CDO hedgehog antagonists of the present invention include disorders specific to non-humans, such as mange.

In yet another embodiment, the BOC/CDO hedgehog antagonists of the subject method can be used in regulating the activity in a noncanonical Shh pathway that is independent of the Patched-Smoothened receptor complex and the Gli transcription factors. In a recent report, Jarov et al, *Dev. Biol.* 261(2): 520-536 (2003), describes that, when Shh was immobilized to the subsrate (extracellular matrix) or produced by neuroepithelial cells themselves after transfection, neural plate explants failed to disperse and instead formed compact structures. Changes in the adhesive capacities of neuroepithelial cells caused by Shh could be accounted for by inactivation of surface 1-integrins combined with an increase in N-cadherin-mediated cell adhesion. This immobilized-Shh-mediated adhesion does not contradict or interfere with the previously known (soluble) Shh-mediated inductive, mitogenic, and trophic functions, since the immobilized Shh promoted differentiation of neuroepithelial cells into motor neurons and floor plate cells with the same potency as soluble Shh. It has also been demonstrated that Shh-regulation of adhesion properties during neural tube morphogenesis is rapid and reversible, and it does not involve the classical Patched-Smoothened-Gli signaling pathway, and it is independent and discernible from Shh-mediated cell differentiation. Thus, modifications of the adhesive properties of neural epithelial cells induced by Shh cannot be attribute to its differentiation-promoting effect, but reveal a novel function of Shh in this tissue that has not been described previously. Thus, the BOC/CDO hedgehog antagonists of the present invention may be used to regulate this non-canonical hedgehog pathway that is independent of Ptch, Smo, Fu, Su(Fu), Cos-2 and/or Gli. More specifically, such BOC/CDO hedgehog antagonists may be used in a method to disrupt this function in neuronal or other applicable tissues, preferably at specific developmental stages.

IV. Compositions and Methods of the Invention

A. Anti-BOC and Anti-CDO Antibodies

In one embodiment, the present invention provides the use of anti-BOC and/or anti-CDO antibodies, which may find use herein as therapeutic, diagnostic and/or prognostic agents in determining the severity of and/or prognosing the disease course of a BOC-deficient and/or CDO-hyperactive tumor or cancer. Exemplary antibodies that may be used for such purposes include polyclonal, monoclonal, humanized, bispecific, and heteroconjugate antibodies. The term "antibodies" sometimes also include antigen-binding fragments.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-BOC antibodies useful in the practice of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-BOC and/or anti-CDO antibody(ies) are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm);U.S. Pat. No. 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, while retaining similar antigen binding specificity of the corresponding full length molecule, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and scFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind separate antigens or bind to two different epitopes of a particular BOC or CDO polypeptide described herein. Other such antibodies may combine the above BOC- or CDO-binding site with a binding site for another protein (e.g., hedgehog). Alternatively, an anti-BOC and/or anti-CDO arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD 16), so as to focus and localize cellular defense mechanisms to the BOC- or CDO-expressing cell. Bispecific antibodies may also be used to localize cytotoxic agents to cells which express BOC or CDO. These antibodies possess a BOC-or CDO-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al, *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al, *J. Immunol.* 147:60 (1991). Such multiple valencies expressly includes anti-BOC and anti-CDO in combination with binding regions to other antigens of interest.

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Patent 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

9. Immunoconjugates

The invention also pertains to immunoconjugates comprising a BOC hedgehog antagonist and/or CDO antagonist polypeptide conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

a. Chemotherapeutic Agents

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al, *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

b. Maytansine and Maytansinoids

In one preferred embodiment, a BOC hedgehog antagonist and/or CDO antagonist polypeptide of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA. 1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

BOC/CDO hedgehog antagonist-maytansinoid conjugates may be prepared by chemically linking an BOC/CDO hedgehog antoagnist to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody- or antibody fragment-maytansinoid conjugates, including, for example, those disclosed in U.S. Pat. No. 5,208,020 or EP Patent 0 425 235 B1, and Chari et al., *Cancer Research* 52:127-131 (1992). The linking groups include disufide groups, thioether groups, acid labile groups, photolabile groups, peptidase labile groups, or esterase labile groups, as disclosed in the above-identified patents, disulfide and thioether groups being preferred.

Conjugates of the antibody or antibody fragment and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

c. Calicheamicin

Another immunoconjugate of interest comprises a BOC/CDO hedgehog antagonist conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

d. Other Cytotoxic Agents

Other antitumor agents that can be conjugated to the BOC/CDO hedgehog antagonists of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated BOC/CDO hedgehog antagonists. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein or chimeric molecule comprising the BOC hedgehog antagonist and/or CDO antagonist polypeptide\may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the BOC/CDO hedgehog antagonist may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The BOC/CDO hedgehog antagonists described herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. BOC Binding Oligopeptides and CDO Binding Oligopeptides

BOC binding oligopeptides and/or CDO binding oligopeptides of the present invention are oligopeptides that bind, preferably specifically, to a BOC polypeptide or a CDO polypeptide, respectively, as described herein. Such oligopeptides may be chemically synthesized using known oligopeptide synthesis methodology or may be prepared and purified using recombinant technology. BOC binding oligopeptides and/or CDO binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, and such oligopeptides are capable of binding, preferably specifically, to a BOC polypeptide or CDO polypeptide, respectively, as described herein. BOC binding oligopeptides and/or CDO binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833, 092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc. Natl. Acad. Sci. USA,* 88:8363, and Smith, G. P. (1991) *Current Opin. Biotechnol.,* 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science* 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA,* 87:6378) or protein (Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc.*

*Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215: 439 (1998); Zhu et al., *Cancer Research*, 58(15): 3209-3214 (1998); Jiang et al., *Infection & Immunity*, 65(11): 4770-4777 (1997); Ren et al., Gene, 195(2):303-311 (1997); Ren, *Protein Sci.*, 5: 1833 (1996); Efimov et al., *Virus Genes*, 10: 173 (1995)) and T7 phage display systems (Smith and Scott, *Methods in Enzymology*, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (L1 et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Screening for BOC/CDO Hedgehog Antagonists

Techniques for generating the BOC/CDO hedgehog antagonists (polypeptides, antibodies, polypeptides, oligopeptides and organic molecules) for use with the inventive method have been described above. One may further select antibodies (and antigen-binding fragments thereof), oligopeptides or other organic molecules with certain biological characteristics, as desired.

The growth inhibitory effects of the various BOC/CDO hedgehog antagonists useable in the invention may be assessed by methods known in the art, e.g., using cells which express a BOC or CDO polypeptide either endogenously or following transfection with the respective BOC or CDO gene. For example, appropriate tumor cell lines and cells transfected with BOC-encoding or CDO-encoding nucleic may be treated with the BOC/CDO hedgehog antagonists of the invention at various concentrations for a few days (e.g., 2-7) days and stained with crystal violet or MTT or analyzed by some other calorimetric assay. Another method of measuring proliferation would be by comparing $^3$H-thymidine uptake by the cells treated in the presence or absence of such BOC/CDO hedgehog antagonists. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses a hedgehog polypeptide. Preferably, such BOC/CDO hedgehog antagonists will inhibit cell proliferation of a hedgehog-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at a BOC/CDO hedgehog antagonist concentration of about 0.5 to 30 µg/ml or about 0.5 nM to 200 nM in cell culture, where the growth inhibition is determined 1-10 days after exposure of the tumor cells to the antagonist. The antagonist is growth inhibitory in vivo if administration of antagonist and/or agonist at about 1 µg/kg to about 100 mg/kg body weight results in reduction in tumor size or reduction of tumor cell proliferation within about 5 days to 3 months from the first administration of the antibody, preferably within about 5 to 30 days.

To select for BOC/CDO hedgehog antagonists which induce cell death, loss of membrane integrity as indicated by, e.g., propidium iodide (PI), trypan blue or 7AAD uptake may be assessed relative to control. A PI uptake assay can be performed in the absence of complement and immune effector cells. BOC polypeptide- and/or CDO-expressing expressing tumor cells are incubated with medium alone or medium containing the appropriate BOC/CDO hedgehog antagonist. The cells are incubated for a 3 day time period. Following each treatment, cells are washed and aliquoted a into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those BOC/CDO hedgehog antagonists that induce statistically significant levels of cell death as determined by PI uptake may then be selected.

To screen for BOC hedgehog antagonists and/or CDO antagonist polypeptides which bind to an epitope on a BOC polypeptide, or CDO polypeptide, respectively, a routine cross-blocking assay such as that described in *Antibodies: A Laboratory Manual*, Cold Spring Harbor Laboratory, Ed Harlow and David Lane (1988), can be performed. This assay can be used to determine if a test antibody, polypeptide, oligopeptide or other organic molecule binds the same site or epitope as a known BOC/CDO hedgehog antagonist. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a BOC polypeptide or CDO polypeptide can be used in competition assays with the test antibodies or with a test antibody and an antibody with a characterized or known epitope.

D. Antibody Dependent Enzyme Mediated Prodrug Therapy (ADEPT)

The BOC/CDO hedgehog antagonists of the present invention that are antibodies may also be used in ADEPT by conjugating such an antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the BOC/CDO hedgehog antagonist antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984)).

E. BOC Polypeptide and/or CDO Polypeptide Variants

In addition to the BOC polypeptides and/or CDO polypeptides described herein, it is contemplated that variants of such molecules can be prepared for use with the invention herein. Such variants can be prepared by introducing appropriate nucleotide changes into the encoding DNA, and/or by synthesis of the desired antibody or polypeptide. Those skilled in the art will appreciate that amino acid changes may alter post-translational processes of these molecules, such as changing the number or position of glycosylation sites or altering the membrane anchoring characteristics.

Variations in amino acid sequence can be made, for example, using any of the techniques and guidelines for conservative and non-conservative mutations set forth, for instance, in U.S. Pat. No. 5,364,934. Variations may be a substitution, deletion or insertion of one or more codons encoding the amino acid sequence that results in a change in the amino acid sequence as compared with the native sequence. Optionally the variation is by substitution of at least one amino acid with any other amino acid in one or more of the domains of the amino acid sequence of interest. Guidance in determining which amino acid residue may be inserted, substituted or deleted without adversely affecting the desired activity may be found by comparing the sequence of the amino acid sequence of interest with homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Fragments of the various BOC and/or CDO polypeptides are provided herein. Such fragments may be truncated at the N-terminus or C-terminus, or may lack internal residues, for example, when compared with a full length native antibody or protein. Such fragments which lack amino acid residues that are not essential for a desired biological activity are also useful with the disclosed methods.

The above polypeptide fragments may be prepared by any of a number of conventional techniques. Desired peptide fragments may be chemically synthesized. An alternative approach involves generating such fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding the desired fragment by polymerase chain reaction (PCR). Oligonucleotides that define the desired termini of the DNA fragment are employed at the 5' and 3' primers in the PCR. Preferably, such fragments share at least one biological and/or immunological activity with the corresponding full length molecule.

In particular embodiments, conservative substitutions of interest are shown in Table 5 under the heading of preferred substitutions. If such substitutions result in a change in biological activity, then more substantial changes, denominated exemplary substitutions in Table 5, or as further described below in reference to amino acid classes, are introduced and the products screened in order to identify the desired variant.

TABLE 5

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser, Ala | Ser |
| Gln (Q) | Asn; Glu | Asn |
| Glu (E) | Asp, Gln | Asp |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Leu |
| Pro (P) | Ala | Ala |
| Ser (S) | Thr | Thr |
| Thr (T) | Val; Ser | Ser |

TABLE 5-continued

| Original Residue | Exemplary Substitutions | Preferred Substitutions |
|---|---|---|
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the BOC polypeptides are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the anti-BOC molecule.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, *J. Mol. Biol.,* 150:1 (1976)]. If alanine substitution does not yield adequate amounts of variant, an isoteric amino acid can be used.

Any cysteine residue not involved in maintaining the proper conformation of the BOC and/or CDO polypeptides also may be substituted, generally with serine, to improve the oxidative stability of the molecule and prevent aberrant crosslinking. Conversely, cysteine bond(s) may be added to such a molecule to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of BOC and/or CDO polypeptides are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of a native sequence or an earlier prepared variant.

F. Modifications of BOC and/or CDO Polypeptides

In one embodiment, such a chimeric molecule comprises a fusion of the BOC and/or CDO polypeptides (E.g., BOC chimeric polypeptides, CDO chimeric polypeptides, respectively) with a tag polypeptide which provides an epitope to which an anti-tag antibody can selectively bind. The epitope tag is generally placed at the amino- or carboxyl-terminus of such antibody or polypeptide. The presence of such epitope-tagged forms of such antibodies or polypeptides can be detected using an antibody against the tag polypeptide. Also, provision of the epitope tag enables such antibodies or polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

In an alternative embodiment, the chimeric molecule may comprise a fusion of the BOC and/or CDO polypeptides with an immunoglobulin or a particular region of an immunoglobulin (E.g., Fc domain). For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a preceding antibody or polypeptide in the place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

G. Preparation of BOC and/or CDO polypeptides

The description below relates primarily to production of BOC and/or CDO polypeptides by culturing cells transformed or transfected with a vector containing nucleic acid such antibodies, polypeptides and oligopeptides. For purposes of this section G. and the Examples only, the term "BOC polypeptides" and "CDO polypeptides" shall include the respective BOC-binding and CDO-binding antibodies, (including BOC- and CDO-binding antibody fragments) polypeptides (including chimeric polypeptides) and oligopeptides". It is, of course, contemplated that alternative methods, which are well known in the art, may be employed to prepare such antibodies, polypeptides and oligopeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using the manufacturer's instructions. Various portions of such antibodies, polypeptides or oligopeptides may be chemically synthesized separately and combined using chemical or enzymatic methods to produce the desired product.

1. Isolation of DNA Encoding BOC and/or CDO Polypeptides

DNA encoding a BOC polypeptide and/or CDO polypeptide may be obtained from a cDNA library prepared from tissue believed to possess such antibody, polypeptide or oligopeptide mRNA and to express it at a detectable level. Accordingly, DNA encoding such polypeptides can be conveniently obtained from a cDNA library prepared from human tissue, a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). Alternatively, PCR methodology may be used. [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for BOC and/or CDO polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Patent No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g. *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degp ompT kan$^r$; *E. coli* W3110 strain 37D6, which has the complete genotype tonA ptr3 phoA E15 (argF-lac)169 degp ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Patent No. 4,946,783 issued 7 Aug. 1990. Alternatively, in vitro methods of cloning, e.g. PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed in suitable cells (e.g., CHO cells).

In addition to prokaryotes, eukaryotic microbes such as filamentous fungi or yeast are suitable cloning or expression hosts for vectors encoding BOC and/or CDO polypeptides. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183, 070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated BOC and/or CDO polypeptide production are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR(CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for BOC and/or CDO polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding the respective BOC and/or CDO polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The BOC and/or CDO polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the DNA encoding the mature sequence that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010, 182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up nucleic acid encoding the desire protein, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the nucleic acid sequence encoding the desired amino acid sequence, in order to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding the desired protein sequence.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

DNA Transcription in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the BOC polypeptide and/or CDO polypeptide may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence of the preceding amino acid sequences, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the respective antibody, polypeptide or oligopeptide described in this section.

Still other methods, vectors, and host cells suitable for adaptation to the synthesis of the respective antibody, polypeptide or oligopeptide in recombinant vertebrate cell culture are described in Gething et al., *Nature*, 293:620-625 (1981); Mantei et al., *Nature*, 281:40-46 (1979); EP 117,060; and EP 117,058.

4. Culturing the Host Cells

The host cells used to produce the BOC and/or CDO polypeptides may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or U.S. Pat. No. 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies suitable for the present method may be prepared against a native sequence polypeptide or oligopeptide, or against exogenous sequence fused to DNA and encoding a specific antibody epitope of such a polypeptide or oligopeptide.

6. Protein Purification

BOC and/or CDO polypeptides may be recovered from culture medium or from host cell lysates. If membrane-bound, it can be released from the membrane using a suitable detergent solution (e.g. Triton-X 100) or by enzymatic cleavage. Cells employed in expression of the preceding can be disrupted by various physical or chemical means, such as freeze-thaw cycling, sonication, mechanical disruption, or cell lysing agents.

It may be desireable to purify the preceding from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the desired molecules. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular antibody, polypeptide or oligopeptide produced for the claimed methods.

When using recombinant techniques, the BOC and/or CDO polypeptide can be produced intracellularly, in the periplasmic space, or directly secreted into the medium. If such molecules are produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Purification can occur using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

H. Pharmaceutical Formulations

Therapeutic formulations of the BOC/CDO hedgehog antagonists ("therapeutic agent") used in accordance with the present invention may be prepared for storage by mixing the therapeutic agent(s) having the desired degree of purity with optional pharmaceutically acceptable carriers, excipients or stabilizers (*Remington: The Science of Practice of Pharmacy*, 20th edition, Gennaro, A. et al., Ed., Philadelphia College of Pharmacy and Science (2000)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations of therapeutic agents described herein may also contain more than one active compound as necessary for the particular indication being treated, preferably those with complementary activities that do not adversely affect each other. For example, in addition to the preceding therapeutic agent(s), it may be desirable to include in the formulation, an additional antibody, e.g., a second such therapeutic agent, or an antibody to some other target such as a growth factor that affects the growth of the glioma. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy*, supra.

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

I. Diagnosis and Treatment with BOC/CDO Hedgehog Antagonists

To determine BOC and/or CDO expression in tumor or cancer, various diagnostic assays are available. In one embodiment, hedgehog and/or CDO polypeptide overexpression, and/or BOC polypeptide underexpression, may be analyzed by immunohistochemistry (IHC). Parrafin embedded tissue sections from a tumor biopsy may be subjected to the IHC assay and accorded a hedgehog, BOC and/or CDO protein staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+scores for hedgehog, BOC or CDO polypeptide expression may be characterized as underexpressing, or not overexpressing hedgehog, BOC or CDO, respectively, whereas those tumors with 2+ or 3+ scores may be characterized as overexpressing hedgehog, BOC, or CDO, respectively.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of hedgehog or CDO overexpression, and/or BOC underexpression in the tumor.

Hedgehog, BOC or CDO overexpression or amplification may be evaluated using an in vivo diagnostic assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

Currently, depending on the stage of the cancer, cancer treatment involves one or a combination of the following therapies: surgery to remove the cancerous tissue, radiation therapy, and chemotherapy. Therapy comprising of administering BOC/CDO hedgehog antagonists may be especially desirable in elderly patients who do not tolerate the toxicity and side effects of chemotherapy well and in metastatic disease where radiation therapy has limited usefulness. The tumor targeting BOC/CDO hedgehog antagonists of the present inventive method may also be used to alleviate hedgehog and/or CDO overexpressing and/or BOC-underexpressing cancers upon initial diagnosis of the disease or during relapse. For therapeutic applications, such BOC/CDO hedgehog antagonists can be used in combination with, before or after application of other conventional agents and/or methods for the treatment of glioma, e.g., hormones, antiangiogens, or radiolabelled compounds, or with surgery, cryotherapy, radiotherapy and/or chemotherapy. Chemotherapeutic drugs such as TAXOTERE® (docetaxel), TAXOL® (palictaxel), estramustine and mitoxantrone are used in treating cancer, in particular, in good risk patients.

In particular, combination therapy with palictaxel and modified derivatives (see, e.g., EP0600517) is contemplated. The preceding BOC/CDO hedgehog antagonist will be administered with a therapeutically effective dose of the chemotherapeutic agent. In another embodiment, such antibody, polypeptide, oligopeptide or organic molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, an immunoconjugate comprising such a BOC/CDO hedgehog antagonist conjugated with a cytotoxic agent is administered to the patient. Preferably, such immunoconjugate is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The preceding BOC/CDO hedgehog antagonists or toxin conjugates thereof are administered to a human patient, in accord with known methods, such as intravenous administration, e.g., as a bolus or by continuous infusion over a period of time, by intracranial, intracerobrospinal, intra-articular, intrathecal, intravenous, intraarterial, subcutaneous, oral, topical, or inhalation routes.

Other therapeutic regimens may be combined with the administration of the foregoing BOC/CDO hedgehog antagonists. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In another embodiment, the therapeutic treatment methods of the present invention involves the combined administration of the preceding BOC/CDO hedgehog antagonist and one or more chemotherapeutic agents or growth inhibitory agents, including co-administration of cocktails of different chemotherapeutic agents. Example chemotherapeutic agents have been provided previously. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

For the prevention or treatment of disease, the dosage and mode of administration will be chosen by the physician according to known criteria. The appropriate dosage of BOC/CDO hedgehog antagonists will depend on the type of disease to be treated, the severity and course of the disease, whether administration is for preventive or therapeutic purposes, previous therapy (including) the patient's clinical history and response, and the discretion of the attending physician. The preceding BOC/CDO hedgehog antagonists may be suitably administered to the patient at one time or over a series of treatments. Administration may occur by intravenous infusion or by subcutaneous injections. Depending on the type and severity of the disease, about 1 µg/kg to about 50 mg/kg body weight (e.g., about 0.1-15 mg/kg/dose) of BOC/CDO hedgehog antagonist can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of such a BOC/CDO hedgehog antagonist. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the BOC/CDO hedgehog polypeptide antagonists is encompassed by the expression "administering a therapeutically effective amount of an antibody". See, for example, WO96/07321 published Mar. 14, 1996 concerning the use of gene therapy to generate intracellular antibodies.

There are two major approaches to getting such nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

J. Articles of Manufacture and Kits

For therapeutic applications, the article of manufacture comprises a container and a label or package insert on or associated with the container indicating a use for the inhibition in whole or in part of hedgehog signaling, or alternatively for the treatment of a disorder or condition resulting from activation of the hedgehog signaling pathway. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is a BOC/CDO hedgehog antagonist. The label or package insert indicates that the composition is used for treating glioma. The label or package insert will further comprise instructions for administering the BOC/CDO hedgehog antagonist. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits may also be provided that are useful for various other purposes, e.g., for BOC-expressing and/or CDO-expressing cell killing assays, for purification or immunoprecipitation of BOC and/or CDO polypeptide from cells. For isolation and purification of BOC and/or CDO polypeptide, the kit can contain the respective BOC- and/or CDO-binding reagent coupled to beads (e.g., sepharose beads). Kits can be provided which contain such molecules for detection and quantitation of BOC and/or CDO polypeptide in vitro, e.g., in an ELISA or a Western blot. As with the article of manufacture, the kit comprises a container and a label or package insert on or associated with the container. The container holds a composition comprising at least one such BOC and/or CDO binding reagent useable with the invention. Additional containers may be included that contain, e.g., diluents and buffers, control antibodies. The label or package insert may provide a description of the composition as well as instructions for the intended in vitro or diagnostic use.

K. Sense and Anti-Sense BOC- and/or CDO-Encoding Nucleic Acids

Molecules that would be expected: (1) to inhibit BOC, and therefor activate or amplify hedgehog signaling; as well as (2) to inhibit CDO, and therefor inhibit or antagonize hedgehog signaling, include fragments of the respective BOC- or CDO-encoding nucleic acids such as antisense or sense oligonucleotides ("BOC sense/antisense NA" and "CDO sense/antisense NA", respectively). Such nucleic acids comprise a single-stranded nucleic acid sequence (either RNA or DNA) capable of binding to the respective target (a) BOC or CDO mRNA (sense) or (b) BOC or CDO DNA (antisense) sequences. BOC sense/antisense NA and CDO sense/antisense NA comprise a fragment of the coding region of the respective BOC or CDO RNA or DNA. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The BOC sense/antisense NA and/or CDO sense/antisense NA thus may be used to block the respective expression of: (1) BOC polypeptides, wherein those BOC polypeptides may play a role in the inhibition or attenuation of hedgehog signaling; and/or (2) CDO polypeptides, wherein those CDO polypeptides may play a role in the activation or amplification of hedgehog signaling. Such BOC sense/antisense NA and/or CDO sense/antisense NA may further comprise oligonucleotides having modified sugar-phosphodiester backbones (or other sugar linkages, such as those described in WO 91/06629) and wherein such sugar linkages are resistant to endogenous nucleases. Nucleic acid with such resistant sugar linkages are stable in vivo (i.e., capable of resisting enzymatic degradation) but retain sequence specificity to be able to bind to target nucleotide sequences.

The BOC sense/antisense NA and/or CDO sense/antisense NA used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of BOC sense/antisense NA and/or CDO sense/antisense NA suitable for use in the present invention include those oligonucleotides which are covalently linked to organic moieties, such as those described in WO 90/10048, and other moieties that increases the affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides suitable for use in the present invention may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Alternatively, such sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in L. Screening Assays Used to Identify BOC/CDO Hedgehog Antagonists:

The assays can be performed in a variety of formats, including protein-protein binding assays, biochemical screening assays, immunoassays, and cell-based assays, which are well characterized in the art.

All antagonist style assays share the common feature of contacting the drug candidate (target molecule) against a BOC polypeptide (to screen for hedgehog agonists) or with a hedgehog or CDO polypeptide (to screen for hedgehog antagonists), under conditions and for a time sufficient to allow these two components to interact.

In binding assays, the interaction is binding and the complex formed can be isolated or detected in the reaction mixture. In a particular embodiment, the target molecule encoded by the gene identified herein or the drug candidate is immobilized on a solid phase, e.g., on a microtiter plate, by covalent or non-covalent attachments. Non-covalent attachment generally is accomplished by coating the solid surface with a solution of the target molecule and drying. Alternatively, an immobilized antibody, e.g., a monoclonal antibody, specific for the target molecule to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular target molecule encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a target molecule identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for suitable drug candidates, the target molecule may be added to a cell along with the compound to be screened for a particular activity (e.g., hedgehog signaling activation or inhibition) and the ability of the compound to inhibit the activity of interest in the presence of the target molecule indicates that the test compound is an antagonist to the target molecule. Alternatively, antagonists may be detected by combining the target molecule and a potential antagonist with membrane-bound target molecule or recombinant receptors under appropriate conditions for a competitive inhibition assay. The target molecule can be labeled, such as by radioactivity, such that the number of target molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the target molecule and a cDNA library created from this RNA is divided into pools and used to transfect COS cells or other cells that are not responsive to the target molecule. Transfected cells that are grown on glass slides are exposed to labeled target molecule. The target molecule can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled target molecule can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled target molecule in the presence of the candidate compound. The ability of the compound to enhance or block this interaction could then be measured.

More specific examples of potential antagonists include an oligonucleotide that binds to the fusions of immunoglobulin with target molecule, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the target molecule that recognizes the receptor but imparts no effect, thereby competitively inhibiting the action of the target molecule.

Another potential BOC antagonist (i.e., hedgehog agonist) or CDO antagonist (i.e., hedgehog antagonist) is an antisense RNA or DNA construct prepared using antisense technology, where, e.g., an antisense RNA or DNA molecule acts to block directly the translation of mRNA by hybridizing to targeted mRNA and preventing protein translation.

Additional potential BOC antagonists (i.e., hedgehog agonists) and CDO antagonists (i.e., hedgehog antagonists) include small molecules that bind to the active site, the receptor binding site, or growth factor or other relevant binding site of the respective BOC or CDO polypeptide, thereby blocking its normal biological activity. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

The following examples are offered for illustrative purposes only, and are not intended to limit the scope of the present invention in any way.

All patent and literature references cited in the present specification are hereby incorporated by reference in their entirety.

M. RNAi Preparation

An "RNA coding region" is a nucleic acid that can serve as a template for the synthesis of an RNA molecule, such as a double-stranded RNA complex. Preferably, the RNA coding region is a DNA sequence.

The RNA coding region preferably encodes a double-stranded RNA complex (e.g., siRNA, miRNA, shRNA) that is capable of down-regulating the expression of a particular gene or genes. In some embodiments, a double-stranded RNA complex is expressed in the form of an RNA molecule having a stem-loop or a so-called "hairpin" structure. As used herein, "hairpin" structure encompasses shRNAs and miRNAs. In some embodiments, a double-stranded RNA complex is expressed in the form of separate complementary or partially complementary RNA strands.

Methods are well-known in the art for designing double-stranded RNA complexes, eg, siRNA, miRNA, and shRNAs. For example, resources and citations describing the design of effective shRNA and siRNA are found in Sandy et al, *BioTechniques* 39:215-224 (2005). It is understood that the sequences of a double-stranded RNA complex may be of natural origin or may be synthetic. For example, Example 13 discloses a hybrid miRNA comprising a synthetic double stranded portion embedded in the backbone of a naturally occurring microRNA.

The RNA complex comprises a double-stranded region corresponding to a region of a gene to be down-regulated is expressed in the cell. One strand of the RNA double-stranded region is substantially identical (typically at least about 80%, 85%, 90%, 91%, 92%, 93%, 94%, 95%, 96%, 97%, 98%, 99% identical) in sequence to the sequence of the coding region targeted for down regulation. The other strand of the double-stranded region (interchangeably termed "RNA double-stranded region) is complementary to the sequence of the coding region targeted for down regulation, or partially complementary to the coding region targeted for down regulation (typically at least about 80%, 85%, 90%, 91%, 92%, 93%, 94%, 95%, 96%, 97%, 98%, 99% identical to the complement of the coding region targeted). It is understood that the double-stranded region can be formed by two separate RNA stranded, or by the self-complementary portions of a single RNA having a hairpin structure. The double-stranded region is generally at least about 15 nucleotides in length and, in some embodiments, is about 15 to about 30 nucleotides in length. However, a significantly longer double-stranded region can be used effectively in some organisms. In a more preferred embodiment, the double-stranded region is between about 19 and 22 nucleotides in length. The double-stranded region is preferably identical to the target nucleotide sequence over this region.

When the coding region to be down regulated is in a family of highly conserved genes, the sequence of the RNA double-stranded region can be chosen with the aid of sequence comparison to target only the desired gene. On the other hand, if there is sufficient identity among a family of homologous genes within an organism, a double-stranded can be designed that would down regulate a plurality of genes simultaneously.

In some embodiments, a single RNA coding region in the construct serves as a template for the expression of a self-complementary hairpin RNA, comprising a sense region, a loop region and an antisense region. The sense and antisense regions are each preferably about 15 to about 30 nucleotides in length. The loop region preferably is about 2 to about 15 nucleotides in length, more preferably from about 4 to about 9 nucleotides in length. Following expression the sense and antisense regions form a duplex.

In another embodiment, the vector comprises two RNA coding regions. The first coding region is a template for the expression of a first RNA and the second coding region is a template for the expression of a second RNA. Following expression, the first and second RNAs form a duplex. The retroviral construct preferably also comprises a first Pol III promoter operably linked to the first RNA coding region and a second Pol III promoter operably linked to the second RNA coding region.

It is understood that, in certain embodiments, a vector of the invention can encompass nucleic acid sequences sufficient to form more than RNA coding region that inhibit expression of distinct target genes. In this embodiment, simultaneous inhibition of distinct target genes can be accomplished with a single vector of the invention. The number of different RNA complex transcripts that can be expressed simultaneously is limited only by the packaging capacity of the vector (if a viral vector is used) and adjacent promoters, including any of the promoters described below, can be selected to eliminate or minimize interference and allow for efficient simultaneous inhibition of multiple target genes. The inhibition of multiple RNA construct transcripts of adjacent promoters, for example, 2 or more, 3 or more, 4 or more, 5 or more, 6 or more, 7 or more, 8 or more, 9 or more, or 10 or more adjacent promoters allows the user to generate a desire phenotype that develops only when several coding regions (eg, genes) are targeted simultaneously and enables manipulation and elucidation of complex genetic systems.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding Human PRO1190

The extracellular domain (ECD) sequences (including the secretion signal sequence, if any) from about 950 known secreted proteins from the Swiss-Prot public database were used to search EST databases. The EST databases included public EST databases (e.g., GenBank). The search was performed using the computer program BLAST or BLAST2 [Altschul et al., *Methods in Enzymology*, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

This method allowed the identification of a single Merck/ Washington University EST sequence, EST no. AA339802, from which oligonucleotides were synthesized: 1) to identify by PCR a cDNA library that contained the sequence of interest, and 2) for use as probes to isolate a clone of the full-length coding sequence for PRO1190. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer: (53943.f1)
GGGAAACACAGCAGTCATTGCCTGC      (SEQ ID NO: 5)

reverse PCR primer: (53943.r1)
GCACACGTAGCCTGTCGCTGGAGC       (SEQ ID NO: 6)
```

Additionally, a synthetic oligonucleotide hybridization probe was constructed from the DNA53943 sequence which had the following nucleotide sequence:
hybridization probe: (53943.p1):

```
                                        (SEQ ID NO: 7)
CACCCCAAAGCCCAGGTCCGGTACAGCGTCAAACAAGAGTGG
```

In order to screen several libraries for a source of a full-length clone, DNA from the libraries was screened by PCR amplification with the PCR primer pair identified above. A positive library was then used to isolate clones encoding the PRO1190 gene using the probe oligonucleotide and one of the PCR primers.

RNA for construction of the cDNA libraries was isolated from human bone marrow. The cDNA libraries used to isolated the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for PRO1190 (designated herein as DNA59586 [FIG. 2, SEQ ID NO:3]; and the derived protein sequence for PRO190.

The entire coding sequence of PRO1190 is shown in FIG. 2A (SEQ ID NO:3). Clone DNA59586 contains a single open reading frame with an apparent translational initiation site at nucleotide positions 340-342, and an apparent stop codon at nucleotide positions 3685-3687. The predicted polypeptide precursor is 1115 amino acids long. The full-length PRO1190 protein shown in FIG. 2A has an estimated molecular weight of about 121,188 Daltons and a pI of about 7.07. Other features of the PRO1190 protein include: two transmembrane domains at amino acids 16-30 and 854-879; a cytochrome P450 cysteine heme-iron ligand signature at amino acids 1051-1060; an N-6 adenine-specific DNA methylases signature at amino acids 1045-1051; and potential N-glycosylation sites at amino acids 65-68, 76-79, 98-101, 189-192, 275-278, 518-521, 726-729, and 760-763. Clone DNA59586 (UNQ604), designated as DNA59586-1520 was deposited with the ATCC on Sep. 29, 1998, and is assigned ATCC deposit no. 203288.

Example 1A

Identification of Clones Encoding PRO38430

The clone DNA227967 (UNQ9067) may be isolated in a manner similar to that described above for DNA59586. Alternatively, similar CDO related sequences are publicly available under accession number NM_016952. The predicted polypeptide is 1240 amino acids in length. The full-length PRO38430 show in FIG. 2B has an estimated molecular weight of about 134,024 Daltons and a pI of about 6.38. Other features of the PRO38430 protein includes a transmembrane domain at about residues 941-961, Immunoglobulin domains at about residues 19-75, 212-268, 302-358, 395-478, Fibronectin type III domains at about residues 553-643, 697-783, 799-892, Immuno Tyrosine Inhibition Motif at about residues 972-992.

Example 2

Microarray Analysis to Detect Downregulation of BOC Polypeptides and/or Upregulation of CDO Polypeptides in Cancer or Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

Example 3

Quantitative Analysis of BOC and/or CDO mRNA Expression

In this assay, a 5' nuclease assay (for example, TaqMan®) and real-time quantitative PCR (for example, ABI Prizm 7700 Sequence Detection System® (Perkin Elmer, Applied Biosystems Division, Foster City, Calif.)), is used to find genes that are significantly overexpressed in a cancerous glioma tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative and quantitative interpretation of the data. This assay is well known and routinely used in the art to quantitatively identify gene expression differences between two different human tissue samples, see, e.g., Higuchi et al., *Biotechnology* 10:413-417 (1992); Livak et al., *PCR Methods Appl.*, 4:357-362 (1995); Heid et al., *Genome Res.* 6:986-994 (1996); Pennica et al., *Proc. Natl. Acad. Sci. USA* 95(25):14717-14722 (1998); Pitti et al., *Nature* 396 (6712):699-703 (1998) and Bieche et al., *Int. J. Cancer* 78:661-666 (1998).

The 5' nuclease procedure is run on a real-time quantitative PCR device such as the ABI Prism 7700TM Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen is mRNA isolated from a variety of different cancerous tissues. The mRNA is quantitated precisely, e.g., fluorometrically. As a negative control, RNA is isolated from various normal tissues of the same tissue type as the cancerous tissues being tested. Frequently, tumor sample(s) are directly compared to "matched" normal sample(s) of the same tissue type, meaning that the tumor and normal sample(s) are obtained from the same individual.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively and quantitatively measure the relative fold increase in mRNA expression between two or more different tissues. In this regard, it is well accepted in the art that this assay is sufficiently technically sensitive to reproducibly detect an at least 2-fold increase in mRNA expression in a human tumor sample relative to a normal control.

Example 4

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization is performed following an optimized version of the protocol by Lu and Gillett, *Cell Vision* 1:169-176 (1994), using PCR-generated $^{33}$P-labeled riboprobes.

Briefly, formalin-fixed, paraffin-embedded human tissues are sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe are generated from a PCR product and hybridized at 55° C. overnight. The slides are dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5×transcription buffer
1.0 µl DTT (100 mM)
2.0 µl NTP mix (2.5 mM:10µ; each of 10 mM GTP, CTP & ATP+10 µl H$_2$O)
1.0 µl UTP (50 µM)
1.0 µl Rnasin
1.0 µl DNA template (1 µg)
1.0 µt H$_2$O
1.0 µl RNA polymerase (for PCR products T3=AS, T7=S, usually)

The tubes are incubated at 37° C. for one hour. 1.0 µl RQ1 DNase is added, followed by incubation at 37° C. for 15 minutes. 90 µl TE (10 mM Tris pH 7.6/1 mM EDTA pH 8.0) are added, and the mixture was pipetted onto DE81 paper. The remaining solution is loaded in a Microcon-50 ultrafiltration unit, and spun using program 10 (6 minutes). The filtration unit is inverted over a second tube and spun using program 2 (3 minutes). After the final recovery spin, 100 µl TE is added. 1 µl of the final product is pipetted on DE81 paper and counted in 6 ml of Biofluor II.

The probe is run on a TBE/urea gel. 1-3 µl of the probe or 5 µl of RNA Mrk III is added to 3 µl of loading buffer. After heating on a 95° C. heat block for three minutes, the probe is immediately placed on ice. The wells of gel are flushed, the sample loaded, and run at 180-250 volts for 45 minutes. The gel is wrapped in saran wrap and exposed to XAR film with an intensifying screen in −70° C. freezer one hour to overnight.

$^{33}$P-Hybridization

A. Pretreatment of Frozen Sections

The slides are removed from the freezer, placed on aluminium trays and thawed at room temperature for 5 minutes. The trays are placed in 55° C. incubator for five minutes to reduce condensation. The slides are fixed for 10 minutes in 4% paraformaldehyde on ice in the fume hood, and washed in 0.5×SSC for 5 minutes, at room temperature (25 ml 20×SSC+ 975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections are washed in 0.5×SSC for 10 minutes at room temperature. The sections are dehydrated in 70%, 95%, 100% ethanol, 2 minutes each.

B. Pretreatment of paraffin-embedded sections

The slides are deparaffinized, placed in SQ H$_2$O, and rinsed twice in 2×SSC at room temperature, for 5 minutes each time. The sections are deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)—formalin tissues. Subsequent rinsing in 0.5×SSC and dehydration are performed as described above.

C. Prehybridization

The slides are laid out in a plastic box lined with Box buffer (4×SSC, 50% formamide)—saturated filter paper.

D. Hybridization 1.0×10$^6$ cpm probe and 1.0 µl tRNA (50 mg/ml stock) per slide are heated at 95° C. for 3 minutes. The slides are cooled on ice, and 48 µl hybridization buffer are added per slide. After vortexing, 50 µl $^{33}$P mix are added to 50 µl prehybridization on slide. The slides are incubated overnight at 55° C.

E. Washes

Washing is done 2×10 minutes with 2×SSC, EDTA at room temperature (400 ml 20×SSC+16 ml 0.25M EDTA, V$_f$=4L), followed by RNaseA treatment at 37° C. for 30 minutes (500 µl of 10 mg/ml in 250 ml Rnase buffer=20 µg/ml). The slides are washed 2×10 minutes with 2×SSC, EDTA at room temperature. The stringency wash conditions can be as follows: 2 hours at 55° C., 0.1×SSC, EDTA (20 ml 20×SSC+16 ml EDTA, V$_f$=4L).

F. Oligonucleotides

In situ analysis is performed on a variety of DNA sequences disclosed herein. The oligonucleotides employed for these analyses is obtained so as to be complementary to the nucleic acids (or the complements thereof) as shown in the accompanying figures.

Example 5

Preparation of Antibodies that Bind BOC and/or CDO Polypeptide

Techniques for producing monoclonal antibodies are known in the art and are described, for instance, in Goding, supra. Immunogens that may be employed include purified BOC and/or CDO polypeptides, fusion proteins containing BOC and/or CDO polypeptides, and cells expressing recombinant BOC and/or CDO polypeptides on the cell surface. Selection of the immunogen can be made by the skilled artisan without undue experimentation.

Mice, such as Balb/c, are immunized with the above immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-BOC antibodies.

After a suitable antibody titer has been detected, the animals "positive" for antibodies can be injected with a final intravenous injection of BOC and/or CDO polypeptide. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells are screened in an ELISA for reactivity against BOC and/or CDO. Determination of "positive" hybridoma cells secreting the desired monoclonal antibodies against BOC and/or CDO is within the skill in the art.

The positive hybridoma cells can be injected intraperitoneally into syngeneic Balb/c mice to produce ascites containing the anti-BOC and/or anti-CDO monoclonal antibodies.

Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 6

Preparation of Toxin-Conjugated Antibodies that Bind BOC and/or CDO

The use of antibody-drug conjugates (ADC), i.e. immunoconjugates, for the local delivery of cytotoxic or cytostatic agents, i.e. drugs to kill or inhibit tumor cells in the treatment of cancer (Payne (2003) Cancer Cell 3:207-212; Syrigos and Epenetos (1999) Anticancer Research 19:605-614; Niculescu-Duvaz and Springer (1997) Adv. Drug Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet (Mar. 15, 1986) pp. 603-05; Thorpe, (1985) "Antibody Carriers Of Cytotoxic Agents In Cancer Therapy: A Review," in Monoclonal Antibodies '84: Biological And Clinical Applications, Pinchera et al. (eds.), pp. 475-506). Maximal efficacy with minimal toxicity is sought thereby. Efforts to design and refine ADC have focused on the selectivity of monoclonal antibodies (mAbs) as well as drug-linking and drug-releasing properties. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al. (2000) J. of the Nat. Cancer Inst. 92(19):1573-1581; Mandler et al. (2000) Bioorganic & Med. Chem. Letters 10:1025-1028; Mandler et al. (2002) Bioconjugate Chem. 13:786-791), maytansinoids (EP 1391213; Liu et al., (1996) Proc. Natl. Acad. Sci. USA 93:8618-8623), and calicheamicin (Lode et al. (1998) Cancer Res. 58:2928; Hinman et al. (1993) Cancer Res. 53:3336-3342).

Techniques for producing antibody-drug conjugates by linking toxins to purified antibodies are well known and routinely employed in the art. For example, conjugation of a purified monoclonal antibody to the toxin DM1 may be accomplished as follows. Purified antibody is derivatized with N-succinimidyl-4-(2-pyridylthio)-pentanoate to introduce dithiopyridyl groups. Antibody (376.0 mg, 8 mg/mL) in 44.7 ml of 50 mM potassium phosphate buffer (pH 6.5) containing NaCl (50 mM) and EDTA (1 mM) is treated with SPP (5.3 molar equivalents in 2.3 ml ethanol). After incubation for 90 minutes under argon at ambient temperature, the reaction mixture is gel filtered through a Sephadex G25 column equilibrated with 35 mM sodium citrate, 154 mM NaCl and 2 mM EDTA. Antibody containing fractions are then pooled and assayed. Antibody-SPP-Py (337.0 mg with releasable 2-thiopyridine groups) is diluted with the above 35 mM sodium citrate buffer, pH 6.5, to a final concentration of 2.5 mg/ml. DM1 (1.7 equivalents, 16.1 mols) in 3.0 mM dimethylacetamide (DMA, 3% v/v in the final reaction mixture) is then added to the antibody solution. The reaction is allowed to proceed at ambient temperature under argon for 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate is 5.0 ml/min and 65 fractions (20.0 ml each) are collected. Fractions are pooled and assayed, wherein the number of DM1 drug molecules linked per antibody molecule (p') is determined by measuring the absorbance at 252 nm and 280 nm.

For illustrative purposes, conjugation of a purified monoclonal antibody to the toxin DM1 may also be accomplished as follows. Purified antibody is derivatized with (Succinimidyl 4-(N-maleimidomethyl) cyclohexane-1-carboxylate (SMCC, Pierce Biotechnology, Inc) to introduce the SMCC linker. The antibody is treated at 20 mg/ml in 50 mM potassium phosphate/50 mM sodium chloride/2 mM EDTA, pH 6.5 with 7.5 molar equivalents of SMCC (20 mM in DMSO, 6.7 mg/ml). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody containing fractions are pooled and assayed. Antibody-SMCC is then diluted with 50 mM potassium phosphate/50 mM sodium chloride/2 mM EDTA, pH 6.5, to a final concentration of 10 mg/ml, and reacted with a 10 mM solution of DM1 (1.7 equivalents assuming 5 SMCC/antibody, 7.37 mg/ml) in dimethylacetamide. The reaction is stirred at ambient temperature under argon 16.5 hours. The conjugation reaction mixture is then filtered through a Sephadex G25 gel filtration column (1.5×4.9 cm) with 1×PBS at pH 6.5. The DM1/antibody ratio (p) is then measured by the absorbance at 252 nm and at 280 nm.

Cytotoxic drugs have typically been conjugated to antibodies through the often numerous lysine residues of the antibody. Conjugation through thiol groups present, or engineered into, the antibody of interest has also been accomplished. For example, cysteine residues have been introduced into proteins by genetic engineering techniques to form covalent attachment sites for ligands (Better et al. (1994) J. Biol. Chem. 13:9644-9650; Bernhard et al. (1994) Bioconjugate Chem. 5:126-132; Greenwood et al. (1994) Therapeutic Immunology 1:247-255; Tu et al. (1999) Proc. Natl. Acad. Sci. USA 96:4862-4867; Kanno et al (2000) J. of Biotechnology, 76:207-214; Chmura et al. (2001) Proc. Nat. Acad. Sci. USA 98(15):8480-8484; U.S. Pat. No. 6,248,564). Once a free cysteine residue exists in the antibody of interest, toxins can be linked to that site. As an example, the drug linker reagents, maleimidocaproyl-monomethyl auristatin E (MMAE), i.e. MC-MMAE, maleimidocaproyl-monomethyl auristatin F (MMAF), i.e. MC-MMAF, MC-val-cit-PAB-MMAE or MC-val-cit-PAB-MMAF, dissolved in DMSO, is diluted in acetonitrile and water at known concentration, and added to chilled cysteine-derivatized antibody in phosphate buffered saline (PBS). After about one hour, an excess of maleimide is added to quench the reaction and cap any unreacted antibody thiol groups. The reaction mixture is concentrated by centrifugal ultrafiltration and the toxin conjugated antibody is purified and desalted by elution through G25 resin in PBS, filtered through 0.2 m filters under sterile conditions, and frozen for storage.

Moreover, a free cysteine on an antibody of choice may be modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing the antibody in phosphate buffered saline at a concentration of approximately 1.6 mg/ml (10 micromolar) and allowing it to react for 1 hour. Excess BM(PEO)4 is removed by gel filtration in 30 mM citrate, pH 6 with 150 mM NaCl buffer. An approximate 10 fold molar excess DM1 is dissolved in dimethyl acetamide (DMA) and added to the antibody-BMPEO intermediate. Dimethyl formamide (DMF) may also be employed to dissolve the drug moiety reagent. The reaction mixture is allowed to react overnight before gel filtration or dialysis into PBS to remove unreacted drug. Gel filtration on S200 columns in PBS is used to remove high molecular weight aggregates and furnish purified antibody-BMPEO-DM1 conjugate.

Example 7

In Vitro Cell Killing Assays

Mammalian cells expressing the BOC and/or CDO polypeptide of interest may be obtained using standard expression vector and cloning techniques. Alternatively, many tumor cell lines expressing BOC and/or CDO polypeptides of interest are publicly available, for example, through the ATCC and can be routinely identified using standard ELISA or FACS analysis. Anti-BOC and/or anti-CDO monoclonal antibodies (and toxin conjugated derivatives thereof) may then be employed in assays to determine the ability of the antibody to kill BOC polypeptide expressing cells in vitro.

With specific regard to the present invention, a PC3-derived cell line that stably expresses BOC and/or CDO polypeptide on its cells surface (herein called PC3-gD-MDP) may be engineered using standard techniques and expression of the BOC and/or CDO polypeptide by the PC3-gD-MDP cells can be confirmed using standard FACS cell sorting, ELISA and immunohistochemistry analyses. The ability of an MMAE-conjugated anti-BOC and/or anti-CDO monoclonal antibody to cause the death of the respective BOC- and/or CDO-expressing cells may be determined using an in vitro cell killing assay employing the following protocol (Promega Corp. Technical Bulletin TB288; Mendoza et al (2002) *Cancer Res.* 62:5485-5488):

1. An aliquot of 50 μl of cell culture containing about $10^4$ cells (either PC3-gD-MDP cells or untransfected PC3 cells which do not express BOC) in growth medium is deposited in each well of a 96-well, opaque-walled plate. Additional control wells are set up which contain 50 μl of growth medium without cells.
2. The BOC- and/or CDO-MMAE conjugated antibody, or an MMAE-conjugated control monoclonal antibody that does not bind to BOC and/or CDO, respectively, is added to each well in a volume of 50 μl and at various concentrations ranging from 0.0001 to 100 μg/ml and the plates are incubated at 37° C. and 5% $CO_2$ for 3-5 days.
3. The plates are equilibrated to room temperature for approximately 30 minutes.
4. A volume of the CellTiter-Glo Luminescent Cell Viability Reagent from Promega Corp. equal to the volume of cell culture medium present in each well is added and the plates are shaken for 2 minutes on an orbital shaker to induce cell lysis.
5. The plates are incubated at room temperature for 10 minutes to stabilize the luminescence signal.
6. Luminescence is recorded on a luminometer with the Tropix Winglow Program and reported as RLU=relative luminescence units.

The results obtained from the above described assay can demonstrate that the BOC-MMAE and/or CDO-MMAE antibody is capable of inducing the death of cells that express the corresponding BOC and/or CDO polypeptide in an antibody-dependent fashion. That is, neither BOC-MMAE and/or CDO-MMAE nor MMAE-conjugated control can induce significant death of untransfected PC3 cells at an antibody concentration of 1 μg/ml and below. At antibody concentrations above 1 μg/ml, the amount of untransfected PC3 cell death may increase linearly with antibody concentration in an antibody-independent manner. Therefore, it will appear that the death of untransfected PC3 cells at antibody concentrations above 1 μg/ml is a non-specific result of the increasing levels of the MMAE toxin present in the reaction mixture and is not a function of the binding specificity of the antibody employed.

With regard to the PC3-gD-MDP cells that stably express the BOC and/or CDO polypeptide, however, while the MMAE-conjugated control induces cell death with a pattern that is identical to that antibody's ability to kill untransfected PC3 cells, the BOC-MMAE and/or CDO-MMAE will induce significant cell killing at antibody concentrations significantly below this level (e.g., as low as 0.001 μg/ml). In fact, at an antibody concentration of 1 μg/ml (where the non-BOC specific and/or non-CDO specific MMAE-conjugated control antibody exhibits no significant cell killing), virtually all of the BOC and/or CDO expressing PC3-gD-MDP cells will be killed by the respective BOC-MMAE and/or CDO-MMAE. As such, such data will demonstrate that BOC-specific and/or CDO-specific monoclonal antibody binds to the BOC and/or CDO polypeptide as it is expressed on the surface of cells and is capable of inducing the death of those cells to which it binds.

Example 8

In Vivo Tumor Cell Killing Assay

To test the efficacy of toxin-conjugated or unconjugated anti-BOC and/or anti-CDO monoclonal antibodies for the ability to induce the death of tumor cells in vivo, the following protocol may be employed.

Inoculate a group of athymic nude mice with $5 \times 10^6$ of the BOC polypeptide-expressing tumor promoting cells subcutaneously in the flank. When the tumors reach a mean tumor volume of between 100-200 mm$^3$, the mice are grouped equally into 5 groups and are treated as follows:

Group 1—PBS control vehicle administered once per week for 4 weeks;
Group 2—non-specific control antibody administered at 1 mg/kg, once per week for 4 weeks;
Group 3—non-specific control antibody administered at 3 mg/kg, once per week for 4 weeks;
Group 4—specific anti-BOC polypeptide antibody administered at 1 mg/kg, once per week for 4 weeks;
Group 5—specific anti-BOC polypeptide antibody administered at 3 mg/kg, once per week for 4 weeks.

Mean tumor volume may then be determined in the mice of each treatment group at periodic intervals and the efficacy of the antibodies determined.

Example 9

Use of BOC and/or CDO as a Hybridization Probe

The following method describes use of a nucleotide sequence encoding BOC polypeptide and/or CDO polypeptide as a hybridization probe for, i.e., diagnosis of the presence of a tumor in a mammal.

DNA comprising the coding sequence of full-length or mature BOC and/or CDO polypeptide as disclosed herein can also be employed as a probe to screen for homologous DNAs (such as those encoding naturally-occurring variants of BOC or CDO) in human tissue cDNA libraries or human tissue genomic libraries.

Hybridization and washing of filters containing either library DNAs is performed under the following high stringency conditions. Hybridization of radiolabeled BOC-and/or CDO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence BOC and/or CDO polypeptide can then be identified using standard techniques known in the art.

Example 10

Expression of BOC and/or CDO in *E. coli*

This example illustrates preparation of an unglycosylated form of BOC and/or CDO by recombinant expression in *E. coli*.

The DNA sequence encoding the preceding BOC and/or CDO polypeptide sequences is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the BOC and/or CDO coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized BOC and/or CDO polypeptide can then be purified using a metal chelating column under conditions that allow tight binding of the protein.

The preceding BOC and/or CDO polypeptide sequences may be expressed in *E. coli* in a poly-His tagged form, using the following procedure. The DNA encoding BOC and/or CDO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon gale rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate•2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded protein are pooled and the acetonitrile removed using a gentle stream of nitrogen directed at the solution. Proteins are formulated into 20 mM Hepes, pH 6.8 with 0.14 M sodium chloride and 4% mannitol

Example 11

Expression of BOC and/or CDO Polypeptide in Mammalian Cells

This example illustrates preparation of a potentially glycosylated form of BOC and/or CDO polypeptide by recombinant expression in mammalian cells.

The vector, pRK5 (see EP 307,247, published Mar. 15, 1989), is employed as the expression vector. Optionally, DNA encoding the BOC or CDO polypeptides described herein is ligated into pRK5 with selected restriction enzymes to allow insertion of such DNA using ligation methods such as described in Sambrook et al., supra. The resulting vector is called BOC-DNA or CDO-DNA, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-BOC DNA or pRK5-CDO DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the BOC and/or CDO polypeptides. The cultures containing transfected cells may undergo further incubation (in serum free medium) and the medium is tested in selected bioassays.

In an alternative technique, DNA encoding the BOC and/or CDO polypeptides may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-BOC DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and reintroduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed BOC and/or CDO can then be concentrated and purified by any selected method, such as dialysis and/or column chromatography.

In another embodiment, the BOC and/or CDO polypeptide can be expressed in CHO cells. The pRK5-BOC pRK5-CDO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of the BOC and/or CDO, the culture medium may be replaced with serum free medium. Preferably, the cultures are incubated for about 6 days, and then the conditioned medium is harvested. The medium containing the expressed BOC and/or CDO polypeptide can then be concentrated and purified by any selected method.

Epitope-tagged BOC and/or CDO polypeptide may also be expressed in host CHO cells. The sequence encoding the BOC and/or CDO portion may be subcloned out of the pRK5 vector. The subclone insert can undergo PCR to fuse in frame with a selected epitope tag such as a poly-his tag into a Baculovirus expression vector. This poly-his tagged BOC and/or CDO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged BOC and/or CDO can then be concentrated and purified by any selected method, such as by $Ni^{2+}$-chelate affinity chromatography.

BOC and/or CDO polypeptide may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT® (Quiagen), DOSPER® or FUGENE® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 12

Expression of BOC and/or CDO in Yeast

The following method describes recombinant expression of BOC and/or CDO polypeptide in yeast.

First, yeast expression vectors are constructed for intracellular production or secretion of the preceding BOC or CDO sequences from the ADH2/GAPDH promoter. DNA encoding such BOC or CDO sequences and the promoter is inserted into suitable restriction enzyme sites in the selected plasmid to direct intracellular expression of BOC or CDO. For secretion, DNA encoding such BOC or CDO sequences can be cloned into the selected plasmid, together with DNA encoding the ADH2/GAPDH promoter, a native BOC or CDO signal peptide or other mammalian signal peptide, or, for example, a yeast alpha-factor or invertase secretory signal/ leader sequence, and linker sequences (if needed) for expression of BOC.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant BOC or CDO can subsequently be isolated and purified by removing the yeast cells from the fermentation medium by centrifugation and then concentrating the medium using selected cartridge filters. The concentrate containing BOC may further be purified using selected column chromatography resins.

Example 13

Expression of BOC or CDO in Baculovirus-Infected Insect Cells

The following method describes recombinant expression of BOC or CDO polypeptide in Baculovirus-infected insect cells.

The sequence coding for the preceding BOC or CDO sequence is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding the preceding BOC or CDO sequence or the desired portion of the coding sequence of such, e.g. the sequence encoding an extracellular domain of a transmembrane protein or the sequence encoding the mature protein if the protein is extracellular, is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged BOC or CDO polypeptide can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged BOC polypeptide are pooled and dialyzed against loading buffer.

Alternatively, purification of the IgG tagged (or Fc tagged) BOC or CDO polypeptide can be performed using known chromatography techniques, including for instance, Protein A or protein G column chromatography.

Example 14

Purification of BOC or CDO Polypeptide Using Specific Antibodies

Native or recombinant BOC or CDO polypeptides may be purified by a variety of standard techniques in the art of protein purification. For example, pro-, mature or pre-polypeptide variants of the preceding BOC or CDO sequences are purified by immunoaffinity chromatography using antibodies specific for such sequences. In general, an immunoaffinity column is constructed by covalently coupling the respective anti-BOC or anti-CDO antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of the preceding BOC or CDO sequences by preparing a fraction from cells containing such sequences in a soluble form. This preparation is derived by solubilization of the whole cell or of a subcellular fraction obtained via differential centrifugation by the addition of detergent or by other methods well known in the art. Alternatively, soluble BOC or CDO polypeptide containing a signal sequence may be secreted in useful quantity into the medium in which the cells are grown.

A soluble BOC or CDO polypeptide-containing preparation is passed over the immunoaffinity column, and the column is washed under conditions that allow the preferential absorbance of such sequences (e.g., high ionic strength buffers in the presence of detergent). Then, the column is eluted under conditions that disrupt the binding between the antibody/substrate (e.g., a low pH buffer such as approximately pH 2-3, or a high concentration of a chaotrope such as urea or thiocyanate ion), and BOC or CDO polypeptide, respectively, is collected.

Example 15

Pooled Human Umbilical Vein Endothelial Cell Proliferation

This assay is designed to determine whether the tested polypeptide shows the ability to modulate proliferation of pooled human umbilical vein endothelial cells in culture and, therefore, function as useful growth or inhibitory factors.

On day 0, pooled human umbilical vein endothelial cells (from cell lines, maximum of 12-14 passages) were plated in 96-well plates at 1000 cells/well per 100 microliter and incubated overnight in complete media [epithelial cell growth media (EGM, Clonetics), plus supplements: human epithelial growth factor (hEGF), bovine brain extract (BBE), hydrocortisone, GA-1000, and fetal bovine serum (FBS, Clonetics)]. On day 1, complete media was replaced by basal media [EGM plus 1% FBS] and addition of BOC or CDO polypeptides at 1%, 0.1% and 0.01%. On day 7, an assessment of cell proliferation was performed by Alamar Blue assay followed by Crystal Violet. Results are expresses as % of the cell growth observed with control buffer.

BOC (PRO1190) polypeptide inhibited proliferation in this assay.

Example 16

Microarray Analysis to Detect Overexpression of BOC and/or CDO Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference.

In the present example, cancerous tumors derived from various human tissues were studied for BOC and/or CDO polypeptide-encoding gene expression relative to non-cancerous human tissue in an attempt to identify those BOC and/or CDO polypeptides which are overexpressed in cancerous tumors. Two sets of experimental data were generated. In one set, cancerous human colon tumor tissue and matched non-cancerous human colon tumor tissue from the same patient ("matched colon control") were obtained and analyzed for BOC and/or CDO polypeptide expression using the above described microarray technology. In the second set of data, cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described BOC and/or CDO polypeptide-encoding nucleic acid sequences were used in the creation of the microarray and RNA from the tumor tissues listed above were used for the hybridization thereto. A value based upon the normalized ratio:experimental ratio was designated as a "cutoff ratio". Only values that were above this cutoff ratio were determined to be significant. Table 7 below shows the results of these experiments, demonstrating that various BOC and/or CDO polypeptides of the present invention are significantly overexpressed in various human tumor tissues as compared to a non-cancerous human tissue control. As described above, these data demonstrate that the BOC and/or PRO polypeptides of the present invention are useful not only as diagnostic markers for the presence of one or more cancerous tumors, but also serve as therapeutic targets for the treatment of those tumors.

TABLE 7

| Molecule | is overexpressed in: | as compared to: |
|---|---|---|
| BOC (PRO1190) | lung tumor | universal normal control |
| BOC (PRO1190) | breast tumor | universal normal control |

Example 17

Generation and Analysis of Mice Comprising BOC (PRO1190) and/or CDO (PRO PRO38430) Gene Disruptions To investigate the role of PRO1190 and PRO38430, genes are produced by homologous recombination or retroviral insertion techniques. Specifically, transgenic mice comprising disruptions in PRO1190 and/or PRO38430 genes (i.e., knockout mice) are created by either gene targeting or gene trapping. Mutations are confirmed by southern blot analysis to confirm correct targeting on both the 5' and 3' ends. Gene-specific genotyping is also performed by genomic PCR to confirm the loss of the endogenous native transcript as demonstrated by RT-PCR using primers that anneal to exons flanking the site of insertion. Targeting vectors are electroporated into 129 strain ES cells and targeted clones are identified. Targeted clones are microinjected into host blastocysts to produce chimeras. Chimeras are bred with C57 animals to produce F1 heterozygotes. Heterozygotes are intercrossed to produce F2 wildtype, heterozygote and homozygote cohorts which are used for phenotypic analysis. If insufficient F1 heterozygotes are produced, the F1 hets can be bred to wild-type C57 mice to produce sufficient heterozygotes to breed for cohorts to be analyzed for a phenotype. All phenotypic analysis is performed from 12-16 weeks after birth.

Example 18

Generation and Analysis of Mice Comprising BOC [DNA59586-1520 (UNQ604)] Gene Disruptions In these knockout experiments, the gene encoding BOC (PRO1190) polypeptides (designated as DNA59586-1520) (UNQ604) and/or CDO (PRO38430) (DNA2279967, UNQ9067) is disrupted. The gene specific information for BOC is as follows: the mutated mouse gene corresponds to nucleotide reference: NM_172506 *Mus musculus* biregional cell adhesion molecule-related/down-regulated by oncogenes (Cdon) binding protein (Boc); protein reference: Q8CE91 ACCESSION:Q8CE91 NID: *Mus musculus* (Mouse). *Mus musculus* 10 days neonate skin cDNA, RIKEN full-length enriched library, clone:4732455C11 product:biregional cell adhesion molecule-related/down-regulated by oncogenes (Cdon)binding protein, full insert sequence; the human gene sequence reference: NM_033254 ACCESSION:NM_033254 NID: gi 15147239 ref NM_033254.1 *Homo sapiens* brother of CDO (BOC); the human protein sequence corresponds to reference: Q9BWV1 ACCESSION: Q9BWV1 NID: *Homo sapiens* (Human). BROTHER OF CDO.

The mouse gene of interest is Boc (biregional cell adhesion molecule-related/down-regulated by oncogenes (Cdon) binding protein), ortholog of human BOC (brother of CDO). Aliases include 4732455C11 and Biregional Cdon binding protein.

BOC is a type I plasma membrane protein that likely functions as a receptor subunit for cell-cell communication. The protein interacts with homolog CDON (cell adhesion molecule-related/down-regulated by oncogenes), N-cadherins, and M-cadherins in a cis fashion, forming a receptor complex at sites of cell-cell contact in myoblasts. During embryonic development, BOC is expressed in musculoskeletal and central nervous systems and in areas of proliferation and differentiation. BOC likely plays a role in muscle cell differentiation and transformation (Wegorzewska et al, *Mol Carcinog* 37(1):1-4 (2003); Mulieri et al, *Dev Dyn* 223(3):379-88 (2002); Kang et al, *EMBO J.* 21(1-2):114-24 (2002); Kang et al, *Proc Natl Acad Sci USA* 100(7):3989-94 (2003)).

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 18 | 30 | 20 | 68 |
| Expected | 17 | 34 | 17 | 68 |

Chi-Sq.=1.3  Significance=0.5220458  (hom/n)=0.25  Avg. Litter Size=9

Mutation Information

Mutation Type: Homologous Recombination (standard)

Description: Coding exons 1 and 2 were targeted (NCBI accession NM_172506.1).

1. Wild-type Expression Panel: Expression of the target gene was detected in embryonic stem (ES) cells and in all 13 adult tissue samples tested by RT-PCR, except skeletal muscle and bone.
2. QC Expression: Disruption of the target gene was confirmed by Southern hybridization analysis.

Example 19

BOC (UNQ604) Binds Shh on the Cell Surface

Cos7 cells were transfected with known Shh-binding cell surface proteins, including Hip, hPTCH1, plus several negative controls, and incubated with Shh-AP (alkaline phosphatase is fused at amino terminal of N-Shh) conditioned medium at room temperature for 1 hr before examination of AP activity on the cell surface. As shown in FIG. 3A, Hip, a cell surface Hh interacting protein, accumulates on the cell surface and binds Shh-AP as indicated by the staining of alkaline phosphatase. Both BOC and the Hh receptor hPTCH1 also bind Shh-AP on the cell surface. No staining was detected when cell were transfected negative control proteins WIF or SFRP (secreted Frizzled Related Protein, known to interact with Wnts), or incubated with AP conditioned medium alone (data not shown). The intensity of the alkaline phosphatase signal reflects how much receptor protein accumulation on the cell surface. Only weak binding of Hh to hPtch2 was detected, reflecting the lack of hPtch2 accumulation at the cell surface.

BOC Overexpression Inhibits Shh Induced Signaling Activity In Vitro.

Figure 4:
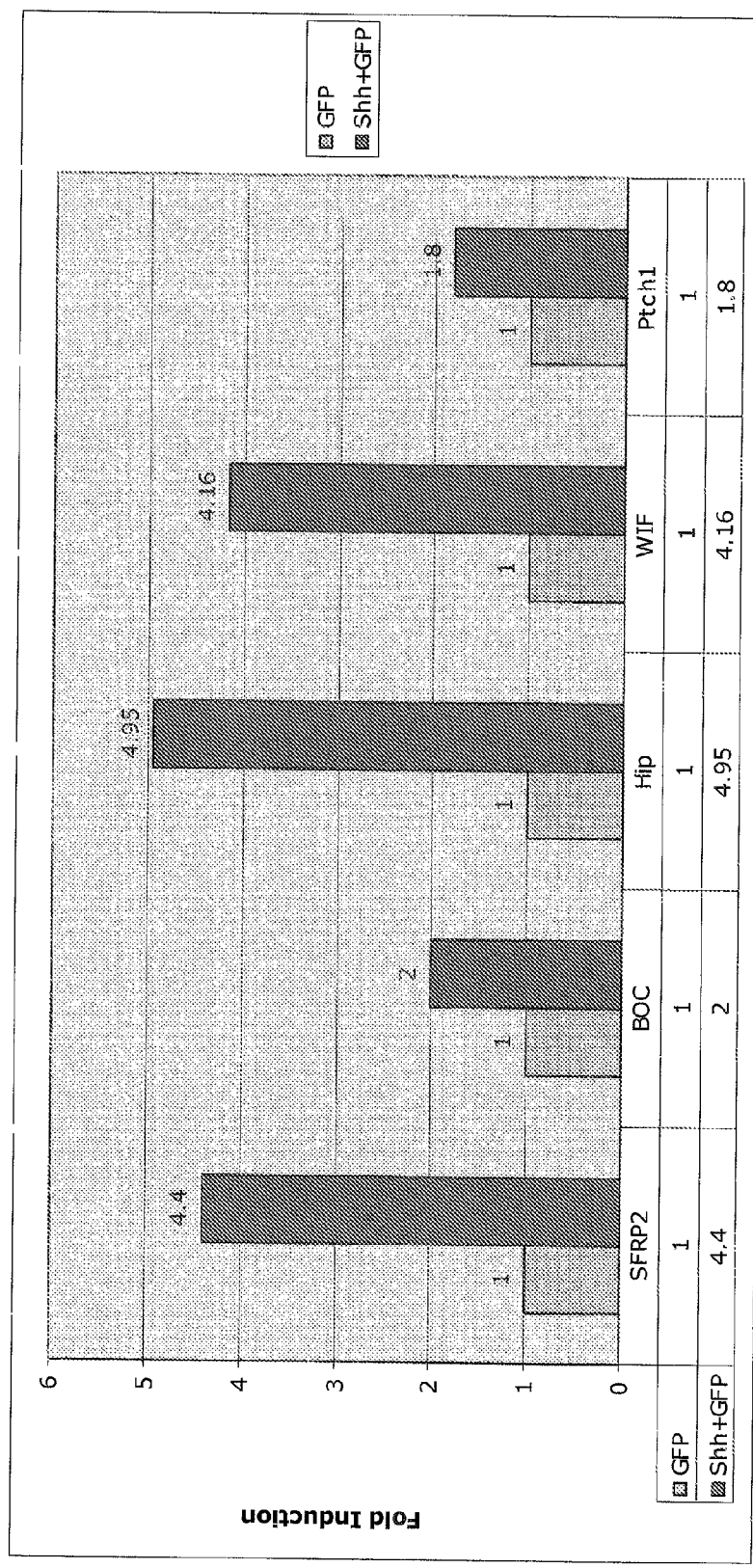
FIG. 4 is a bar graph showing the effect of BOC binding to Shh at the cell surface on Hh induced signaling 10T21/2 cells transfected with expression constructs for BOC and a Bli-Luciferase reporter construct, followed by transient transfection with Shh.
Figure 5:
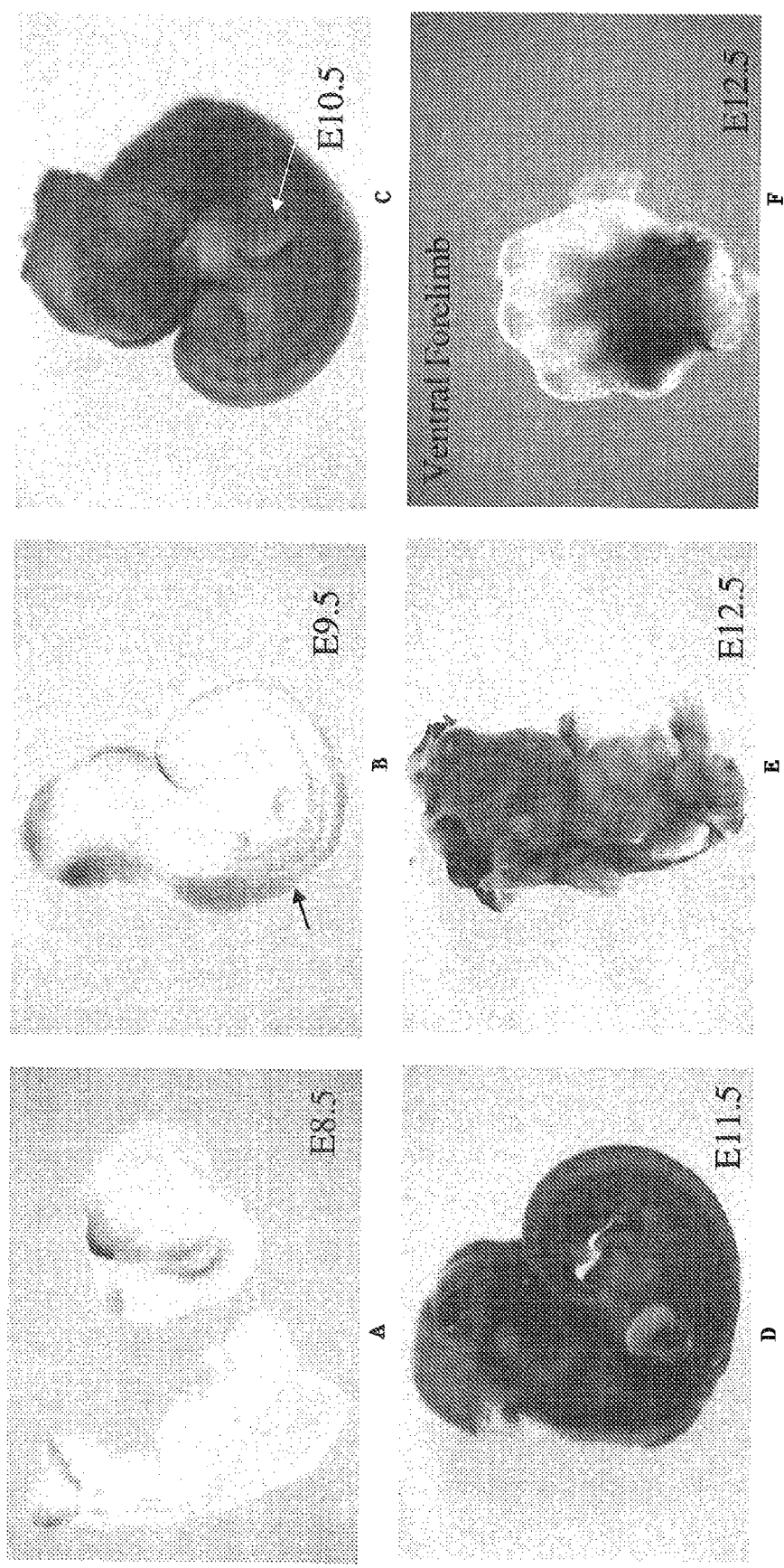
FIG. 5A-F show micrographs illustrating the expression pattern of BOC at various stages of embryonic development.

To explore whether BOC binding to Shh at the cell surface affects Hh induced signaling, we transfected 10T1/2 cell with expression construct for BOC and a Gli-Luciferase reporter constructas readout for Hh signaling. These cells were then mixed with 10T1/2 cells transiently transfected with full-length Shh. As shown in FIG. 4, BOC overexpression on Hh receiving cell inhibited Shh signaling to a similar level as Ptch1 overexpression, suggesting that BOC can inhibit Hh signaling either through ligand trapping or through inhibition of downstream signaling.

BOC Expression Pattern During Embryonic Development.

At early stage of embryonic development, between embryonic day 7.5 and 9.5, BOC is expressed in dorsal neural plate before neural tube closure and at the dorsal neural tube after tube closure. At embryonic day 10, BOC expression is detected in dosal root ganlion (DRG), anterior limb and nasal epithelium. BOC is expressed in area that generally is not exposed to Hh ligand. The protein is enriched on the opposite field of Hh signaling source (ventral neural tube and posterior limb bud), very likely to ensure the proper silencing of Hh signaling in dorsal neural tube and anterior limb bud. The expression pattern of BOC indicates that it may be a potential transcriptional target suppressed by active Hh signaling. One may see upregulation of BOC transcription in Shh knockout animal.

Example 20

CDO (UNQ9067) is a Positive Regulator of Hedeghog Signaling Pathway

Figure 6:
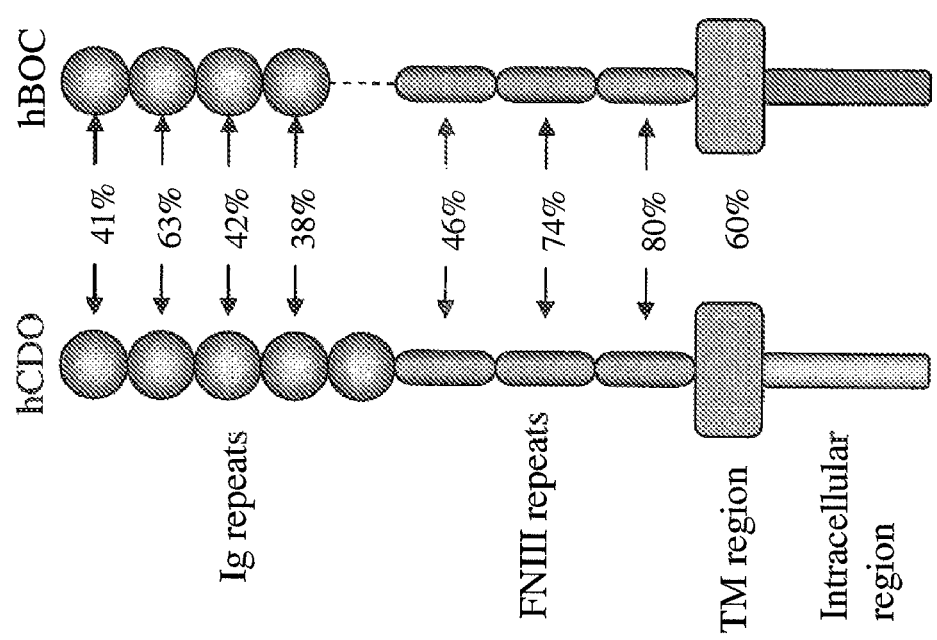
FIG. 6 is a modular comparison between the human CDO and human BOC receptor sequences illustrating the shared structural similarities and sequence identities of the various domains.
Figure 7:
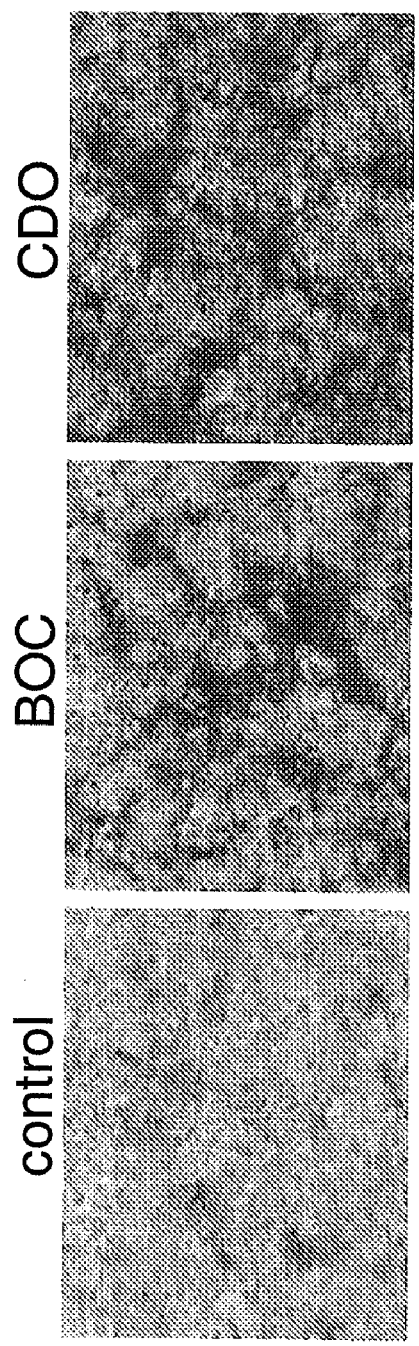
FIG. 7 is a micrograph showing the cell surface expression of BOC and CDO on the cell surface through binding to Shh-AP.

CDO is a cell surface receptor like protein, containing give Ig repeats and three fibronectin (FN) type III repeats in its extracellular region. The ectodomain of CDO is very similar to BOC, which has four Ig repeats and three FN type III domains. The intracellular domain of BOC and CDO do not resemble each other (FIG. 6). Both BOC and CDO bind to Shh-AP on the cell surface (FIG. 7).

Figure 8:
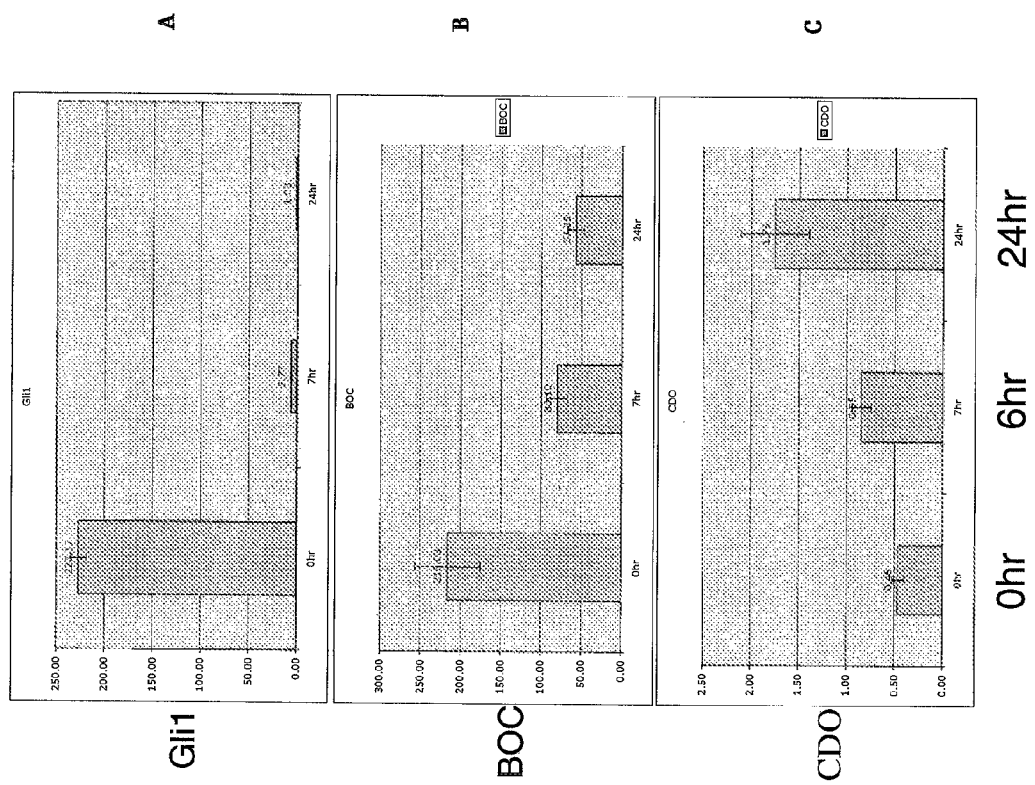
FIGS. 8A-C are graphs of tumor volume in medullo allograft that were treated with the small molecule hedgehog antagonist Cur691. Shown are the downregulation of Hh signaling (indicated by Gli1 downregulation —FIG. 8A), and the differential regulation of BOC and CDO. While BOC is downregulated (FIG. 8B), CDO is upregulated (FIG. 8C), indicated that each are transcriptional targets of the hedgehog pathway, further suggesting that each may play opposing roles in modulating the hedgehog pathway.

CDO and BOC are differentially regulated by hedgehog signaling in medulloblastoma allografts, a model in which Hh signaling is upregulated due to loss of one allele of Patched-1. Treatment of medullo allografts with the hedgehog antagonist CUR691 (described in US20050085519, published Apr. 21, 2005, which is herein incorporated by reference) blocks Hh signaling, as indicated by the downregulation of the Hh target gene Gli-1 (FIG. 8). While BOC is downregulated, CDO is upregulated in response to CUR691 treatment, indicating that both BOC and CDO are transcriptional targets of the Hh pathway, and indicate that each plays opposing roles in modulating the Hh signaling pathway.

Figure 9:
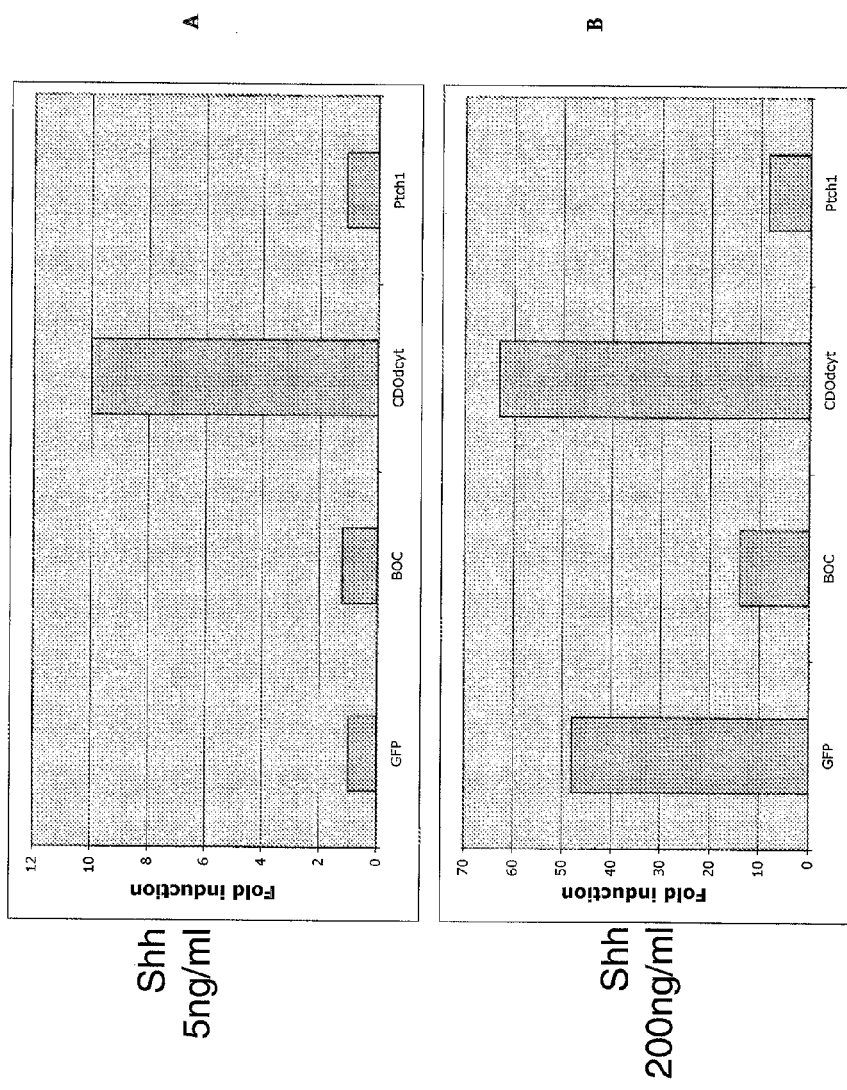
FIGS. 9A-B show overexpression of a truncated form of CDO (CDO Δcyt, CDO lacking cytoplasmic tail) can potentiate hedgehog signaling at suboptimal Shh concentrations (e.g., 5 ng/ml).

Indeed, the overexpression of BOC in 10T1/2 cell culture inhibits Hh signaling at saturating Shh concentration. In contrast, over-expression of a truncated form of CDO, CDOΔcyt (CDO lacking the cytoplasmic tail) potentiates Hh signaling responses at suboptimum Shh concentration. This suggests that the ectodomain can agonize or amplify Hh signaling, and that antagonists targeting this region or the extracellular portion thereof (e.g., anti-CDO antibodies) may have therapeutic utility in inhibiting Hh signaling in target cells (FIG. 9).

What is claimed is:

1. A method for inhibiting interaction of Sonic Hedgehog, Desert Hedgehog, or Indian Hedgehog with Patched-1 or Patched-2 in a cell that expresses Patched-1 or patched-2, comprising contacting said cell with an effective amount of a BOC polypeptide to inhibit said interaction.

2. The method of claim 1, wherein the BOC polypeptide causes inhibition of the growth of the cell.

3. The method of claim 1, wherein the BOC polypeptide causes the death of the cell.

4. The method of claim 1, wherein the cell is a cancer cell.

5. The method of claim 1, wherein the BOC polypeptide comprises the sequence of SEQ ID NO:3.

6. The method of claim 1, wherein the BOC polypeptide is a chimeric BOC polypeptide.

7. The method of claim 6, wherein said chimeric BOC polypeptide comprises a tag polypeptide.

8. The method of claim 6, wherein said chimeric BOC polypeptide is an immunoahesin.

* * * * *